(12) United States Patent
Furst et al.

(10) Patent No.: US 8,070,796 B2
(45) Date of Patent: Dec. 6, 2011

(54) THROMBOSIS INHIBITING GRAFT

(75) Inventors: Joseph G. Furst, Lyndhurst, OH (US); William G. Brodbeck, South Euclid, OH (US)

(73) Assignee: ICON Interventional Systems, Inc., Cleveland, OH (US)

( * ) Notice: Subject to any disclaimer, the term of this patent is extended or adjusted under 35 U.S.C. 154(b) by 1414 days.

(21) Appl. No.: 11/283,434

(22) Filed: Nov. 18, 2005

(65) Prior Publication Data

US 2007/0032864 A1 Feb. 8, 2007

Related U.S. Application Data

(63) Continuation-in-part of application No. 10/810,356, filed on Mar. 26, 2004, which is a continuation-in-part of application No. 10/209,591, filed on Jul. 30, 2002, which is a continuation of application No. 10/039,816, filed on Oct. 26, 2001, now abandoned, which is a continuation-in-part of application No. 09/771,073, filed on Jan. 29, 2001, now abandoned, which is a continuation-in-part of application No. 09/363,052, filed on Jul. 29, 1999, now Pat. No. 6,206,916.

(60) Provisional application No. 60/658,411, filed on Mar. 3, 2005, provisional application No. 60/629,470, filed on Nov. 19, 2004, provisional application No. 60/094,250, filed on Jul. 27, 1998.

(51) Int. Cl.
*A61F 2/06* (2006.01)
*A61M 31/00* (2006.01)

(52) U.S. Cl. ............... 623/1.42; 623/1.15; 623/1.16; 604/509

(58) Field of Classification Search ........... 623/1.11, 623/1.15, 1.16, 1.42, 1.46; 427/261; 424/423; 514/44; 604/509
See application file for complete search history.

(56) References Cited

U.S. PATENT DOCUMENTS

| | | |
|---|---|---|
| 3,964,482 A | 6/1976 | Gerstel |
| 4,739,762 A | 4/1988 | Palmaz |
| 4,773,665 A | 9/1988 | Hindle |
| 4,776,337 A | 10/1988 | Palmaz |
| 4,888,389 A | 12/1989 | Kennedy et al. |
| 4,942,204 A | 7/1990 | Kennedy |
| 5,024,671 A | 6/1991 | Tu et al. |
| 5,037,392 A | 8/1991 | Hillstead |
| 5,051,272 A | 9/1991 | Hermes et al. |
| 5,059,166 A | 10/1991 | Fischell et al. |
| 5,067,491 A | 11/1991 | Taylor, II et al. |

(Continued)

FOREIGN PATENT DOCUMENTS

EP 04330011 A1 6/1991

(Continued)

OTHER PUBLICATIONS

Matsuda, 2002. Device-directed therapeutic drug delivery systems. Journal of Controlled Release, vol. 78:125-131.

(Continued)

*Primary Examiner* — Vy Q Bui
(74) *Attorney, Agent, or Firm* — Fay Sharpe LLP; Brian E. Turung

(57) ABSTRACT

A medical method that is adapted for introducing the medical device into the vascular system of a body which is designed to inhibit or prevent thrombosis after the insertion of the medical device.

26 Claims, 5 Drawing Sheets

U.S. PATENT DOCUMENTS

| | | | |
|---|---|---|---|
| 5,073,381 A | 12/1991 | Ivan et al. | |
| 5,102,417 A | 4/1992 | Palmaz | |
| 5,108,366 A | 4/1992 | Schatz | |
| 5,108,424 A | 4/1992 | Hoffman, Jr. et al. | |
| 5,116,318 A | 5/1992 | Hillstead | |
| 5,185,408 A | 2/1993 | Tang et al. | |
| 5,195,984 A | 3/1993 | Schatz | |
| 5,197,977 A | 3/1993 | Hoffman, Jr. et al. | |
| 5,246,452 A | 9/1993 | Sinnott | |
| 5,283,257 A | 2/1994 | Gregory et al. | |
| 5,304,121 A | 4/1994 | Sahatjian | |
| 5,306,250 A | 4/1994 | March et al. | |
| 5,316,023 A | 5/1994 | Palmaz | |
| 5,344,426 A | 9/1994 | Lau et al. | |
| 5,370,681 A | 12/1994 | Herweck et al. | |
| 5,383,927 A | 1/1995 | Degoicoechea et al. | |
| 5,383,928 A | 1/1995 | Scott et al. | |
| 5,417,981 A | 5/1995 | Endo et al. | |
| 5,443,498 A | 8/1995 | Fontaine | |
| 5,449,382 A | 9/1995 | Dayton | |
| 5,462,575 A | 10/1995 | Del Corso | |
| 5,464,650 A | 11/1995 | Berg et al. | |
| 5,500,013 A | 3/1996 | Buscemi et al. | |
| 5,516,781 A | 5/1996 | Morris et al. | |
| 5,545,208 A | 8/1996 | Wolff et al. | |
| 5,556,754 A | 9/1996 | Singer | |
| 5,563,056 A | 10/1996 | Swan et al. | |
| 5,563,146 A | 10/1996 | Morris et al. | |
| 5,571,170 A | 11/1996 | Palmaz | |
| 5,578,075 A | 11/1996 | Dayton | |
| 5,578,645 A | 11/1996 | Askanazi | |
| 5,605,696 A | 2/1997 | Eury et al. | |
| 5,609,629 A | 3/1997 | Fearnot et al. | |
| 5,616,608 A | 4/1997 | Kinsella et al. | |
| 5,624,411 A | 4/1997 | Tuch | |
| 5,649,977 A | 7/1997 | Campbell | |
| 5,665,728 A | 9/1997 | Morris et al. | |
| 5,679,400 A | 10/1997 | Tuch | |
| 5,695,516 A | 12/1997 | Fischell et al. | |
| 5,716,981 A | 2/1998 | Hunter et al. | |
| 5,725,572 A | 3/1998 | Lam et al. | |
| 5,733,303 A | 3/1998 | Israel et al. | |
| 5,733,925 A | 3/1998 | Kunz et al. | |
| 5,735,871 A | 4/1998 | Sgro | |
| 5,755,781 A | 5/1998 | Jayaraman | |
| 5,772,864 A | 6/1998 | Møller et al. | |
| 5,776,183 A | 7/1998 | Kanesaka et al. | |
| 5,807,944 A | 9/1998 | Hirt et al. | |
| 5,811,447 A | 9/1998 | Kunz et al. | |
| 5,824,045 A | 10/1998 | Alt | |
| 5,824,049 A | 10/1998 | Ragheb et al. | |
| 5,824,077 A | 10/1998 | Mayer | |
| 5,837,313 A | 11/1998 | Ding et al. | |
| 5,843,172 A | 12/1998 | Yan | |
| 5,849,368 A | 12/1998 | Hostettler et al. | |
| 5,853,419 A | 12/1998 | Imran | |
| 5,861,027 A | 1/1999 | Trapp | |
| 5,873,904 A | 2/1999 | Ragheb et al. | |
| 5,879,370 A | 3/1999 | Fischell et al. | |
| 5,911,732 A | 6/1999 | Hojeibane | |
| 5,916,585 A | 6/1999 | Cook et al. | |
| 5,946,585 A | 8/1999 | Zhang et al. | |
| 5,962,620 A | 10/1999 | Reich et al. | |
| 5,964,798 A | 10/1999 | Imran | |
| 5,968,091 A | 10/1999 | Pinchuk et al. | |
| 5,981,568 A | 11/1999 | Kunz et al. | |
| 5,993,972 A | 11/1999 | Reich et al. | |
| 6,007,573 A | 12/1999 | Wallace et al. | |
| 6,059,810 A | 5/2000 | Brown et al. | |
| 6,066,325 A | 5/2000 | Wallace et al. | |
| 6,074,659 A | 6/2000 | Kunz et al. | |
| 6,096,070 A | 8/2000 | Ragheb et al. | |
| 6,099,561 A | 8/2000 | Alt | |
| 6,120,536 A | 9/2000 | Ding et al. | |
| 6,120,847 A | 9/2000 | Yang et al. | |
| 6,126,247 A | 10/2000 | Paul et al. | |
| 6,146,358 A | 11/2000 | Rowe | |
| 6,156,062 A | 12/2000 | McGuinness | |
| 6,156,373 A | 12/2000 | Zhong et al. | |
| 6,171,609 B1 | 1/2001 | Kunz | |
| 6,197,013 B1 * | 3/2001 | Reed et al. | 604/509 |
| 6,200,337 B1 | 3/2001 | Moriuchi et al. | |
| 6,200,589 B1 | 3/2001 | Kennedy et al. | |
| 6,200,960 B1 | 3/2001 | Khachigian | |
| 6,206,916 B1 | 3/2001 | Furst | |
| 6,221,099 B1 | 4/2001 | Andersen et al. | |
| 6,245,537 B1 | 6/2001 | Williams et al. | |
| 6,258,121 B1 | 7/2001 | Yang et al. | |
| 6,268,390 B1 | 7/2001 | Kunz | |
| 6,273,908 B1 | 8/2001 | Ndondo-Lay | |
| 6,273,913 B1 | 8/2001 | Wright et al. | |
| 6,287,628 B1 | 9/2001 | Hossainy et al. | |
| 6,290,721 B1 | 9/2001 | Heath | |
| 6,299,604 B1 | 10/2001 | Ragheb et al. | |
| 6,306,421 B1 | 10/2001 | Kunz et al. | |
| 6,322,847 B1 | 11/2001 | Zhong et al. | |
| 6,334,856 B1 | 1/2002 | Allen et al. | |
| 6,335,029 B1 | 1/2002 | Kamath et al. | |
| 6,346,133 B1 | 2/2002 | Narasimhan et al. | |
| 6,356,600 B1 | 3/2002 | Kirsteins et al. | |
| 6,358,556 B1 | 3/2002 | Ding et al. | |
| 6,358,989 B1 | 3/2002 | Kunz et al. | |
| 6,365,171 B1 | 4/2002 | Kennedy et al. | |
| 6,365,616 B1 | 4/2002 | Kohn | |
| 6,368,658 B1 | 4/2002 | Schwarz et al. | |
| 6,369,065 B1 | 4/2002 | Chatelain et al. | |
| 6,379,379 B1 | 4/2002 | Wang | |
| 6,379,381 B1 | 4/2002 | Hossainy et al. | |
| 6,391,052 B2 | 5/2002 | Buirge et al. | |
| 6,399,144 B2 | 6/2002 | Dinh et al. | |
| 6,419,692 B1 | 7/2002 | Yang et al. | |
| 6,436,133 B1 | 8/2002 | Furst et al. | |
| 6,440,460 B1 | 8/2002 | Gurny et al. | |
| 6,485,502 B2 | 11/2002 | Don Michael et al. | |
| 6,488,702 B1 | 12/2002 | Besselink | |
| 6,491,938 B2 | 12/2002 | Kunz et al. | |
| 6,515,009 B1 * | 2/2003 | Kunz et al. | 514/411 |
| 6,517,571 B1 | 2/2003 | Brauker et al. | |
| 6,527,802 B1 | 3/2003 | Mayer | |
| 6,528,584 B2 | 3/2003 | Kennedy et al. | |
| 6,530,951 B1 | 3/2003 | Bates et al. | |
| 6,545,097 B2 | 4/2003 | Pinchuk et al. | |
| 6,555,157 B1 | 4/2003 | Hossainy | |
| 6,555,619 B1 | 4/2003 | Kennedy et al. | |
| 6,569,195 B2 | 5/2003 | Yang et al. | |
| 6,569,441 B2 | 5/2003 | Kunz et al. | |
| 6,583,251 B1 | 6/2003 | Chaikof et al. | |
| 6,585,764 B2 | 7/2003 | Wright et al. | |
| 6,599,275 B1 | 7/2003 | Fischer, Jr. | |
| 6,599,928 B2 | 7/2003 | Kunz et al. | |
| 6,607,598 B2 | 8/2003 | Schwarz et al. | |
| 6,623,521 B2 | 9/2003 | Steinke et al. | |
| 6,624,138 B1 | 9/2003 | Sung et al. | |
| 6,641,611 B2 | 11/2003 | Jayaraman | |
| 6,652,575 B2 | 11/2003 | Wang | |
| 6,656,506 B1 | 12/2003 | Wu et al. | |
| 6,656,966 B2 | 12/2003 | Garvey et al. | |
| 6,663,881 B2 | 12/2003 | Kunz et al. | |
| 6,669,502 B1 | 12/2003 | Bernhart et al. | |
| 6,669,718 B2 | 12/2003 | Besselink | |
| 6,676,937 B1 * | 1/2004 | Isner et al. | 424/93.7 |
| 6,695,833 B1 | 2/2004 | Frantzen | |
| 6,709,379 B1 | 3/2004 | Brandau et al. | |
| 6,720,350 B2 | 4/2004 | Kunz et al. | |
| 6,723,120 B2 | 4/2004 | Yan | |
| 6,726,923 B2 | 4/2004 | Iyer et al. | |
| 6,730,064 B2 | 5/2004 | Ragheb et al. | |
| 6,730,349 B2 | 5/2004 | Schwarz et al. | |
| 6,730,699 B2 | 5/2004 | Li et al. | |
| 6,734,194 B2 | 5/2004 | End et al. | |
| 6,743,805 B2 | 6/2004 | End et al. | |
| 6,749,554 B1 | 6/2004 | Snow et al. | |
| 6,753,071 B1 | 6/2004 | Pacetti | |
| 6,759,431 B2 | 7/2004 | Hunter et al. | |
| 6,764,505 B1 | 7/2004 | Hossainy et al. | |
| 6,767,360 B1 | 7/2004 | Alt et al. | |
| 6,770,729 B2 | 8/2004 | Van Antwerp | |

| | | |
|---|---|---|
| 6,774,278 B1 | 8/2004 | Ragheb et al. |
| 6,780,849 B2 | 8/2004 | Herrmann et al. |
| 6,783,793 B1 | 8/2004 | Hossainy et al. |
| 6,790,218 B2 | 9/2004 | Jayaraman |
| 6,790,372 B2 | 9/2004 | Roy |
| 6,808,536 B2 | 10/2004 | Wright et al. |
| 6,861,406 B2 | 3/2005 | Mascarenhas |
| 6,887,851 B2 | 5/2005 | Mascarenhas |
| 6,914,049 B2 | 7/2005 | Mascarenhas |
| 6,924,087 B2 | 8/2005 | Yeshurun |
| 6,939,863 B2 | 9/2005 | Chen |
| 2001/0014717 A1 | 8/2001 | Hossainy et al. |
| 2002/0004101 A1 | 1/2002 | Ding et al. |
| 2002/0013275 A1 | 1/2002 | Kunz et al. |
| 2002/0032414 A1 | 3/2002 | Ragheb et al. |
| 2002/0051730 A1 | 5/2002 | Bodnar et al. |
| 2002/0054900 A1 | 5/2002 | Kamath et al. |
| 2002/0071902 A1 | 6/2002 | Ding et al. |
| 2002/0082679 A1* | 6/2002 | Sirhan et al. ............ 623/1.15 |
| 2002/0091433 A1 | 7/2002 | Ding et al. |
| 2002/0095133 A1 | 7/2002 | Gillis et al. |
| 2002/0142974 A1 | 10/2002 | Kohn |
| 2003/0026840 A1 | 2/2003 | Plank et al. |
| 2003/0028243 A1 | 2/2003 | Bates et al. |
| 2003/0028244 A1 | 2/2003 | Bates et al. |
| 2003/0036794 A1 | 2/2003 | Ragheb et al. |
| 2003/0040790 A1 | 2/2003 | Furst |
| 2003/0064098 A1 | 4/2003 | Kararli et al. |
| 2003/0083646 A1 | 5/2003 | Sirhan et al. |
| 2003/0093141 A1 | 5/2003 | DiMatteo et al. |
| 2003/0099712 A1 | 5/2003 | Jayaraman |
| 2003/0100499 A1 | 5/2003 | Epstein |
| 2003/0158598 A1* | 8/2003 | Ashton et al. ............ 623/1.42 |
| 2003/0199969 A1 | 10/2003 | Steinke et al. |
| 2003/0216534 A1 | 11/2003 | Chaikof et al. |
| 2003/0228364 A1 | 12/2003 | Nathan |
| 2003/0229390 A1 | 12/2003 | Ashton |
| 2003/0229392 A1 | 12/2003 | Wong |
| 2003/0229393 A1 | 12/2003 | Kutryk et al. |
| 2004/0000046 A1 | 1/2004 | Stinson |
| 2004/0047909 A1 | 3/2004 | Ragheb et al. |
| 2004/0049265 A1 | 3/2004 | Ding et al. |
| 2004/0093076 A1 | 5/2004 | White |
| 2004/0093077 A1 | 5/2004 | White |
| 2004/0193247 A1 | 9/2004 | Besselink |
| 2004/0208985 A1 | 10/2004 | Rowan et al. |
| 2004/0219223 A1 | 11/2004 | Kunz et al. |
| 2004/0243225 A1 | 12/2004 | Ragheb et al. |

FOREIGN PATENT DOCUMENTS

| | | |
|---|---|---|
| EP | 0 608 817 | 8/1994 |
| EP | 0 700 685 | 3/1996 |
| EP | 0 756 853 | 2/1997 |
| EP | 0 770 694 | 5/1997 |
| EP | 0 836839 A2 | 4/1998 |
| EP | 0 875 218 | 11/1998 |
| EP | 1 046 722 | 10/2000 |
| SU | 263 888 | 2/1970 |
| SU | 333 209 | 3/1972 |
| SU | 489 801 | 10/1975 |
| WO | WO 93/16176 | 8/1993 |
| WO | WO 94/07529 | 4/1994 |
| WO | WO 94/16706 | 8/1994 |
| WO | WO 94/26291 | 11/1994 |
| WO | WO 96/25176 | 8/1996 |
| WO | WO 97/10011 | 3/1997 |
| WO | WO 98/17331 | 4/1998 |
| WO | WO 98/43618 | 10/1998 |
| WO | WO 99/18998 | 4/1999 |
| WO | WO 99/49907 | 10/1999 |
| WO | WO 99/56663 | 11/1999 |
| WO | WO 00/12175 | 3/2000 |
| WO | WO 01/01957 | 1/2001 |
| WO | WO 01/17577 | 3/2001 |
| WO | WO 01/41678 | 6/2001 |
| WO | WO 01/45763 | 6/2001 |
| WO | WO 01/45787 | 6/2001 |
| WO | WO 01/97964 | 12/2001 |
| WO | WO 02/078764 | 10/2002 |
| WO | WO 2004/003240 | 1/2004 |
| WO | WO 2004/019822 | 3/2004 |
| WO | WO 2004/022122 | 3/2004 |

OTHER PUBLICATIONS

Regar et al., 2001. Stent development and local drug delivery. British Medical Bulletin, vol. 59:277-248.

*Trapidil Inhibits Monocyte Chemoattractant Protein-1 and macrophage Accumulation After Balloon Arterial Injury in Rabbits*, Poon M, Cohen J, Siddiqui Z, et al., Lab Invest. 1999; 79:1369-1375.

*The TRAPIST study—A multicentre randomized placebo controlled clinical trial of trapidil for prevention of restenosis after coronary stenting, measured by 3-D intravascular ultrasound*, P.W. Serruys, D.P. Foley, M. Pieper, J.A. de Feyter on behalf of the TRAPIST investigators, European Heart Journal (2001) 22, 1938-1947, doi:10.1053/euhj.2001.2627, available online at http:/www.idealibrary.com.

Abstract of *Fast and Reproducible Vascular Neointima Formation in the Hamster Carotid Artery: Effects of Trapidil and Captopril*, Matsuno H, Stassen JM, Hoylaerts MF, Vermylen J, Deckmyn H., Thromb Haemost. Dec. 1995;74(6):1591-6.

*Results of a Meta-Analysis of Trapidil, a PDGF Inhibitor A'A Sufficient Reason for a Second Look to the Pharmacological Approach to Restenosis*, Serruys PW, Benz K, Darcis T, Mignot A, van Es GA, Schwicker D., J Invasive Cardiol. Oct. 1997;9(8):505-512.

*Management of restenosis after Coronary Intervention*, Dangas G, Fuster V., Am Heart J. Aug. 1996;132(2 Pt 1):428-36.

*-New Aspects in Antithrombotic Therapy—Platelet Inhibitors-*, Terres W, Meinertz T., Herz. Feb. 1996;21(1):1-11.

*A Randomized Comparison of Trapidil (triazolopyrimidine), a Platelet-Derived Growth Factor Antagonist, Versus Aspirin in Prevention of Angiographic Restenosis after Coronary Artery Palmaz-Schatz Stent Implantation*, Galassi AR, Tamburino C, Nicosia A, Russo G, Grassi R, Monaco A, Giuffrida G., Catheter Cardiovasc Interv. Feb. 1999;46(2):162-8.

*Reference Chart Derived From Post-Stent-Implantation Intravascular Ultrasound Predictors of 6-Month Expected Restenosis on Quantitative Coronary Angiography*, P. J. de Feyter, P. Kay, C. Disco, and P. W. Serruys, Circulation, Oct. 1999; 100: 1777-1783, Abstract of *Trapidil in Preventing Restenosis After Balloon Angioplasty in the Ather Osclerotic Rabbit*, MW Liu, GS Roubin, KA Robinson, AJ Black, JA Hearn, RJ Siegel, and SB King, 3d Circulation 1990 81: 1089-1093.

Abstract of *Effects of Trapidil (Triazolopyrimidine), a Platelet-Derived Growth Factor Antagonist, in Preventing Restenosis After Percutaneous Transluminal Coronary Angioplasty*, Okamoto S, Inden M, Setsuda M, Konishi T, Nakano T, Am Heart J. Jun. 1992; 123(6)1439-44.

Abstract of *Trapidil (triazolopyrimidine), A Platelet-Derived Growth Factor Antagonist, Reduces Restenosis After Percutaneous Transluminal Coronary Angioplasty. Results of the Randomized, Double-Blind STARC Study. Studio Trapidil Versus Aspirin Nella Restenosi Coronarica*, A Maresta, M Balducelli, L Cantini, A Casari, R Chioin, M Fabbri, A Fontanelli, PA Monici Preti, S Repetto, and S De Serv, Circulation, Dec. 1994; 90: 2710-2715.

Abstract of *The Trapidil Restenosis Trial (STARC study): Background, Methods and Clinical Characteristics of the Patient Population*, Maresta A, Balducelli M, Cantini L, Casari A, Chioin R, Fontanelli A, Monici Preti PA, Repetto S, Raffaghello S.,Clin Trials Metaanal. Apr. 1994,29(1):31-40.

Abstract of *Pharmacological Properties of Trapidil: Comparison with Other Coronary Vasodilators*, Ohnishi H, Kosuzume H, Yamaguchi K, Sato M, Umehara S, Funato H, Itoh C, Suzuki K, Kitamura Y, Suzuki Y, Itoh R., Nippon Yakurigaku Zasshi. Sep. 1980; 76(6):495-503.

Abstract of *Effects of Trapidil on Thromboxane A2-induced Aggregation of Platelets, Ischemic Changes in Heart and Biosynthesis of Thromboxane A2*, Ohnishi H, Kosuzume H, Hayashi Y, Yamaguchi K, Suzuki Y, Itoh R., Prostaglandins Med. Mar. 1981;6(3):269-81.

Abstract of *Antithrombotic Activity and the Mechanism of Action of Trapidil (Rocomal)*, Suzuki Y, Yamaguchi K, Shimada S, Kitamura Y, Ohnishi H., Prostaglandins Leukot Med. Dec. 1982;9(6):685-95.

Abstract of *Suppression of Fibroblast Proliferation in Vitro and of Myointimal Hyperplasia in Vivo by the Triazolopyrimidine, Trapidil*, Tiell ML, Sussman II, Gordon PB, Saunders RN, Artery. 1983;12(1):33-50.

*Influence of Cardiovascular Drugs on Platelet Aggregation*, Forster W, Block HU, Giessler C, Heinroth I, Mentz P, Ponicke K, Rettkowski W, Zehl U., : Adv Myocardiol. 1983;4:539-47.

Trapidil in Preventing Restenosis Alter Balloon Angioplasty in the Atherosclerotic Rabbit, Liu, et al., *Circulation*, vol. 81, No. 3, Mar. 1990.

DNA Delivery from Polymer Matrices for Tissue Engineering, Shea, et al., *Nature Biotechnology*, vol. 17, Jun. 1999.

Polymeric System for Dual Growth Factor Delivery, Richardson, et al., *Nature Biotechnology*, vol. 19, Nov. 2001. E.

Controlled Growth Factor Release from Synthetic Extracellular Matrices, Lee, et al., *Nature*, vol. 408, Dec. 21/28, 2000.

*Progress in Cardiovascular Disease*, Sonnenblick, et al., Sep./Oct. 1996.

*USCI PE Plus Peripheral Balloon Dilatation Catheter* brochure.

Refractory Metals Forum: Rhenium and its Alloys, B.D. Bryskin.

The Effect of Annealing Practice on the Structure and Mechanical Properties of P/M MO—47.5% Re Alloy, John A. Shields, Jr. CLI-MAX Specialty Metals, Cleveland, OH 4411.

Delute Mo-Re Alloys—A Critical Evaluation of Their Comparative Mechanical Properties, J. Watsworth, T.T. Nieg, and J.J. Stephens.

Technology Status of Molybdenum and Tungsten Alloys, W.D. Klopp, Materials Consultant, 1542 Mendelssohn Dr., Westlake, OH 44145.

The Alloys of Rhenium with Molybdenum or with Tungsten and Having Good High Temperature Properties, G.A. Geach and J.E. Hughes.

Behaviour of Tungsten, Molybdenum, and Alloys under Unusual Heating Conditions, Ralf Eck, Hubert Bildstein, Fritz Simader, Roland Stickler, Josef Tinzl.

Rhenium and Molybdenum/Tungsten Based Alloys: An Overview of Database, Boris D. Bryskin and Jan C. Carlen.

Mechanical Properties of Mo-Re Alloys at Different Test Temperatures, A.V. Abramyan, N.N. Morgunova, S.A. Golovanenko, and N.I. Kazakova.

Needles, Sutures and Knots, Part III; Specific Suture Materials Al Sherbeeny,M., MD, vol. 1, Jul. 2004.

Microsystems for Drug and Gene Delivery, Michael L. Reed, Senior Member, IEEE & Whye-Kei Lye, Member, IEEE.

Silicon Micromachined Hollow Microneedles for Transdermal Liquid Transport, Jan J.G.E. Gardeniers, Regina Luttge, Erwin J.W. Berenschot, Meint J. De Boer, Shuki Y. Yeshurun, Meir Hefetz, Ronnyb van't Oever, and Abert van den Berg, Journal of Microelectromechanical Systems, vol. 12, No. 6, Dec. 200.

A New Method for the Estimation for the Absorption Time of Bioabsorbable Polymers in the Body, D.C.tunc, M. Gockbora and P.Higham/ Stryker Howmedica Osteonics, Advanced Technology Group, Mahwa, NJ 07430 USA.

Synthesis and comparative biodegradability studies of three poly(alkylene succinate)s. D. Bikiaris, G. Papageorgiou, D. Achilias, Laboratory of Organic Chemical Technology, Dept. of Chemistry, Aristotle University of Thessaloniki, GR-541 24, Thessaloniki, Macedonia, Greece.

\* cited by examiner

THROMBOSIS INHIBITING GRAFT

The present invention claims priority on U.S. Provisional Application Ser. No. 60/629,470 filed Nov. 19, 2004 and 60/658,411 filed Mar. 3, 2005, which are incorporated herein by reference.

The present invention is also a continuation in part of U.S. application Ser. No. 10/810,356 filed Mar. 26, 2004, which in turn is a continuation of U.S. application Ser. No. 10/039,816 filed on Oct. 26, 2001, now abandoned, which in turn is a continuation-in-part of U.S. patent application Ser. No. 09/771,073 filed Jan. 29, 2001, now abandoned, which in turn is a continuation-in-part of U.S. patent application Ser. No. 09/363,052 filed Jul. 29, 1999, now U.S. Pat. No. 6,206,916, which in turn claims priority on U.S. Provisional Patent Application Ser. No. 60/094,250 filed Jul. 27, 1998, which are incorporated herein by reference.

The present invention is also a continuation in part of U.S. application Ser. No. 10/209,591 filed Jul. 30, 2002, which in turn is a continuation-in-part of U.S. patent application Ser. No. 10/039,816 filed Oct. 26, 2001, which in turn is a continuation-in-part of U.S. patent application Ser. No. 09/771,073 filed Jan. 29, 2001, which in turn is a continuation-in-part of U.S. patent application Ser. No. 09/363,052 filed Jul. 29, 1999, now U.S. Pat. No. 6,206,916, which in turn claims priority on U.S. Provisional Patent Application Ser. No. 60/094,250 filed Jul. 27, 1998, which are incorporated herein by reference.

The invention relates generally to medical devices, and particularly to an implant for use within a body, and more particularly to an expandable graft which is useful in repairing various types of body passageways, and even more particularly to an expandable graft which is useful in repairing blood vessels narrowed or occluded by disease.

BACKGROUND OF THE INVENTION

Medical treatment of various illnesses or diseases commonly includes the use of one or more medical devices. Two types of medical devices that are commonly used to repair various types of body passageways are an expandable graft or stent, or a surgical graft. These devices have been implanted in various areas of the mammalian anatomy.

Old age, dietary habits and primary genetics can also lead to a common disease, atherosclerosis. Atherosclerotic plaques and blockages consist of lipids, fibroblasts and fibrin that proliferate and cause obstruction of a vessel. As the obstruction grows, the blood flow diminishes and reaches a level that is insufficient to meet the biological needs of one or more organs. The end result is defined as ischemia.

One purpose of a stent is to open a blocked or partially blocked body passageway. When a stent is used in a blood vessel, the stent is used to open the occluded vessel to achieve improved blood flow which is necessary to provide for the anatomical function of an organ. The procedure of opening a blocked or partially blocked body passageway commonly includes the use of one or more stents in combination with other medical devices such as, but not limited to, an introducer sheath, a guiding catheter, a guide wire, an angioplasty balloon, etc.

During the insertion of the stent, some disruption of the native body passageway can occur. This disruption to the body passageway can start a cascade of biological occurrences that can hinder the function of the implanted stent. When a stent is inserted into a blood vessel, a) platelets can be activated, b) smooth muscle cells can migrate and/or c) endothelial cells, which protect the vessel, can be disrupted thus leading to the cascade of clot formation. Clot formation can lead to the failure of the stent. The accumulation of platelets about the implanted stent is known as thrombosis.

Another medical procedure that is utilized frequently involves bypass (heart surgery), or peripheral (non-cardiac) grafting. This medical procedure entails using a surgical graft constructed of an artificial material that replaces or by-passes the diseased portion of the vessel. This procedure is accomplished by ligating the diseased portion of the vessel, temporarily stopping blood flow, and physically sewing in the surgical with a suture. The failure of the medical procedure commonly occurs at the suture (anastomoses) site. When the surgical graft is connected to a blood vessel, a) platelets can be activated, b) smooth muscle cells can migrate and/or c) endothelial cells, which protect the vessel, can be disrupted thus leading to the cascade of clot formation. The clot formation can lead to the failure of the surgical graft. The accumulation of platelets about the sutured regions is also known as thrombosis. This failure can then lead to repeat procedures, amputation and/or other medical complications.

During and after a medical procedure, the patient is commonly placed on aggressive anti-platelet and/or anti-coagulation therapy. A major concern and side effect of such treatment is an increased incidence of bleeding complications. These bleeding complications can make the most routine procedure such as getting your teeth cleaned prohibited.

Many other types of diseases are treatable with stents, catheters, surgical grafts, and/or other devices inserted into vessels or other locations in the body. In addition, various types of orthopedic devices can be used to treat various diseased and/or damaged areas of a body. One desirable technique would be to deliver one or more biological agents directly to the site that has been treated and/or at the site of potential failure once a medical device has been inserted in the treatment site. In one non-limiting example, it would be desirable to have a medical device and/or a medical method or technique that can be used to deliver an anti-platelet and/or other medication to the region of a body passageway which has been treated by a stent or by another interventional technique. In another and/or alternative non-limiting example, it would be desirable to have a medical device that could deliver one or more biological agents over the short term (e.g, seconds, minutes, hours, days) with a potential burst effect of the one or more biological agents, and/or the long term (e.g. days, weeks, months, years) after the initial implantation of the medical device. In still another and/or alternative non-limiting example, it would be desirable to provide control over the delivery rate of one or more biological agents from the medical device, thus limiting or eliminating the systemic effects of taking a drug (e.g, orally, intravenously, etc.) over extended periods of time.

In view of the present state of medical device technology, there is a need and demand for a medical device that can be inserted into a treatment site and which has improved procedural success rates and inhibits or prevents the occurrence of thrombosis after the medical device has been inserted into the treatment area result in the elimination of the need for or the reduction in the need for aggressive anti-platelet and/or anti-coagulation therapy after insertion of the medical device.

SUMMARY OF THE INVENTION

The previously mentioned short-comings of prior art medical devices are addressed by the novel medical device of the present invention. The medical device of the present invention can be designed to be inserted into a treatment site such that the medical device has improved procedural success rates and inhibits or prevents the occurrence of thrombosis after the medical device has been inserted into the treatment area. The improved procedural success rate and the inhibition or prevention of the occurrence of thrombosis by the medical device of the present invention can be achievable without the need for or with a significant reduction in need for aggressive anti-platelet and/or anti-coagulation therapy after insertion of the medical device in the treatment area. The improved medical procedure of the present invention can be at least partially obtained by the use of a medical device that 1) is formed of one or more materials that enhances the physical properties of the medical device, and/or 2) includes one or more biological agents (e.g., anti-platelet medication, etc.) that can be controllably and/or uncontrollably delivered at, adjacent to and/or into a treatment site by the medical device. The medical device in accordance with the present invention can be in the form of many different devices such as, but not limited to, stents, grafts, surgical grafts (e.g., vascular grafts, etc.), valves, orthopedic implants, sheaths, guide wires, balloon catheters, hypotubes, catheters (e.g., electrophysiology catheters, guide catheter, stent catheter, etc.), cutting devices, PFO (patent foramen ovale) device, sutures, staples, bandages, wraps, biological glue, etc. In one non-limiting embodiment, the medical device is directed for use in a body passageway. As defined herein, the term "body passageway" is defined to be any passageway or cavity in a living organism (e.g., bile duct, bronchiole tubes, nasal cavity, blood vessels, heart, esophagus, trachea, stomach, fallopian tube, uterus, ureter, urethra, the intestines, lymphatic vessels, nasal passageways, eustachian tube, acoustic meatus, etc.). The techniques employed to deliver the medical device to a treatment area include, but are not limited to, angioplasty, vascular anastomoses, transplantation, implantation, subcutaneous introduction, minimally invasive surgical procedures, injection, topical applications, bolus administration, infusion, interventional procedures, and any combinations thereof. For vascular applications, the term "body passageway" primarily refers to blood vessels and chambers in the heart. When the medical device is in the form of a stent, the stent can be an expandable stent that is expandable by a balloon and/or other means. The stent can have many shapes and forms. Such shapes can include, but are not limited to, stents disclosed in U.S. Pat. Nos. 6,206,916 and 6,436,133; and all the prior art cited in these patents. These various designs and configurations of stents in such patents are incorporated herein by reference.

In one non-limiting aspect of the present invention, the medical device has one or more features that at least partially result in the inhibition or prevention of thrombosis after the medical device has been implanted in a treatment area. These features include, but are not limited to, 1) the shape and/or profile of the medical device, 2) the one or more materials that are used to at least partially form the medical device, and/or 3) the one or more biological agents that are at least partially coated on, contained therein and/or included in the medical device. As a result, the need or use of body-wide standard aggressive anti-platelet and/or anti-coagulation therapy for extended periods of time to inhibit or prevent the occurrence of thrombosis is not required in conjunction with the medical device of the present invention. In the past, the use of body-wide therapy was used by the patient long after the patient left the hospital or other type of medical facility. This body-wide therapy could last days, weeks, months or sometimes over a year after surgery. The medical device of the present invention can be applied or inserted into a treatment area and 1) merely require reduced use of body wide therapy after application or insertion of the medical device, or 2) does not require use of body wide therapy after application or insertion of the medical device. As such, the medical device of the present invention can be designed to be inserted in a treatment area without any temporary use and/or without extended use of body wide aggressive anti-platelet and/or anti-coagulation therapy after the medical device has been inserted in the treatment area. This method of treating a treatment area with a medical device while inhibiting or preventing the occurrence of thrombosis at or near the treatment area is a significant improvement over past treatment procedures. In one non-limiting example, no body-wide therapy is needed after the insertion of the medical device into a patient. In another and/or alternative non-limiting example, short term use of body-wide therapy is needed or used after the insertion of the medical device into a patient. Such short term use can be terminated after the release of the patient from the hospital or other type of medical facility, or one to two days or weeks after the release of the patient from the hospital or other type of medical facility; however, it will be appreciated that other time periods of body-wide therapy can be used. As a result of the use of the medical device of the present invention, the use of body-wide therapy after a medical procedure involving the insertion of a medical device into a treatment area can be significantly reduced or eliminated.

In another and/or alternative non-limiting aspect of the present invention, the medical device can include, contain and/or be coated with one or more biological agents that inhibits or prevents thrombosis during and/or after the medical device has been inserted into a treatment area. In one non-limiting embodiment, the one or more biological agents that can be include with, contained in and/or be coated on the medical device include, but are not limited to, an anti-platelet compound and/or anticoagulant compound such as, but not limited to, warfarin (Coumadin), warfarin derivatives, aspirin, aspirin derivatives, clopidogrel, clopidogrel derivatives, ticlopidine, ticlopidine derivatives, hirudin, hirudin derivatives, dipyridamole, dipyridamole derivatives, trapidil, trapidil derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, heparin, heparin derivatives, low molecular weight heparin, low molecular weight heparin derivatives, or combinations thereof. One specific non-limiting example of an anti-thrombotic inhibitor that can be include with, contained in and/or be coated on the medical device includes 1) huridin and/or derivatives, and/or 2) alagors (e.g., bivalirudin, etc.) and/or derivatives. As can be appreciated, one or more other anti-thrombotic biological agents can be used with the medical device.

In yet another and/or alternative non-limiting aspect of the present invention, the medical device can include, contain and/or be coated with one or more biological agents that facilitate in the success of the medical device and/or treated area. As indicated above, the medical device can include, contain and/or be coated with one or more biological agents that inhibit or prevent thrombosis during and/or after the medical device is inserted into a treatment area. In addition or alternatively, the medical device can include, contain and/or be coated with one or more biological agents that can be used in conjunction with the one or more biological agents that inhibit or prevent thrombosis that are included in, contained in and/or coated in the medical device. As such, the medical device, when it includes, contains and/or is coated with one or more biological agents, can include one or more biological agents that inhibit or prevent thrombosis and/or perform one or more other function(s). The term "biological agent" includes, but is not limited to, a substance, drug or otherwise formulated and/or designed to prevent, inhibit and/or treat one or more biological problems, and/or to promote the healing in a treated area. Non-limiting examples of biological problems that can be addressed by one or more biological agents include, but are not limited to, viral, fungus and/or bacteria infection; vascular diseases and/or disorders; digestive diseases and/or disorders; reproductive diseases and/or disorders; lymphatic diseases and/or disorders; cancer; implant rejection; pain; nausea; swelling; arthritis; bone diseases and/or disorders; organ failure; immunity diseases and/or disorders; cholesterol problems; blood diseases and/or disorders; lung diseases and/or disorders; heart diseases and/or disorders; brain diseases and/or disorders; neuralgia diseases and/or disorders; kidney diseases and/or disorders; ulcers; liver diseases and/or disorders; intestinal diseases and/or disorders; gallbladder diseases and/or disorders; pancreatic diseases and/or disorders; psychological disorders; respiratory diseases and/or disorders; gland diseases and/or disorders; skin diseases and/or disorders; hearing diseases and/or disorders; oral diseases and/or disorders; nasal diseases and/or disorders; eye diseases and/or disorders; fatigue; genetic diseases and/or disorders; burns; scarring and/or scars; trauma; weight diseases and/or disorders; addiction diseases and/or disorders; hair loss; cramps; muscle spasms; tissue repair; and/or the like. Non-limiting examples of biological agents that can be used include, but are not limited to, 5-Fluorouracil and/or derivatives thereof; 5-Phenylmethimazole and/or derivatives thereof; ACE inhibitors and/or derivatives thereof; acenocoumarol and/or derivatives thereof; acyclovir and/or derivatives thereof; actilyse and/or derivatives thereof; adrenocorticotropic hormone and/or derivatives thereof; adriamycin and/or derivatives thereof; agents that modulate intracellular $Ca_{2+}$ transport such as L-type (e.g., diltiazem, nifedipine, verapamil, etc.) or T-type $Ca_{2+}$ channel blockers (e.g., amiloride, etc.); alpha-adrenergic blocking agents and/or derivatives thereof; alteplase and/or derivatives thereof; amino glycosides and/or derivatives thereof (e.g., gentamycin, tobramycin, etc.); angiopeptin and/or derivatives thereof; angiostatic steroid and/or derivatives thereof; angiotensin II receptor antagonists and/or derivatives thereof; anistreplase and/or derivatives thereof; antagonists of vascular epithelial growth factor and/or derivatives thereof; anti-biotics; anticoagulant compounds and/or derivatives thereof; anti-fibrosis compounds and/or derivatives thereof; anti-fungal compounds and/or derivatives thereof; anti-inflammatory compounds and/or derivatives thereof; Anti-Invasive Factor and/or derivatives thereof; anti-metabolite compounds and/or derivatives thereof (e.g., staurosporin, trichothecenes, and modified diphtheria and ricin toxins, Pseudomonas exotoxin, etc.); anti-matrix compounds and/or derivatives thereof (e.g., colchicine, tamoxifen, etc.); anti-microbial agents and/or derivatives thereof; anti-migratory agents and/or derivatives thereof (e.g., caffeic acid derivatives, nilvadipine, etc.); antimitotic compounds and/or derivatives thereof; anti-neoplastic compounds and/or derivatives thereof; anti-oxidants and/or derivatives thereof; anti-platelet compounds and/or derivatives thereof; anti-proliferative and/or derivatives thereof; anti-thrombogenic agents and/or derivatives thereof; argatroban and/or derivatives thereof; ap-1 inhibitors and/or derivatives thereof (e.g., for tyrosine kinase, protein kinase C, myosin light chain kinase, $Ca_{2+}$/calmodulin kinase II, casein kinase II, etc.); aspirin and/or derivatives thereof; azathioprine and/or derivatives thereof; β-Estradiol and/or derivatives thereof; β-1-anticollagenase and/or derivatives thereof; calcium channel blockers and/or derivatives thereof; calmodulin antagonists and/or derivatives thereof (e.g., $H_7$, etc.); CAPTOPRIL and/or derivatives thereof; cartilage-derived inhibitor and/or derivatives thereof; ChIMP-3 and/or derivatives thereof; cephalosporin and/or derivatives thereof (e.g., cefadroxil, cefazolin, cefaclor, etc.); chloroquine and/or derivatives thereof; chemotherapeutic compounds and/or derivatives thereof (e.g., 5-fluorouracil, vincristine, vinblastine, cisplatin, doxyrubicin, adriamycin, tamocifen, etc.); chymostatin and/or derivatives thereof; CILAZAPRIL and/or derivatives thereof; clopidigrel and/or derivatives thereof; clotrimazole and/or derivatives thereof; colchicine and/or derivatives thereof; cortisone and/or derivatives thereof; coumadin and/or derivatives thereof; curacin-A and/or derivatives thereof; cyclosporine and/or derivatives thereof; cytochalasin and/or derivatives thereof (e.g., cytochalasin A, cytochalasin B, cytochalasin C, cytochalasin D, cytochalasin E, cytochalasin F, cytochalasin G, cytochalasin H, cytochalasin J, cytochalasin K, cytochalasin L, cytochalasin M, cytochalasin N, cytochalasin O, cytochalasin P, cytochalasin Q, cytochalasin R, cytochalasin S, chaetoglobosin A, chaetoglobosin B, chaetoglobosin C, chaetoglobosin D, chaetoglobosin E, chaetoglobosin F, chaetoglobosin G, chaetoglobosin J, chaetoglobosin K, deoxaphomin, proxiphomin, protophomin, zygosporin D, zygosporin E, zygosporin F, zygosporin G, aspochalasin B, aspochalasin C, aspochalasin D, etc.); cytokines and/or derivatives thereof; desirudin and/or derivatives thereof; dexamethazone and/or derivatives thereof; dipyridamole and/or derivatives thereof; eminase and/or derivatives thereof; endothelin and/or derivatives thereof; endothelial growth factor and/or derivatives thereof; epidermal growth factor and/or derivatives thereof; epothilone and/or derivatives thereof; estramustine and/or derivatives thereof; estrogen and/or derivatives thereof; fenoprofen and/or derivatives thereof; fluorouracil and/or derivatives thereof; flucytosine and/or derivatives thereof; forskolin and/or derivatives thereof; ganciclovir and/or derivatives thereof; glucocorticoids and/or derivatives thereof (e.g., dexamethasone, betamethasone, etc.); glycoprotein IIb/IIIa platelet membrane receptor antibody and/or derivatives thereof; GM-CSF and/or derivatives thereof; griseofulvin and/or derivatives thereof; growth factors and/or derivatives thereof (e.g., VEGF; TGF; IGF; PDGF; FGF, etc.); growth hormone and/or derivatives thereof; heparin and/or derivatives thereof; hirudin and/or derivatives thereof; hyaluronate and/or derivatives thereof; hydrocortisone and/or derivatives thereof; ibuprofen and/or derivatives thereof; immunosuppressive agents and/or derivatives thereof (e.g., adrenocorticosteroids, cyclosporine, etc.); indomethacin and/or derivatives thereof; inhibitors of the sodium/calcium antiporter and/or derivatives thereof (e.g., amiloride, etc.); inhibitors of the $IP_3$ receptor and/or derivatives thereof; inhibitors of the sodium/hydrogen antiporter and/or derivatives thereof (e.g., amiloride and derivatives thereof, etc.); insulin and/or derivatives thereof; Interferon alpha 2 Macroglobulin and/or derivatives thereof; ketoconazole and/or derivatives thereof; Lepirudin and/or derivatives thereof; LISINOPRIL and/or derivatives thereof; LOVASTATIN and/or derivatives thereof; marevan and/or derivatives thereof; mefloquine and/or derivatives thereof; metalloproteinase inhibitors and/or derivatives thereof; methotrexate and/or derivatives thereof; metronidazole and/or derivatives thereof; miconazole and/or derivatives thereof, monoclonal antibodies and/or derivatives thereof; mutamycin and/or derivatives thereof; naproxen and/or derivatives thereof; nitric oxide and/or derivatives thereof; nitroprusside and/or derivatives thereof; nucleic acid analogues and/or derivatives thereof (e.g., peptide nucleic acids, etc.); nystatin and/or derivatives thereof; oligonucleotides and/or derivatives thereof; paclitaxel and/or derivatives thereof; penicillin and/or derivatives thereof; pentamidine isethionate and/or derivatives thereof; phenindione and/or derivatives thereof; phenylbutazone and/or derivatives thereof; phosphodiesterase inhibitors and/or derivatives thereof; Plasminogen Activator Inhibitor-1 and/or derivatives thereof; Plasminogen Activator Inhibitor-2 and/or derivatives thereof; Platelet Factor 4 and/or derivatives thereof; platelet derived growth factor and/or derivatives thereof; plavix and/or derivatives thereof; POSTMI 75 and/or derivatives thereof; prednisone and/or derivatives thereof; prednisolone and/or derivatives thereof; probucol and/or derivatives thereof; progesterone and/or derivatives thereof; prostacyclin and/or derivatives thereof; prostaglandin inhibitors and/or derivatives thereof; protamine and/or derivatives thereof; protease and/or derivatives thereof; protein kinase inhibitors and/or derivatives thereof (e.g., staurosporin, etc.); quinine and/or derivatives thereof; radioactive agents and/or derivatives thereof (e.g., Cu-64, Ca-67, Cs-131, Ga-68, Zr-89, Ku-97, Tc-99m, Rh-105, Pd-103, Pd-109, In-111, I-123, I-125, I-131, Re-186, Re-188, Au-198, Au-199, Pb-203, At-211, Pb-212, Bi-212, $H_3P^{32}O_4$, etc.); rapamycin and/or derivatives thereof; receptor antagonists for histamine and/or derivatives thereof; refludan and/or derivatives thereof; retinoic acids and/or derivatives thereof; revasc and/or derivatives thereof; rifamycin and/or derivatives thereof; sense or anti-sense oligonucleotides and/or derivatives thereof (e.g., DNA, RNA, plasmid DNA, plasmid RNA, etc.); seramin and/or derivatives thereof; steroids; seramin and/or derivatives thereof; serotonin and/or derivatives thereof; serotonin blockers and/or derivatives thereof; streptokinase and/or derivatives thereof; sulfasalazine and/or derivatives thereof; sulfonamides and/or derivatives thereof (e.g., sulfamethoxazole, etc.); sulphated chitin derivatives; Sulphated Polysaccharide Peptidoglycan Complex and/or derivatives thereof; $T_{H1}$ and/or derivatives thereof (e.g., Interleukins-2, -12, and -15, gamma interferon, etc.); thioprotese inhibitors and/or derivatives thereof; paclitaxel and/or derivatives thereof (e.g., taxotere, baccatin, 10-dacetyltaxol, 7-xylosyl-10-deacetyltaxol, cephalomannine, 10-deacetyl-7-epitaxol, 7 epitaxol, 10-deacetylbaccatin III, 10-deacetylcephaolmannine, etc.); ticlid and/or derivatives thereof; ticlopidine and/or derivatives thereof; tick anti-coagulant peptide and/or derivatives thereof; thioprotese inhibitors and/or derivatives thereof; thyroid hormone and/or derivatives thereof; Tissue Inhibitor of Metalloproteinase-1 and/or derivatives thereof; Tissue Inhibitor of Metalloproteinase-2 and/or derivatives thereof; tissue plasma activators; TNF and/or derivatives thereof; tocopherol and/or derivatives thereof; toxins and/or derivatives thereof; tranilast and/or derivatives thereof; transforming growth factors alpha and beta and/or derivatives thereof; trapidil and/or derivatives thereof; triazolopyrimidine and/or derivatives thereof; vapiprost and/or derivatives thereof; vinblastine and/or derivatives thereof; vincristine and/or derivatives thereof; zidovudine and/or derivatives thereof. As can be appreciated, the biological agent can include one or more derivatives of the above listed compounds and/or other compounds. In one non-limiting embodiment, the biological agent includes, but is not limited to, trapidil, trapidil derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. The type and/or amount of biological agent included on, in and/or in conjunction with the medical device is generally selected for the treatment of one or more medical treatments. Typically, the amount of biological agent included on, in and/or used in conjunction with the medical device is about 0.01-100 ug per $mm^2$; however, other amounts can be used. The amount of two or more biological agents on, in and/or used in conjunction with the medical device can be the same or different. In one non-limiting example, the medical device can be coated with and/or includes one or more biological agents such as, but not limited to, trapidil and/or trapidil derivatives, paclitaxel, paclitaxel derivatives (e.g., taxotere, baccatin, 10-deacetyltaxol, 7-xylosyl-10-deacetyltaxol, cephalomannine, 10-deacetyl-7-epitaxol, 7 epitaxol, 10-deacetylbaccatin III, 10-deacetylcephaolmannine, etc.), cytochalasin, cytochalasin derivatives (e.g., cytochalasin A, cytochalasin B, cytochalasin C, cytochalasin D, cytochalasin E, cytochalasin F, cytochalasin G, cytochalasin H, cytochalasin J, cytochalasin K, cytochalasin L, cytochalasin M, cytochalasin N, cytochalasin O, cytochalasin P, cytochalasin Q, cytochalasin R, cytochalasin S, chaetoglobosin A, chaetoglobosin B, chaetoglobosin C, chaetoglobosin D, chaetoglobosin E, chaetoglobosin F, chaetoglobosin G, chaetoglobosin J, chaetoglobosin K, deoxaphomin, proxiphomin, protophomin, zygosporin D, zygosporin E, zygosporin F, zygosporin G, aspochalasin B, aspochalasin C, aspochalasin D, etc.), paclitaxel, paclitaxel derivatives, rapamycin, rapamycin derivatives, 5-Phenylmethimazole, 5-Phenylmethimazole derivatives, GM-CSF (granulo-cyte-macrophage colony-stimulating-factor), GM-CSF derivatives, or combinations thereof. In one non-limiting embodiment of the invention, the medical device can be partially or fully coated with one or more biological agents, impregnated with one or more biological agents to facilitate in the success of a particular medical procedure. The one or more biological agents can be coated on and/or impregnated in the medical device by a variety of mechanisms such as, but not limited to, spraying (e.g., atomizing spray techniques, etc.), dip coating, roll coating, sonication, brushing, plasma deposition, depositing by vapor deposition. In another and/or alternative non-limiting embodiment of the invention, the type and/or amount of biological agent included on, in and/or in conjunction with the medical device is generally selected for the treatment of one or more medical treatments. Typically the amount of biological agent included on, in and/or used in conjunction with the medical device is about 0.01-100 ug per $mm^2$; however, other amounts can be used. The amount of two or more biological agents on, in and/or used in conjunction with the medical device can be the same or different. For instance, one or more biological agents can be coated on, and/or incorporated in one or more portions of the medical device to provide local and/or systemic delivery of one or more biological agents in and/or to a body passageway to a) inhibit or prevent thrombosis, in-stent restenosis, vascular narrowing and/or restenosis after the medical device has been inserted in and/or connected to a body passageway, b) at least partially passivate, remove and/or dissolve lipids, fibroblast, fibrin, etc. in a body passageway so as to at least partially remove such materials and/or to passivate such vulnerable materials (e.g., vulnerable plaque, etc.) in the body passageway in the region of the medical device and/or down stream of the medical device. As can be appreciated, the one or more biological agents can have many other or additional uses. In another and/or alternative non-limiting example, the medical device is coated with and/or includes one or more biological agents such as, but not limited to, trapidil and/or trapidil derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. In still another and/or alternative non-limiting example, the medical device is coated with and/or includes one or more biological agents such as, but not limited to trapidil, trapidil derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof, and one or more additional biological agents, such as, but not limited to, biological agents associated with thrombolytics, vasodilators, anti-hypertensive agents, anti-microbial or anti-biotic, anti-mitotic, anti-proliferative, anti-secretory agents, non-steroidal anti-inflammatory drugs, immunosuppressive agents, growth factors and growth factor antagonists, antitumor and/or chemotherapeutic agents, anti-polymerases, anti-viral agents, anti-body targeted therapy agents, hormones, anti-oxidants, biologic components, radio-therapeutic agents, radiopaque agents and/or radio-labeled agents. In addition to these biological agents, the medical device can be coated with and/or include one or more biological agents that are capable of inhibiting or preventing any adverse biological response by and/or to the medical device that could possibly lead to device failure and/or an adverse reaction by human or animal tissue. A wide range of biological agents thus can be used.

In a further and/or alternative non-limiting aspect of the present invention, the one or more biological agents on and/or in the medical device, when used on the medical device, can be released in a controlled manner so the area in question to be treated is provided with the desired dosage of biological agent over a sustained period of time. As can be appreciated, controlled release of one or more biological agents on the medical device is not always required and/or desirable. As such, one or more of the biological agents on and/or in the medical device can be uncontrollably released from the medical device during and/or after insertion of the medical device in the treatment area. It can also be appreciated that one or more biological agents on and/or in the medical device can be controllably released from the medical device and one or more biological agents on and/or in the medical device can be uncontrollably released from the medical device. It can also be appreciated that one or more biological agents on and/or in one region of the medical device can be controllably released from the medical device and one or more biological agents on and/or in the medical device can be uncontrollably released from another region on the medical device. As such, the medical device can be designed such that 1) all of the biological agent on and/or in the medical device is controllably released, 2) some of the biological agent on and/or in the medical device is controllably released and some of the biological agent on the medical device is non-controllably released, or 3) none of the biological agent on and/or in the medical device is controllably released. The medical device can also be designed such that the rate of release of the one or more biological agents from the medical device is the same or different. The medical device can also be designed such that the rate of release of the one or more biological agents from one or more regions on the medical device is the same or different. Non-limiting arrangements that can be used to control the release of one or more biological agent from the medical device include a) at least partially coat one or more biological agents with one or more polymers, b) at least partially incorporate and/or at least partially encapsulate one or more biological agents into and/or with one or more polymers, and/or c) insert one or more biological agents in pores, passageways, cavities, etc. in the medical device and at least partially coat or cover such pores, passageways, cavities, etc. with one or more polymers. As can be appreciated, other or additional arrangements can be used to control the release of one or more biological agent from the medical device. The one or more polymers used to at least partially control the release of one or more biological agent from the medical device can be porous or non-porous. The one or more biological agents can be inserted into and/or applied to one or more surface structures and/or micro-structures on the medical device, and/or be used to at least partially form one or more surface structures and/or micro-structures on the medical device. As such, the one or more biological agents on the medical device can be 1) coated on one or more surface regions of the medical device, 2) inserted and/or impregnated in one or more surface structures and/or micro-structures, etc. of the medical device, and/or 3) form at least a portion or be included in at least a portion of the structure of the medical device. When the one or more biological agents are coated on the medical device, the one or more biological agents can 1) be directly coated on one or more surfaces of the medical device, 2) be mixed with one or more coating polymers or other coating materials and then at least partially coated on one or more surfaces of the medical device, 3) be at least partially coated on the surface of another coating material that has been at least partially coated on the medical device, and/or 4) be at least partially encapsulated between a) a surface or region of the medical device and one or more other coating materials and/or b) two or more other coating materials. As can be appreciated, many other coating arrangements can be additionally or alternatively used. When the one or more biological agents are inserted and/or impregnated in one or more internal structures, surface structures and/or micro-structures of the medical device, 1) one or more other coating materials can be applied at least partially over the one or more internal structures, surface structures and/or micro-structures of the medical device, and/or 2) one or more polymers can be combined with one or more biological agents. As such, the one or more biological agents can be 1) embedded in the structure of the medical device; 2) positioned in one or more internal structures of the medical device; 3) encapsulated between two polymer coatings; 4) encapsulated between the base structure and a polymer coating; 5) mixed in the base structure of the medical device that includes at least one polymer coating; or 6) one or more combinations of 1, 2, 3, 4 and/or 5. In addition or alternatively, the one or more coating of the one or more polymers on the medical device can include 1) one or more coatings of non-porous polymers; 2) one or more coatings of a combination of one or more porous polymers and one or more non-porous polymers; 3) one or more coating of porous polymer, or 4) one or more combinations of options 1, 2, and 3. As can be appreciated different biological agents can be located in and/or between different polymer coating layers and/or on and/or the structure of the medical device. As can also be appreciated, many other and/or additional coating combinations and/or configurations can be used. The concentration of one or more biological agents, the type of polymer, the type and/or shape of internal structures in the medical device and/or the coating thickness of one or more biological agents can be used to control the release time, the release rate and/or the dosage amount of one or more biological agents; however, other or additional combinations can be used. As such, the biological agent and polymer system combination and location on the medical device can be numerous. As can also be appreciated, one or more biological agents can be deposited on the top surface of the medical device to provide an initial burst effect of the one or more biological agents prior to 1) the control release of the one or more biological agents through one or more layers of polymer system that include one or more non-porous polymers and/or 2) the uncontrolled release of the one or more biological agents through one or more layers of polymer system. The one or more biological agents and/or polymers can be coated on the medical device by a variety of mechanisms such as, but not limited to, spraying (e.g., atomizing spray techniques, etc.), dip coating, roll coating, sonication, brushing, plasma deposition, and/or depositing by vapor deposition. The thickness of each polymer layer and/or layer of biological agent is generally at least about 0.01 µm and is generally less than about 150 µm. In one non-limiting embodiment, the thickness of a polymer layer and/or layer of biological agent is about 0.02-75 µm, more particularly about 0.05-50 µm, and even more particularly about 1-30 µm. When the medical device includes and/or is coated with one or more biological agents such that at least one of the biological agents is at least partially controllably released from the medical device, the need or use of body-wide therapy for extended periods of time can be reduced or eliminated. In the past, the use of body-wide therapy was used by the patient long after the patient left the hospital or other type of medical facility. This body-wide therapy could last days, weeks, months or sometimes over a year after surgery. The medical device of the present invention can be applied or inserted into a treatment area and 1) merely requires reduced use and/or extended use of body wide therapy after application or insertion of the medical device or 2) does not require use and/or extended use of body wide therapy after application or insertion of the medical device. As can be appreciated, use and/or extended use of body wide therapy can be used after application or insertion of the medical device at the treatment area. In one non-limiting example, no body-wide therapy is needed after the insertion of the medical device into a patient. In another and/or alternative non-limiting example, short term use of body-wide therapy is needed or used after the insertion of the medical device into a patient. Such short term use can be terminated after the release of the patient from the hospital or other type of medical facility, or one to two days or weeks after the release of the patient from the hospital or other type of medical facility; however, it will be appreciated that other time periods of body-wide therapy can be used. As a result of the use of the medical device of the present invention, the use of body-wide therapy after a medical procedure involving the insertion of a medical device into a treatment area can be significantly reduced or eliminated.

In another and/or alternative non-limiting aspect of the present invention, controlled release of one or more biological agents from the medical device, when controlled release is desired, can be accomplished by using one or more non-porous polymer layers; however, other and/or additional mechanisms can be used to controllably release the one or more biological agents. The one or more biological agents are at least partially controllably released by molecular diffusion through the one or more non-porous polymer layers. When one or more non-porous polymer layers are used, the one or more polymer layers are typically biocompatible polymers; however, this is not required. The one or more non-porous polymers can be applied to the medical device without the use of chemical, solvents, and/or catalysts; however, this is not required. In one non-limiting example, the non-porous polymer can be at least partially applied by, but not limited to, vapor deposition and/or plasma deposition. The non-porous polymer can be selected so as to polymerize and cure merely upon condensation from the vapor phase; however, this is not required. The application of the one or more non-porous polymer layers can be accomplished without increasing the temperature above ambient temperature (e.g., 65-90° F.); however, this is not required. The non-porous polymer system can be mixed with one or more biological agents prior to being coated on the medical device and/or be coated on a medical device that previously included one or more biological agents; however, this is not required. The use of one or more non-porous polymer layers allow for accurate controlled release of the biological agent from the medical device. The controlled release of one or more biological agents through the non-porous polymer is at least partially controlled on a molecular level utilizing the motility of diffusion of the biological agent through the non-porous polymer. In one non-limiting example, the one or more non-porous polymer layers can include, but are not limited to, polyamide, parylene (e.g., parylene C, parylene N) and/or a parylene derivative.

In still another and/or alternative non-limiting aspect of the present invention, controlled release of one or more biological agents from the medical device, when controlled release is desired, can be accomplished by using one or more polymers that form a chemical bond with one or more biological agents. In one non-limiting example, at least one biological agent includes trapidil, trapidil derivative or a salt thereof that is covalently bonded to at least one polymer such as, but not limited to, an ethylene-acrylic acid copolymer. The ethylene is the hydrophobic group and acrylic acid is the hydrophilic group. The mole ratio of the ethylene to the acrylic acid in the copolymer can be used to control the hydrophobicity of the copolymer. The degree of hydrophobicity of one or more polymers can be also be used to control the release rate of one or more biological agents from the one or more polymers. The amount of biological agent that can be loaded with one or more polymers may be a function of the concentration of anionic groups and/or cationic groups in the one or more polymer. For biological agents that are anionic, the concentration of biological agent that can be loaded on the one or more polymers is generally a function of the concentration of cationic groups (e.g. amine groups and the like) in the one or more polymer and the fraction of these cationic groups that can ionically bind to the anionic form of the one or more biological agents. For biological agents that are cationic (e.g., trapidil, etc.), the concentration of biological agent that can be loaded on the one or more polymers is generally a function of the concentration of anionic groups (i.e., carboxylate groups, phosphate groups, sulfate groups, and/or other organic anionic groups) in the one or more polymers, and the fraction of these anionic groups that can ionically bind to the cationic form of the one or more biological agents. As such, the concentration of one or more biological agent that can be bound to the one or more polymers can be varied by controlling the amount of hydrophobic and hydrophilic monomer in the one or more polymers, by controlling the efficiency of salt formation between the biological agent, and/or the anionic/cationic groups in the one or more polymers.

In still another and/or alternative non-limiting aspect of the present invention, controlled release of one or more biological agents from the medical device, when controlled release is desired, can be accomplished by using one or more polymers that include one or more induced cross-links. These one or more cross-links can be used to at least partially control the rate of release of the one or more biological agents from the one or more polymers. The cross-linking in the one or more polymers can be instituted by a number to techniques such as, but not limited to, using catalysts, using radiation, using heat, and/or the like. The one or more cross-links formed in the one or more polymers can result in the one or more biological agents to become partially or fully entrapped within the cross-linking, and/or form a bond with the cross-linking. As such, the partially or fully biological agent takes longer to release itself from the cross-linking, thereby delaying the release rate of the one or more biological agents from the one or more polymers. Consequently, the amount of biological agent, and/or the rate at which the biological agent is released from the medical device over time can be at least partially controlled by the amount or degree of cross-linking in the one or more polymers.

In still a further and/or alternative aspect of the present invention, a variety of polymers can be coated on the medical device and/or be used to form at least a portion of the medical device. The one or more polymers can be used on the medical for a variety of reasons such as, but not limited to, 1) forming a portion of the medical device, 2) improving a physical property of the medical device (e.g., improve strength, improve durability, improve bio-compatibility, reduce friction, etc.), 3) forming a protective coating on one or more surface structures on the medical device, 4) at least partially forming one or more surface structures on the medical device, and/or 5) at least partially controlling a release rate of one or more biological agents from the medical device. As can be appreciated, the one or more polymers can have other or additional uses on the medical device. The one or more polymers can be porous, non-porous, biostable, biodegradable (i.e., dissolves, degrades, is absorbed, or any combination thereof in the body), and/or biocompatible. When the medical device is coated with one or more polymers, the polymer can include 1) one or more coatings of non-porous polymers; 2) one or more coatings of a combination of one or more porous polymers and one or more non-porous polymers; 3) one or more coatings of one or more porous polymers and one or more coatings of one or more non-porous polymers; 4) one or more coating of porous polymer, or 5) one or more combinations of options 1, 2, 3 and 4. The thickness of one or more of the polymer layers can be the same or different. When one or more layers of polymer are coated onto at least a portion of the medical device, the one or more coatings can be applied by a variety of techniques such as, but not limited to, vapor deposition and/or plasma deposition, spraying, dip-coating, roll coating, sonication, atomization, brushing and/or the like; however, other or additional coating techniques can be used. The one or more polymers that can be coated on the medical device and/or used to at least partially form the medical device can be polymers that considered to be biodegradable, bioresorbable, or bioerodable; polymers that are considered to be biostable; and/or polymers that can be made to be biodegradable and/or bioresorbable with modification. Non-limiting examples of polymers that are considered to be biodegradable, bioresorbable, or bioerodable include, but are not limited to, aliphatic polyesters; poly(glycolic acid) and/or copolymers thereof (e.g., poly(glycolide trimethylene carbonate); poly(caprolactone glycolide)); poly(lactic acid) and/or isomers thereof (e.g., poly-L(lactic acid) and/or poly-D Lactic acid) and/or copolymers thereof (e.g. DL-PLA), with and without additives (e.g. calcium phosphate glass), and/or other copolymers (e.g. poly(caprolactone lactide), poly(lactide glycolide), poly(lactic acid ethylene glycol)); poly(ethylene glycol); poly(ethylene glycol) diacrylate; poly(lactide); polyalkylene succinate; polybutylene diglycolate; polyhydroxybutyrate (PHB); polyhydroxyvalerate (PHV); polyhydroxybutyrate/polyhydroxyvalerate copolymer (PHB/PHV); poly(hydroxybutyrate-co-valerate); polyhydroxyalkaoates (PHA); polycaprolactone; poly(caprolactone-polyethylene glycol) copolymer; poly(valerolactone); polyanhydrides; poly(orthoesters) and/or blends with polyanhydrides; poly(anhydride-co-imide); polycarbonates (aliphatic); poly(hydroxyl-esters); polydioxanone; polyanhydrides; polyanhydride esters; polycyanoacrylates; poly(alkyl 2-cyanoacrylates); poly(amino acids); poly(phosphazenes); poly(propylene fumarate); poly(propylene fumarate-co-ethylene glycol); poly(fumarate anhydrides); fibrinogen; fibrin; gelatin; cellulose and/or cellulose derivatives and/or cellulosic polymers (e.g., cellulose acetate, cellulose acetate butyrate, cellulose butyrate, cellulose ethers, cellulose nitrate, cellulose propionate, cellophane); chitosan and/or chitosan derivatives (e.g., chitosan NOCC, chitosan NOOC-G); alginate; polysaccharides; starch; amylase; collagen; polycarboxylic acids; poly(ethyl ester-co-carboxylate carbonate) (and/or other tyrosine derived polycarbonates); poly (iminocarbonate); poly(BPA-iminocarbonate); poly(trimethylene carbonate); poly(iminocarbonate-amide) copolymers and/or other pseudo-poly(amino acids); poly(ethylene glycol); poly(ethylene oxide); poly(ethylene oxide)/poly(butylene terephthalate) copolymer; poly(epsilon-caprolactone-dimethyltrimethylene carbonate); poly(ester amide); poly (amino acids) and conventional synthetic polymers thereof; poly(alkylene oxalates); poly(alkylcarbonate); poly(adipic anhydride); nylon copolyamides; NO-carboxymethyl chitosan NOCC); carboxymethyl cellulose; copoly(ether-esters) (e.g., PEO/PLA dextrans); polyketals; biodegradable polyethers; biodegradable polyesters; polydihydropyrans; polydepsipeptides; polyarylates (L-tyrosine-derived) and/or free acid polyarylates; polyamides (e.g., Nylon 66, polycaprolactam); poly(propylene fumarate-co-ethylene glycol) (e.g., fumarate anhydrides); hyaluronates; poly-p-dioxanone; polypeptides and proteins; polyphosphoester; polyphosphoester urethane; polysaccharides; pseudo-poly(amino acids); starch; terpolymer; (copolymers of glycolide, lactide, or dimethyltrimethylene carbonate); rayon; rayon triacetate; latex; and/pr copolymers, blends, and/or composites of above. Non-limiting examples of polymers that considered to be biostable include, but are not limited to, parylene; parylene c; parylene f; parylene n; parylene derivatives; maleic anyhydride polymers; phosphorylcholine; poly n-butyl methacrylate (PBMA); polyethylene-co-vinyl acetate (PEVA); PBMA/PEVA blend or copolymer; polytetrafluoroethene (Teflon®) and derivatives; poly-paraphenylene terephthalamide (Kevlar®); poly(ether ether ketone) (PEEK); poly(styrene-b-isobutylene-b-styrene) (Translute™); tetramethyldisiloxane (side chain or copolymer); polyimides polysulfides; poly(ethylene terephthalate); poly(methyl methacrylate); poly(ethylene-co-methyl methacrylate); styrene-ethylene/butylene-styrene block copolymers; ABS; SAN; acrylic polymers and/or copolymers (e.g., n-butyl-acrylate, n-butyl methacrylate, 2-ethylhexyl acrylate, lauryl-acrylate, 2-hydroxy-propyl acrylate, polyhydroxyethyl, methacrylate/methylmethacrylate copolymers); glycosaminoglycans; alkyd resins; elastin; polyether sulfones; epoxy resin; poly(oxymethylene); polyolefins; polymers of silicone; polymers of methane; polyisobutylene; ethylene-alphaolefin copolymers; polyethylene; polyacrylonitrile; fluorosilicones; poly(propylene oxide); polyvinyl aromatics (e.g. polystyrene); poly(vinyl ethers) (e.g. polyvinyl methyl ether); poly(vinyl ketones); poly(vinylidene halides) (e.g. polyvinylidene fluoride, polyvinylidene chloride); poly(vinylpyrolidone); poly(vinylpyrolidone)/vinyl acetate copolymer; polyvinylpridine prolastin or silk-elastin polymers (SELP); silicone; silicone rubber; polyurethanes (polycarbonate polyurethanes, silicone urethane polymer) (e.g., chronoflex varieties, bionate varieties); vinyl halide polymers and/or copolymers (e.g. polyvinyl chloride); polyacrylic acid; ethylene acrylic acid copolymer; ethylene vinyl acetate copolymer; polyvinyl alcohol; poly(hydroxyl alkylmethacrylate); Polyvinyl esters (e.g. polyvinyl acetate); and/or copolymers, blends, and/or composites of above. Non-limiting examples of polymers that can be made to be biodegradable and/or bioresorbable with modification include, but are not limited to, hyaluronic acid (hyanluron); polycarbonates; polyorthocarbonates; copolymers of vinyl monomers; polyacetals; biodegradable polyurethanes; polyacrylamide; polyisocyanates; polyamide; and/or copolymers, blends, and/or composites of above. As can be appreciated, other and/or additional polymers and/or derivatives of one or more of the above listed polymers can be used. The one or more polymers can be coated on the medical device by a variety of mechanisms such as, but not limited to, spraying (e.g., atomizing spray techniques, etc.), dip coating, roll coating, sonication, brushing, plasma deposition, and/or depositing by vapor deposition. The thickness of each polymer layer is generally at least about 0.01 µm and is generally less than about 150 µm; however, other thicknesses can be used. In one non-limiting embodiment, the thickness of a polymer layer and/or layer of biological agent is about 0.02-75 µm, more particularly about 0.05-50 µm, and even more particularly about 1-30 µm. As can be appreciated, other thicknesses can be used. In one non-limiting embodiment, the medical device includes and/or is coated with parylene, PLGA, POE, PGA, PLLA, PAA, PEG, chitosan and/or derivatives of one or more of these polymers. In another and/or alternative non-limiting embodiment, the medical device includes and/or is coated with a non-porous polymer that includes, but is not limited to, polyamide, parylene c, parylene n and/or a parylene derivative. In still another and/or alternative non-limiting embodiment, the medical device includes and/or is coated with poly(ethylene oxide), poly(ethylene glycol), and poly(propylene oxide), polymers of silicone, methane, tetrafluoroethylene (including TEFLON brand polymers), tetramethyldisiloxane, and the like.

In another and/or alternative non-limiting aspect of the present invention, the medical device, when including and/or is coated with one or more biological agents, can include and/or can be coated with one or more biological agents that are the same or different in different regions of the medical device and/or have differing amounts and/or concentrations in differing regions of the medical device. For instance, the medical device can a) be coated with and/or include one or more biologicals on at least one portion of the medical device and at least another portion of the medical device is not coated with and/or includes biological agent; b) be coated with and/or include one or more biologicals on at least one portion of the medical device that is different from one or more biologicals on at least another portion of the medical device; c) be coated with and/or include one or more biologicals at a concentration on at least one portion of the medical device that is different from the concentration of one or more biologicals on at least another portion of the medical device; etc.

In still another and/or alternative non-limiting aspect of the present invention, one or more surfaces of the medical device can be treated to achieve the desired coating properties of the one or more biological agents and one or more polymers coated on the medical device. Such surface treatment techniques include, but are not limited to, cleaning, buffing, smoothing, etching (chemical etching, plasma etching, etc.), etc. When an etching process is used, various gasses can be used for such a surface treatment process such as, but not limited to, carbon dioxide, nitrogen, oxygen, Freon, helium, hydrogen, etc. The plasma etching process can be used to clean the surface of the medical device, change the surface properties of the medical device so as to affect the adhesion properties, lubricity properties, etc. of the surface of the medical device. As can be appreciated, other or additional surface treatment processes can be used prior to the coating of one or more biological agents and/or polymers on the surface of the medical device. In one non-limiting manufacturing process, one or more portions of the medical device are cleaned and/or plasma etched; however, this is not required. Plasma etching can be used to clean the surface of the medical device, and/or to form one or more non-smooth surfaces on the medical device to facilitate in the adhesion of one or more coatings of biological agents and/or one or more coatings of polymer on the medical device. The gas for the plasma etching can include carbon dioxide and/or other gasses. Once one or more surface regions of the medical device have been treated, one or more coatings of polymer and/or biological agent can be applied to one or more regions of the medical device. For instance, 1) one or more layers of porous or non-porous polymer can be coated on an outer and/or inner surface of the medical device, 2) one or more layers of biological agent can be coated on an outer and/or inner surface of the medical device, or 3) one or more layers of porous or non-porous polymer that includes one or more biological agents can be coated on an outer and/or inner surface of the medical device. The one or more layers of biological agent can be applied to the medical device by a variety of techniques (e.g., dipping, rolling, brushing, spraying, particle atomization, etc.). One non-limiting coating technique is by an ultrasonic mist coating process wherein ultrasonic waves are used to break up the droplet of biological agent and form a mist of very fine droplets. These fine droplets have an average droplet diameter of about 0.1-3 microns. The fine droplet mist facilitates in the formation of a uniform coating thickness and can increase the coverage area on the medical device.

In still yet another and/or alternative non-limiting aspect of the present invention, one or more portions of the medical device can 1) include the same or different biological agents, 2) include the same or different amount of one or more biological agents, 3) include the same or different polymer coatings, 4) include the same or different coating thicknesses of one or more polymer coatings, 5) have one or more portions of the medical device controllably release and/or uncontrollably release one or more biological agents, and/or 6) have one or more portions of the medical device controllably release one or more biological agents and one or more portions of the medical device uncontrollably release one or more biological agents.

In yet another and/or alternative non-limiting aspect of the invention, the medical device can include a marker material that facilitates enabling the medical device to be properly positioned in a body passageway. The marker material is typically designed to be visible to electromagnetic waves (e.g., x-rays, microwaves, visible light, inferred waves, ultraviolet waves, etc.); sound waves (e.g., ultrasound waves, etc.); magnetic waves (e.g., MRI, etc.); and/or other types of electromagnetic waves (e.g., microwaves, visible light, inferred waves, ultraviolet waves, etc.). In one non-limiting embodiment, the marker material is visible to x-rays (i.e., radiopaque). The marker material can form all or a portion of the medical device and/or be coated on one or more portions (flaring portion and/or body portion; at ends of medical device; at or near transition of body portion and flaring section; etc.) of the medical device. The location of the marker material can be on one or multiple locations on the medical device. The size of the one or more regions that include the marker material can be the same or different. The marker material can be spaced at defined distances from one another so as to form ruler like markings on the medical device to facilitate in the positioning of the medical device in a body passageway. The marker material can be a rigid or flexible material. The marker material can be a biostable or biodegradable material. When the marker material is a rigid material, the marker material is typically formed of a metal material (e.g., metal band, metal plating, etc.); however, other or additional materials can be used. The metal which at least partially forms the medical device can function as a marker material; however, this is not required. When the marker material is a flexible material, the marker material typically is formed of one or more polymers that are marker materials in-of-themselves and/or include one or more metal powders and/or metal compounds. In one non-limiting embodiment, the flexible marker material includes one or more metal powders in combinations with parylene, PLGA, POE, PGA, PLLA, PAA, PEG, chitosan and/or derivatives of one or more of these polymers. In another and/or alternative non-limiting embodiment, the flexible marker material includes one or more metals and/or metal powders of aluminum, barium, bismuth, cobalt, copper, chromium, gold, iron, stainless steel, titanium, vanadium, nickel, zirconium, niobium, lead, molybdenum, platinum, yttrium, calcium, rare earth metals, rhenium, zinc, silver, depleted radioactive elements, tantalum and/or tungsten; and/or compounds thereof. The marker material can be coated with a polymer protective material; however, this is not required. When the marker material is coated with a polymer protective material, the polymer coating can be used to 1) at least partially insulate the marker material from body fluids, 2) facilitate in retaining the marker material on the medical device, 3) at least partially shielding the marker material from damage during a medical procedure and/or 4) provide a desired surface profile on the medical device. As can be appreciated, the polymer coating can have other or additional uses. The polymer protective coating can be a biostable polymer or a biodegradable polymer (e.g., degrades and/or is absorbed). The coating thickness of the protective coating polymer material, when used, is typically less than about 300 microns; however, other thickness can be used. In one non-limiting embodiment, the protective coating materials include parylene, PLGA, POE, PGA, PLLA, PAA, PEG, chitosan and/or derivatives of one or more of these polymers.

In still another and/or alternative aspect of the invention, the medical device can be an expandable device that can be expanded by use of another device (e.g., balloon, etc.) and/or is self expanding. The expandable medical device can be fabricated from a material that has no or substantially no shape memory characteristics or can be fabricated from a material having shape-memory characteristics.

In a further and/or alternative non-limiting aspect of the present invention, the medical device or one or more regions of the medical device can be constructed by use of one or more microelectromechanical manufacturing techniques (MEMS (e.g., micro-machining, laser micro-machining, laser micro-machining, micro-molding, etc.); however, other or additional manufacturing techniques can be used. The medical device can include one or more surface structures (e.g., pore, channel, pit, rib, slot, notch, bump, teeth, well, hole, groove, etc.). These structures can be at least partially formed by MEMS (e.g., micro-machining, etc.) technology and/or other types of technology. The medical device can include one or more micro-structures (e.g., micro-needle, micro-pore, micro-cylinder, micro-cone, micro-pyramid, micro-tube, micro-parallelopiped, micro-prism, micro-hemisphere, teeth, rib, ridge, ratchet, hinge, zipper, zip-tie like structure, etc.) on the surface of the medical device. Non-limiting examples of structures that can be formed on the medical devices such as stents are illustrated in United States Patent Publication Nos. 2004/0093076 and 2004/0093077, which are incorporated herein by reference. Typically, the micro-structures, when formed, extend from or into the outer surface no more than about 400 microns, and more typically less than about 300 microns, and more typically about 15-250 microns; however, other sizes can be used. The micro-structures can be clustered together or disbursed throughout the surface of the medical device. Similar shaped and/or sized micro-structures and/or surface structures can be used, or different shaped and/or sized micro-structures can be used. When one or more surface structures and/or micro-structures are designed to extend from the surface of the medical device, the one or more surface structures and/or micro-structures can be formed in the extended position and/or be designed so as to extend from the medical device during and/or after deployment of the medical device in a treatment area. The micro-structures and/or surface structures can be designed to contain and/or be fluidly connected to a passageway, cavity, etc.; however, this is not required. The one or more surface structures and/or micro-structures can be used to engage and/or penetrate surrounding tissue or organs once the medical device has be position on and/or in a patient; however, this is not required. The one or more surface structures and/or micro-structures can be used to facilitate in forming maintaining a shape of a medical device (i.e., see devices in United States Patent Publication Nos. 2004/0093076 and 2004/0093077). The one or more surface structures and/or micro-structures can be at least partially formed by MEMS (e.g., micro-machining, laser micro-machining, micro-molding, etc.) technology; however, this is not required. In one non-limiting embodiment, the one or more surface structures and/or micro-structures can be at least partially formed of a biological agent and/or be formed of a polymer. One or more of the surface structures and/or micro-structures can include one or more internal passageways that can include one or more materials (e.g., biological agent, polymer, etc.); however, this is not required. The one or more surface structures and/or micro-structures can be formed by a variety of processes (e.g., machining, chemical modifications, chemical reactions, MEMS (e.g., micro-machining, etc.), etching, laser cutting, etc.). The one or more coatings and/or one or more surface structures and/or micro-structures of the medical device can be used for a variety of purposes such as, but not limited to, 1) increasing the bonding and/or adhesion of one or more biological agents, adhesives, marker materials and/or polymers to the medical device, 2) changing the appearance or surface characteristics of the medical device, and/or 3) controlling the release rate of one or more biological agents. The one or more micro-structures and/or surface structures can be biostable, biodegradable, bioabsorbable, etc. One or more regions of the medical device that are at least partially formed by microelectromechanical manufacturing techniques can be biostable, biodegradable, bioabsorbable, etc. The medical device or one or more regions of the medical device can be at least partially covered and/or filled with a protective material so to at least partially protect one or more regions of the medical device, and/or one or more micro-structures and/or surface structures on the medical device from damage. One or more regions of the medical device, and/or one or more micro-structures and/or surface structures on the medical device can be damaged when the medical device is 1) packaged and/or stored, 2) unpackaged, 3) connected to and/or other secured and/or placed on another medical device, 4) inserted into a treatment area, 5) handled by a user, and/or 6) form a barrier between one or more micro-structures and/or surface structures and fluids in the body passageway. As can be appreciated, the medical device can be damaged in other or additional ways. The protective material can be used to protect the medical device and one or more micro-structures and/or surface structures from such damage. The protective material can include one or more polymers previously identified above. The protective material can be 1) biostable and/or biodegradable and/or 2) porous and/or non-porous. In one non-limiting design, the polymer is at least partially biodegradable so as to at least partially exposed one or more micro-structure and/or surface structure to the environment after the medical device has been at least partially inserted into a treatment area. In another and/or additional non-limiting design, the protective material includes, but is not limited to, sugar (e.g., glucose, fructose, sucrose, etc.), carbohydrate compound, salt (e.g., NaCl, etc.), parylene, PLGA, POE, PGA, PLLA, PAA, PEG, chitosan and/or derivatives of one or more of these materials; however, other and/or additional materials can be used. In still another and/or additional non-limiting design, the thickness of the protective material is generally less than about 300 microns, and typically less than about 150 microns; however, other thicknesses can be used. The protective material can be coated by one or more mechanisms previously described herein.

In still yet another and/or alternative non-limiting aspect of the present invention, the medical device can include and/or be used with a physical hindrance. The physical hindrance can include, but is not limited to, an adhesive, a sheath, a magnet, tape, wire, string, etc. The physical hindrance can be used to 1) physically retain one or more regions of the medical device in a particular form or profile, 2) physically retain the medical device on a particular deployment device, 3) protect one or more surface structures and/or micro-structures on the medical device, and/or 4) form a barrier between one or more surface regions, surface structures and/or micro-structures on the medical device and the fluids in a body passageway. As can be appreciated, the physical hindrance can have other and/or additional functions. The physical hindrance is typically a biodegradable material; however, a biostable material can be used. The physical hindrance can be designed to withstand sterilization of the medical device; however, this is not required. The physical hindrance can be applied to, included in and/or be used in conjunction with one or more medical devices. Additionally or alternatively, the physical hindrance can be designed to be used with and/or conjunction with a medical device for a limited period of time and then 1) disengage from the medical device after the medical device has been partially or fully deployed and/or 2) dissolve and/or degrade during and/or after the medical device has been partially or fully deployed; however, this is not required. Additionally or alternatively, the physical hindrance can be designed and be formulated to be temporarily used with a medical device to facilitate in the deployment of the medical device; however, this is not required. In one non-limiting use of the physical hindrance, the physical hindrance is designed or formulated to at least partially secure a medical device to another device that is used to at least partially transport the medical device to a location for treatment. In another and/or alternative non-limiting use of the physical hindrance, the physical hindrance is designed or formulated to at least partially maintain the medical device in a particular shape or form until the medical device is at least partially positioned in a treatment location. In still another and/or alternative non-limiting use of the physical hindrance, the physical hindrance is designed or formulated to at least partially maintain and/or secure one type of medical device to another type of medical instrument or device until the medical device is at least partially positioned in a treatment location. The physical hindrance can also or alternatively be designed and formulated to be used with a medical device to facilitate in the use of the medical device. In one non-limiting use of the physical hindrance, when in the form of an adhesive, can be formulated to at least partially secure a medical device to a treatment area so as to facilitate in maintaining the medical device at the treatment area. For instance, the physical hindrance can be used in such use to facilitate in maintaining a medical device on or at a treatment area until the medical device is properly secured to the treatment area by sutures, stitches, screws, nails, rod, etc; however, this is not required. Additionally or alternatively, the physical hindrance can be used to facilitate in maintaining a medical device on or at a treatment area until the medical device has partially or fully accomplished its objective. The physical hindrance is typically a biocompatible material so as to not cause unanticipated adverse effects when properly used. The physical hindrance can be biostable or biodegradable (e.g., degrades and/or is absorbed, etc.).

When the physical hindrance includes or is one or more adhesives, the one or more adhesives can be applied to the medical device by, but is not limited to, spraying (e.g., atomizing spray techniques, etc.), dip coating, roll coating, sonication, brushing, plasma deposition, and/or depositing by vapor deposition, brushing, painting, etc.) on the medical device. The physical hindrance can also or alternatively form at least a part of the medical device. One or more regions and/or surfaces of a medical device can also or alternatively include the physical hindrance. The physical hindrance can include one or more biological agents and/or other materials (e.g., marker material, polymer, etc.); however, this is not required. When the physical hindrance is or includes an adhesive, the adhesive can be formulated to controllably release one or more biological agents in the adhesive and/or coated on and/or contained within the medical device; however, this is not required. The adhesive can also or alternatively control the release of one or more biological agents located on and/or contained in the medical device by forming a penetrable or non-penetrable barrier to such biological agents; however, this is not required. The adhesive can include and/or be mixed with one or more polymers; however, this is not required. The one or more polymers can be used to 1) control the time of adhesion provided by said adhesive, 2) control the rate of degradation of the adhesive, and/or 3) control the rate of release of one or more biological agents from the adhesive and/or diffusing or penetrating through the adhesive layer; however, this is not required. When the physical hindrance includes a sheath, the sheath can be designed to partially or fully encircle the medical device. The sheath can be designed to be physically removed from the medical device after the medical device is deployed to a treatment area; however, this is not required. The sheath can be formed of a biodegradable material that at least partially degrades overtime to at least partially expose one or more surface regions, micro-structures and/or surface structures of the medical device; however, this is not required. The sheath can include and/or be at least partially coated with one or more biological agents. The sheath include one or more polymers; however, this is not required. The one or more polymers can be used for a variety of reasons such as, but not limited to, 1) forming a portion of the sheath, 2) improving a physical property of the sheath (e.g., improve strength, improve durability, improve biocompatibility, reduce friction, etc.), and/or 3 at least partially controlling a release rate of one or more biological agents from the sheath. As can be appreciated, the one or more polymers can have other or additional uses on the sheath.

In still a further and/or alternative non-limiting aspect of the present invention, the medical device can be fully or partially formed of a base material that has biostable or bioabsorbable properties. The medical device can be at least partially formed of one or more polymers, biological agents, metals (e.g., aluminum, barium, bismuth, calcium, carbon, cobalt, copper, chromium, depleted radioactive elements, gold, iron, lead, molybdenum, magnesium, nickel, niobium, platinum, rare earth metals, rhenium, silver, tantalum, titanium, tungsten, vanadium, yttrium, zinc, zirconium, and/or alloys thereof (e.g., stainless steel, nitinol, Cr—Co, Mo—Re, Ta—W, Mg—Zr, Mg—Zn, brass, etc.)), ceramics, and/or fiber reinforced materials (e.g., carbon fiber material, fiberglass, etc.). The medical device generally includes one or more materials that impart the desired properties to the medical device so as to withstand the manufacturing process that is needed to produce the medical device. These manufacturing processes can include, but are not limited to, laser cutting, etching, grinding, water cutting, spark erosion, crimping, annealing, drawing, pilgering, electroplating, electro-polishing, chemical polishing, ion beam deposition or implantation, sputter coating, vacuum deposition, etc.

In still a further and/or alternative non-limiting aspect of the present invention, the medical device can be fully or partially formed of a base material that is at least partially made of a novel metal alloy having improved properties as compared to past medical devices that were form of stainless steel, or cobalt-chromium alloys. The novel metal alloy used to at least partially form the medical device can improve one or more properties (e.g., strength, durability, hardness, biostability, bendability, coefficient of friction, radial strength, flexibility, tensile strength, longitudinal lengthening, stress-strain properties, improved recoil properties, radiopacity, heat sensitivity, biocompatibility, etc.) of such medical device. These one or more physical properties of the novel metal alloy can be achieved in the medical device without increasing the bulk, volume or weight of the medical device, and in some instances can be obtained even when the volume, bulk and/or weight of the medical device is reduced as compared to medical devices that are at least partially formed from traditional stainless steel or cobalt and chromium alloy materials. The novel metal alloy that is used to at least partially form the medical device can thus 1) increase the radiopacity of the medical device, 2) increase the radial strength of the medical device, 3) increase the tensile strength of the medical device, 4) improve the stress-strain properties of the medical device, 5) improve the crimping and/or expansion properties of the medical device, 6) improve the bendability and/or flexibility of the medical device, 7) improve the strength and/or durability of the medical device, 8) increase the hardness of the medical device, 9) improve the longitudinal lengthening properties of the medical device, 10) improved recoil properties of the medical device, 11) improve the friction coefficient of the medical device, 12) improve the heat sensitivity properties of the medical device, 13) improve the biostability and/or biocompatibility properties of the medical device, and/or 14) enable smaller, thinner and/or lighter weight medical devices to be made. It is believed that a smaller, thinner and/or lighter weight medical device such as, but not limited to a stent, can be inserted in a body passageway and result in a decreased incidence of thrombosis. It is believed that such a medical device will result in a less adverse response by the body when the medical device is inserted in the body passageway. As such, the medical device can be used without any biological agent included in, contained in, and/or coated on the medical device and still result in a reduction in the incidence of thrombosis. As such, the need for extended use of body wide aggressive anti-platelet and/or anti-coagulation therapy after the medical device has been inserted in the treatment area can be reduced or eliminated by use of the novel alloy.

In a further and/or alternative one non-limiting aspect of the invention, the novel metal alloy that is used to form all or a portion of the medical device includes rhenium and molybdenum. The novel alloy can include one or more other metals such as, but not limited to, calcium, chromium, cobalt, copper, gold, iron, lead, magnesium, nickel, niobium, platinum, rare earth metals, silver, tantalum, titanium, tungsten, yttrium, zinc, zirconium, and/or alloys thereof. In one non-limiting embodiment of the invention, the novel metal alloy that is used to form all or a portion of the medical device is a novel metal alloy that includes at least about 90 weight percent molybdenum and rhenium. In one non-limiting composition, the content of molybdenum and rhenium in the novel metal alloy is at least about 95 weight percent. In another and/or alternative non-limiting composition, the content of molybdenum and rhenium in the novel metal alloy is at least about 97 weight percent. In still another and/or alternative non-limiting composition, the content of molybdenum and rhenium in the novel metal alloy is at least about 98 weight percent. In yet another and/or alternative non-limiting composition, the content of molybdenum and rhenium in the novel metal alloy is at least about 99 weight percent. In still yet another and/or alternative non-limiting composition, the content of molybdenum and rhenium in the novel metal alloy is at least about 99.5 weight percent. In a further one non-limiting composition, the content of molybdenum and rhenium in the novel metal alloy is at least about 99.9 weight percent. In still a further and/or alternative non-limiting composition, the content of molybdenum and rhenium in the novel metal alloy is at least about 99.95 weight percent. In yet a further and/or alternative non-limiting composition, the content of molybdenum and rhenium in the novel metal alloy is at least about 99.99 weight percent. As can be appreciated, other weight percentages of the rhenium and molybdenum content of the novel metal alloy can be used. In one non-limiting composition, the purity level of the novel metal alloy is such so as to produce a solid solution of the novel metal alloy. A solid solution or homogeneous solution is defined as a metal alloy that includes two or more primary metals and the combined weight percent of the primary metals is at least about 95 weight percent, typically at least about 99 weight percent, more typically at least about 99.5 weight percent, even more typically at least about 99.8 weight percent, and still even more typically at least about 99.9 weight percent. A primary metal is a metal component of the metal alloy that is not a metal impurity. A solid solution of a novel metal alloy that includes rhenium and molybdenum as the primary metals is an alloy that includes at least about 95-99 weight percent rhenium and molybdenum. It is believed that a purity level of less than 95 weight percent molybdenum and rhenium adversely affects one or more physical properties of the metal alloy that are useful or desired in forming and/or using a medical device. In one embodiment of the invention, the rhenium content of the novel metal alloy in accordance with the present invention is at least about 40 weight percent. In one non-limiting composition, the rhenium content of the novel metal alloy is at least about 45 weight percent. In still another and/or alternative non-limiting composition, the rhenium content of the novel metal alloy is about 45-50 weight percent. In yet another and/or alternative non-limiting composition, the rhenium content of the novel metal alloy is about 47-48 weight percent. As can be appreciated, other weight percentages of the rhenium content of the novel metal alloy can be used. In another and/or alternative embodiment of the invention, the molybdenum content of the novel metal alloy in accordance with the present invention is at least about 40 weight percent. In one non-limiting composition, the molybdenum content of the novel metal alloy is at least about 45 weight percent. In another and/or alternative non-limiting composition, the molybdenum content of the novel metal alloy is at least about 50 weight percent. In still another and/or alternative non-limiting composition, the molybdenum content of the novel metal alloy is about 50-60 percent. In yet another and/or alternative non-limiting composition, the molybdenum content of the novel metal alloy is about 50-56 weight percent. As can be appreciated, other weight percentages of the molybdenum content of the novel metal alloy can be used. The novel metal alloy can include controlled amounts of at least one additional metal which includes titanium, yttrium, and/or zirconium; however, this is not required. The addition of controlled amounts of titanium, yttrium, and/or zirconium to the molybdenum and rhenium alloy has been found to form a metal alloy that has improved physical properties over a metal alloy that principally includes molybdenum and rhenium. For instance, the addition of controlled amounts of titanium, yttrium, and/or zirconium to the molybdenum and rhenium alloy can result in 1) an increase in yield strength of the alloy as compared to a metal alloy that principally includes molybdenum and rhenium, 2) an increase in tensile elongation of the alloy as compared to a metal alloy that principally includes molybdenum and rhenium, 3) an increase in ductility of the alloy as compared to a metal alloy that principally includes molybdenum and rhenium, 4) a reduction in grain size of the alloy as compared to a metal alloy that principally includes molybdenum and rhenium, 5) a reduction in the amount of free carbon, oxygen and/or nitrogen in the alloy as compared to a metal alloy that principally includes molybdenum and rhenium, and/or 6) a reduction in the tendency of the alloy to form micro-cracks during the forming of the alloy into a medical device as compared to the forming of a medical device from a metal alloy that principally includes molybdenum and rhenium. The combined content of titanium, yttrium and zirconium in the novel metal alloy, when used, is less than about 5 weight percent, typically no more than about 1 weight percent, and more typically no more than about 0.5 weight percent. A higher weight percent content of titanium, yttrium and/or zirconium in the novel metal alloy can begin to adversely affect the brittleness of the novel metal alloy. When titanium is included in the novel metal alloy, the titanium content is typically less than about 1 weight percent, more typically less than about 0.6 weight percent, even more typically about 0.05-0.5 weight percent, still even more typically about 0.1-0.5 weight percent. As can be appreciated, other weight percentages of the titanium content of the novel metal alloy can be used. When zirconium is included in the novel metal alloy, the zirconium content is typically less than about 0.5 weight percent, more typically less than about 0.3 weight percent, even more typically about 0.01-0.25 weight percent, still even more typically about 0.05-0.25 weight percent. As can be appreciated, other weight percentages of the zirconium content of the novel metal alloy can be used. When titanium and zirconium are included in the novel metal alloy, the weight ratio of titanium to zirconium is about 1-10:1, typically about 1.5-5:1, and more typically about 1.75-2.5:1. When yttrium is included in the novel metal alloy, the yttrium content is typically less than about 0.3 weight percent, more typically less than about 0.2 weight percent, and even more typically about 0.01-0.1 weight percent. As can be appreciated, other weight percentages of the yttrium content of the novel metal alloy can be used. The inclusion of titanium, yttrium and/or zirconium in the novel metal alloy is believed to result in a reduction of oxygen trapped in the solid solution of the novel metal alloy. The reduction of trapped oxygen enables the formation of a smaller grain size in the novel metal alloy and/or an increase in the ductility of the novel metal alloy. The reduction of trapped oxygen in the novel metal alloy can also increase the yield strength of the novel metal alloy as compared to alloys of only molybdenum and rhenium (i.e., 2-10% increase). The inclusion of titanium, yttrium and/or zirconium in the novel metal alloy is also believed to cause a reduction in the trapped free carbon in the novel metal alloy. The inclusion of titanium, yttrium and/or zirconium in the novel metal alloy is believed to form carbides with the free carbon in the novel metal alloy. This carbide formation is also believed to improve the ductility of the novel metal alloy and to also reduce the incidence of cracking during the forming of the metal alloy into a medical device (e.g., stent, etc.). As such, the novel metal alloy exhibits increased tensile elongation as compared to alloys of only molybdenum and rhenium (i.e., 1-8% increase). The inclusion of titanium, yttrium and/or zirconium in the novel metal alloy is also believed to cause a reduction in the trapped free nitrogen in the novel metal alloy. The inclusion of titanium, yttrium and/or zirconium in the novel metal alloy is believed to form carbo-nitrides with the free carbon and free nitrogen in the novel metal alloy. This carbo-nitride formation is also believed to improve the ductility of the novel metal alloy and to also reduce the incidence of cracking during the forming of the metal alloy into a medical device (e.g., stent, etc.). As such, the novel metal alloy exhibits increased tensile elongation as compared to alloys of only molybdenum and rhenium (i.e., 1-8% increase). The reduction in the amount of free carbon, oxygen and/or nitrogen in the novel metal alloy is also believed to increase the density of the novel metal alloy (i.e., 1-5% increase). The formation of carbides, carbo-nitrides, and/or oxides in the novel metal alloy results in the formation of dispersed second phase particles in the novel metal alloy, thereby facilitating in the formation of small grain sizes in the metal alloy. The novel metal alloy includes less than about 5 weight percent other metals and/or impurities. A high purity level of the novel metal alloy results in the formation of a more homogeneous alloy, which in turn results in a more uniform density throughout the novel metal alloy, and also results in the desired yield and ultimate tensile strengths of the novel metal alloy. The density of the novel metal alloy is generally at least about 12 gm/cc, and typically at least about 13-13.5 gm/cc. This substantially uniform high density of the novel metal alloy significantly improves the radiopacity of the novel metal alloy. In one non-limiting composition, the novel metal alloy includes less than about 1 weight percent other metals and/or impurities. In another and/or alternative non-limiting composition, the novel metal alloy includes less than about 0.5 weight percent other metals and/or impurities. In still another and/or alternative non-limiting composition, the novel metal alloy includes less than about 0.4 weight percent other metals and/or impurities. In yet another and/or alternative non-limiting composition, the novel metal alloy includes less than about 0.2 weight percent other metals and/or impurities. In still yet another and/or alternative non-limiting composition, the novel metal alloy includes less than about 0.1 weight percent other metals and/or impurities. In a further and/or alternative non-limiting composition, the novel metal alloy includes less than about 0.05 weight percent other metals and/or impurities. In still a further and/or alternative non-limiting composition, the novel metal alloy includes less than about 0.02 weight percent other metals and/or impurities. In yet a further and/or alternative non-limiting composition, the novel metal alloy includes less than about 0.01 weight percent other metals and/or impurities. As can be appreciated, other weight percentages of the amount of other metals and/or impurities in the novel metal alloy can exist. The novel metal alloy includes a certain amount of carbon and oxygen. These two elements have been found to affect the forming properties and brittleness of the novel metal alloy. The controlled atomic ratio of carbon and oxygen in the novel metal alloy also can be used to minimize the tendency of the novel metal alloy to form micro-cracks during the forming of the novel alloy into a medical device, and/or during the use and/or expansion of the medical device in a body passageway. In one non-limiting embodiment of the invention, the novel metal alloy includes up to about 200 ppm carbon and up to about 150 ppm oxygen. Higher carbon and oxygen contents in the novel metal alloy are believed to adversely affect one or more physical properties of the metal alloy that are useful or desired in forming and/or using a medical device. In one non-limiting formulation, the novel metal alloy includes up to about 150 ppm carbon. In still another and/or alternative non-limiting formulation, the novel metal alloy includes up to about 100 ppm carbon. In yet another and/or alternative non-limiting formulation, the novel metal alloy includes less than about 50 ppm carbon. In still yet another and/or alternative non-limiting formulation, the novel metal alloy includes up to about 100 ppm oxygen. In a further and/or alternative non-limiting formulation, the novel metal alloy includes up to about 75 ppm oxygen. In still a further and/or alternative non-limiting formulation, the novel metal alloy includes up to about 50 ppm oxygen. In yet a further and/or alternative non-limiting formulation, the novel metal alloy includes up to about 30 ppm oxygen. In still yet a further and/or alternative non-limiting formulation, the novel metal alloy includes less than about 20 ppm oxygen. In yet a further and/or alternative non-limiting formulation, the novel metal alloy includes less than about 10 ppm oxygen. As can be appreciated, other amounts of carbon and/or oxygen in the novel metal alloy can exist. In another and/or alternative non-limiting embodiment of the invention, the carbon to oxygen atomic ratio in the novel metal alloy is generally at least about 2:1 (i.e., weight ratio of about 1.5:1). The control of the atomic ratio of carbon to oxygen in the novel metal alloy allows for the redistribution of oxygen in the metal alloy so as to minimize the tendency of micro-cracking in the novel metal alloy during the forming of the novel alloy into a medical device, and/or during the use and/or expansion of the medical device in a body passageway. When the carbon to oxygen atomic ratio falls below 2-2.5:1 (i.e., weight ratio of about 1.5-1.88:1), the degree of elongation of the novel metal alloy decreases and the incidence of micro-cracking increases, thus adversely affecting one or more physical properties of the metal alloy that are useful or desired in forming and/or using the medical device. In one non-limiting formulation, the carbon to oxygen atomic ratio in the novel metal alloy is generally at least about 2.5:1 (i.e., weight ratio of about 1.88:1). In another and/or alternative non-limiting formulation, the carbon to oxygen atomic ratio in the novel metal alloy is generally at least about 3:1 (i.e., weight ratio of about 2.25:1). In still another and/or alternative non-limiting formulation, the carbon to oxygen atomic ratio in the novel metal alloy is generally at least about 4:1 (i.e., weight ratio of about 3:1). In yet another and/or alternative non-limiting formulation, the carbon to oxygen atomic ratio in the novel metal alloy is generally at least about 5:1 (i.e., weight ratio of about 3.75:1). In still yet another and/or alternative non-limiting formulation, the carbon to oxygen atomic ratio in the novel metal alloy is generally about 2.5-50:1 (i.e., weight ratio of about 1.88-37.54:1). In a further and/or alternative non-limiting formulation, the carbon to oxygen atomic ratio in the novel metal alloy is generally about 2.5-20:1 (i.e., weight ratio of about 1.88-15:1). In still a further and/or alternative non-limiting formulation, the carbon to oxygen atomic ratio in the novel metal alloy is generally about 2.5-10:1 (i.e., weight ratio of about 1.88-7.5:1). In yet a further and/or alternative non-limiting formulation, the carbon to oxygen atomic ratio in the novel metal alloy is generally about 2.5-5:1 (i.e., weight ratio of about 1.88-3.75:1). As can be appreciated, other atomic ratios of the carbon to oxygen in the novel metal alloy can be used. The novel metal alloy includes a controlled amount of nitrogen. Large amounts of nitrogen in the novel metal alloy can adversely affect the ductility of the novel metal alloy. This can in turn adversely affect the elongation properties of the novel metal alloy. A nitrogen content in the novel metal alloy of over 20 ppm can begin to cause the ductility of the novel metal alloy to unacceptably decrease, thus adversely affect one or more physical properties of the metal alloy that are useful or desired in forming and/or using the medical device. In one non-limiting embodiment of the invention, the novel metal alloy includes less than about 30 ppm nitrogen. In one non-limiting formulation, the novel metal alloy includes less than about 25 ppm nitrogen. In still another and/or alternative non-limiting formulation, the novel metal alloy includes less than about 10 ppm nitrogen. In yet another and/or alternative non-limiting formulation, the novel metal alloy includes less than about 5 ppm nitrogen. As can be appreciated, other amounts of nitrogen in the novel metal alloy can exist. The novel metal alloy has several physical properties that positively affect the medical device when at least partially formed of the novel metal alloy. In one non-limiting embodiment of the invention, the average hardness of the novel metal alloy tube used to form the medical device is generally at least about 60 (HRC) at 77° F. In one non-limiting aspect of this embodiment, the average hardness of the novel metal alloy tube used to form the medical device is generally at least about 70 (HRC) at 77° F., and typically about 80-100 (HRC) at 77° F. In another and/or alternative non-limiting embodiment of the invention, the average ultimate tensile strength of the novel metal alloy used to form the medical device is generally at least about 60 UTS (ksi). In non-limiting aspect of this embodiment, the average ultimate tensile strength of the novel metal alloy used to form the medical device is generally at least about 70 UTS (ksi), typically about 80-150 UTS (ksi), and more typically about 100-150 UTS (ksi). In still another and/or alternative non-limiting embodiment of the invention, the average yield strength of the novel metal alloy used to form the medical device is at least about 70 ksi. In one non-limiting aspect of this embodiment, the average yield strength of the novel metal alloy used to form the medical device is at least about 80 ksi, and typically about 100-140 (ksi). In yet another and/or alternative non-limiting embodiment of the invention, the average grain size of the novel metal alloy used to form the medical device is greater than 5 ASTM (e.g., ASTM E 112-96). The small grain size of the novel metal alloy enables the medical device to have the desired elongation and ductility properties that are useful in enabling the medical device to be formed, crimped and/or expanded. In one non-limiting aspect of this embodiment, the average grain size of the novel metal alloy used to form the medical device is about 5.2-10 ASTM, typically about 5.5-9 ASTM, more typically about 6-9 ASTM, still more typically about 6-8 ASTM, even more typically about 6-7 ASTM, and still even more typically about 6.5-7 ASTM. In still yet another and/or alternative non-limiting embodiment of the invention, the average tensile elongation of the novel metal alloy used to form the medical device is at least about 25%. An average tensile elongation of at least 25% for the novel metal alloy is important to enable the medical device to be properly expanded when positioned in the treatment area of a body passageway. A medical device that does not have an average tensile elongation of at least about 25% can form micro-cracks and/or break during the forming, crimping and/or expansion of the medical device. In one non-limiting aspect of this embodiment, the average tensile elongation of the novel metal alloy used to form the medical device is about 25-35%. The unique combination of the rhenium content in the novel metal alloy in combination with achieving the desired purity and composition of the alloy and the desired grain size of the novel metal alloy results in 1) a medical device having the desired high ductility at about room temperature, 2) a medical device having the desired amount of tensile elongation, 3) a homogeneous or solid solution of a metal alloy having high radiopacity, 4) a reduction or prevention of microcrack formation and/or breaking of the metal alloy tube when the metal alloy tube is sized and/or cut to form the medical device, 5) a reduction or prevention of microcrack formation and/or breaking of the medical device when the medical device is crimped onto a balloon and/or other type of medical device for insertion into a body passageway, 6) a reduction or prevention of microcrack formation and/or breaking of the medical device when the medical device is bent and/or expanded in a body passageway, 7) a medical device having the desired ultimate tensile strength and yield strength, 8) a medical device that can have very thin wall thicknesses and still have the desired radial forces needed to retain the body passageway on an open state when the medical device has been expanded, and/or 9) a medical device that exhibits less recoil when the medical device is crimped onto a delivery system and/or expanded in a body passageway. Several non-limiting examples of the novel metal alloy in accordance with the present invention are set forth below:

| Metal/ Wt. % | Ex. 1 | Ex. 2 |
|---|---|---|
| C | <150 ppm | <50 ppm |
| Mo | 51-54% | 52.5-55.5% |
| O | <50 ppm | <10 ppm |
| N | <20 ppm | <10 ppm |
| Re | 46-49% | 44.5-47.5% |

| Metal/ Wt. % | Ex. 3 | Ex. 4 | Ex. 5 | Ex. 6 |
|---|---|---|---|---|
| C | ≦50 ppm | ≦50 ppm | ≦50 ppm | ≦50 ppm |
| Mo | 51-54% | 52.5-55.5% | 52-56% | 52.5-55% |
| O | ≦20 ppm | ≦20 ppm | ≦10 ppm | ≦10 ppm |
| N | ≦20 ppm | ≦20 ppm | ≦10 ppm | ≦10 ppm |
| Re | 46-49% | 44.5-47.5% | 44-48% | 45-47.5% |
| Ti | ≦0.4% | ≦0.4% | 0.2-0.4% | 0.3-0.4% |
| Y | ≦0.1% | ≦0.1% | 0-0.08% | 0.005-0.05% |
| Zr | ≦0.2% | ≦0.2% | 0-0.2% | 0.1-0.25% |

| Metal/ Wt. % | Ex. 7 | Ex. 8 | Ex. 9 | Ex. 10 |
|---|---|---|---|---|
| C | ≦40 ppm | ≦40 ppm | ≦40 ppm | ≦40 ppm |
| Mo | 51-53% | 51.5-54% | 52-55% | 52.5-55% |
| O | ≦15 ppm | ≦15 ppm | ≦15 ppm | ≦10 ppm |
| N | ≦10 ppm | ≦10 ppm | ≦10 ppm | ≦10 ppm |
| Re | 47-49% | 46-48.5% | 45-48% | 45-47.5% |
| Ti | 0.1-0.35% | 0% | 0% | 0.1-0.3% |
| Y | 0% | 0.002-0.08% | 0% | 0% |
| Zr | 0% | 0% | 00.1-0.2% | 0.05-0.15% |

| Metal/ Wt. % | Ex. 11 | Ex. 12 |
|---|---|---|
| C | ≦40 ppm | ≦40 ppm |
| Mo | 52-55% | 52.5-55.5% |
| O | ≦10 ppm | ≦10 ppm |
| N | ≦10 ppm | ≦10 ppm |
| Re | 45-49% | 44.5-47.5% |
| Ti | 0.05-0.4% | 0% |
| Y | 0.005-0.07% | 0.004-0.06% |
| Zr | 0% | 0.1-0.2% |

In examples 1 and 2 above, the novel metal alloy is principally formed of rhenium and molybdenum and the content of other metals and/or impurities is less than about 0.1 weight percent of the novel metal alloy, the atomic ratio of carbon to oxygen is about 2.5-10:1 (i.e., weight ratio of about 1.88-7.5:1), the average grain size of the novel metal alloy is about 6-9 ASTM, the tensile elongation of the metal alloy is about 25-35%, the average density of the metal alloy is at least about 13.4 gm/cc, the average yield strength of the metal alloy is about 98-122 (ksi), the average ultimate tensile strength of the metal alloy is about 100-150 UTS (ksi), and the average hardness of the metal alloy is about 80-100 (HRC) at 77° F. In examples 3-12 above, the novel metal alloy is principally formed of rhenium and molybdenum and at least one metal of titanium, yttrium and/or zirconium, and the content of other metals and/or impurities is less than about 0.1 weight percent of the novel metal alloy, the ratio of carbon to oxygen is about 2.5-10:1, the average grain size of the novel metal alloy is about 6-9 ASTM, the tensile elongation of the metal alloy is about 25-35%, the average density of the metal alloy is at least about 13.6 gm/cc, the average yield strength of the metal alloy is at least about 110 (ksi), the average ultimate tensile strength of the metal alloy is about 100-150 UTS (ksi), and the average hardness of the metal alloy is about 80-100 (HRC) at 77° F.

In still a further and/or alternative one non-limiting aspect of the invention, the novel metal alloy that is used to form all or a portion of the medical device includes tantalum and tungsten. In one non-limiting embodiment, the novel metal alloy is formed of a majority weight percent tantalum and tungsten. Typically, the tantalum and tungsten content of the novel metal alloy is at least about 80 weight percent, more typically at least about 90 weight percent, even more typically at least about 95 weight percent, still even more typically at least about 99 weight percent, and yet even more typically at least about 99.9 weight percent; however, other weight percentages can be used. Generally the novel metal alloy of tantalum and tungsten includes at least about 0.5 weight percent tungsten and at least about 10 weight percent tantalum, typically at least about 2 weight percent tungsten and at least about 20 weight percent tantalum, and more typically at least about 2.5 weight percent tungsten and at least about 50 weight percent tantalum; however, other weight percentages of the tantalum and/or tungsten in the novel metal alloy can be used. Generally the novel metal alloy of tantalum and tungsten includes less than about 2 weight percent impurities, typically less than about 1 weight percent impurities, more typically less than about 0.5 weight percent impurities, still more typically less than about 0.1 weight percent impurities, yet more typically less than about 0.03 weight percent impurities; however, other weight percent of impurities in the novel metal alloy can be used. The weight percent of carbon in the alloy of tantalum and tungsten is generally less than about 100 ppm, and typically less than about 50 ppm, more typically less than about 40 ppm, and still more typically less than about 25 ppm; however, other weight percentages of carbon in the novel metal alloy can be used. The weight percent of oxygen in the alloy of tantalum and tungsten is generally less than about 100 ppm, and typically less than about 50 ppm, more typically less than about 40 ppm, and still more typically less than about 25 ppm; however, other weight percentages of oxygen in the novel metal alloy can be used. The weight percent of nitrogen in the alloy of tantalum and tungsten is generally less than about 50 ppm, and typically less than about 40 ppm, more typically less than about 30 ppm, and still more typically less than about 25 ppm; however, other weight percentages of nitrogen in the novel metal alloy can be used. Several specific non-limiting novel metal alloy compositions for the tantalum and tungsten alloy that can form a part of or the complete medical device are set forth below in weight percent or ppm:

| Metal/ Wt. % | Ex. 1 | Ex. 2 | Ex. 3 |
|---|---|---|---|
| C | 0-50 ppm | 0-50 ppm | 0-50 ppm |
| Ca | 0-1% | 0-0.5% | 0% |
| Mg | 0% | 0-3% | 0% |
| Mo | 0% | 0-2% | 0% |
| O | 0-50 ppm | 0-50 ppm | 0-50 ppm |
| N | 0-50 ppm | 0-50 ppm | 0-50 ppm |
| Rare Earth Metal | 0-1% | 0-0.5% | 0% |
| Ta | 85-96% | 10-90% | 85-95% |
| W | 4-15% | 10-90% | 5-15% |

| Metal/ Wt. % | Ex. 4 | Ex. 5 | Ex. 6 |
|---|---|---|---|
| C | 0-50 ppm | 0-50 ppm | 0-50 ppm |
| Ca | 0% | 0% | 0% |
| Mg | 0% | 0% | 0% |
| Mo | 0% | 0% | 0% |

-continued

| | | | |
|---|---|---|---|
| O | 0-50 ppm | 0-50 ppm | 0-50 ppm |
| N | 0-50 ppm | 0-50 ppm | 0-50 ppm |
| Rare Earth Metal | 0% | 0% | 0% |
| Ta | 90.5-98% | 95-98% | 90-97.5% |
| W | 2-9.5% | 2% to less than 5% | 2.5-10% |

The impurity content in each of these examples is less than about 0.04 weight percent.

In still a further and/or alternative one non-limiting aspect of the invention, the novel metal alloy that is used to form all or a portion of the medical device increases the strength of the medical device as compared with stainless steel or chromium-cobalt alloys, thus less quantity of novel metal alloy can be used in the medical device to achieve similar strengths as compared to medical devices formed of different metals. As such, the resulting medical device can be made smaller and less bulky by use of the novel metal alloy without sacrificing the strength and durability of the medical device. Such a medical device can have a smaller profile, thus can be inserted in smaller areas, openings and/or passageways. The novel metal alloy also can increase the radial strength of the medical device. For instance, the thickness of the walls of the medical device and/or the wires used to form the medical device can be made thinner and achieve a similar or improved radial strength as compared with thicker walled medical devices formed of stainless steel or cobalt and chromium alloy. The novel metal alloy also can improve stress-strain properties, bendability and flexibility of the medical device, thus increase the life of the medical device. For instance, the medical device can be used in regions that subject the medical device to bending. Due to the improved physical properties of the medical device from the novel metal alloy, the medical device has improved resistance to fracturing in such frequent bending environments. In addition or alternatively, the improved bendability and flexibility of the medical device due to the use of the novel metal alloy can enable the medical device to be more easily inserted into a body passageway. The novel metal alloy can also reduce the degree of recoil during the crimping and/or expansion of the medical device. For example, the medical device better maintains its crimped form and/or better maintains its expanded form after expansion due to the use of the novel metal alloy. As such, when the medical device is to be mounted onto a delivery device when the medical device is crimped, the medical device better maintains its smaller profile during the insertion of the medical device in a body passageway. Also, the medical device better maintains its expanded profile after expansion so as to facilitate in the success of the medical device in the treatment area. In addition to the improved physical properties of the medical device by use of the novel metal alloy, the novel metal alloy has improved radiopaque properties as compared to standard materials such as stainless steel or cobalt-chromium alloy, thus reducing or eliminating the need for using marker materials on the medical device. For instance, the novel metal alloy is at least about 10-20% more radiopaque than stainless steel or cobalt-chromium alloy. The medical device that is at least partially formed from the novel metal alloy can be form by a variety of manufacturing techniques. In one non-limiting embodiment of the invention, the medical device that is at least partially formed from a rod or tube of the novel metal alloy. Medical devices that can be formed from a rod or tube include, but are not limited to, stents, grafts, vascular grafts, valves, orthopedic implants, sheaths, guide wires, balloon catheters, hypotubes, catheters, electrophysiology catheters, cutting devices, etc.

In another and/or alternative non-limiting aspect of the invention, the medical device can include a bistable construction. In such a design, the medical device has two or more stable configurations, including a first stable configuration with a first cross-sectional shape and a second stable configuration with a second cross-sectional shape. All or a portion of the medical device can include the bistable construction. The bistable construction can result in a generally uniform change in shape of the medical device, or one portion of the medical device can change into one or more configurations and one or more other portions of the medical device can change into one or more other configurations.

In still another and/or alternative non-limiting aspect of the invention, the medical device can be used in conjunction with one or more other biological agents that are not on the medical device. For instance, the success of the medical device can be improved by infusing, injecting or consuming orally one or more biological agents. Such biological agents can be the same and/or different from the one or more biological agents on and/or in the medical device. Such use of one or more biological agents are commonly used in systemic treatment of a patient after a medical procedure such as body wide aggressive anti-platelet and/or anti-coagulation therapy after the medical device has been inserted in the treatment area can be reduced or eliminated by use of the novel alloy. Although the medical device of the present invention can be designed to reduce or eliminate the need for long periods of body wide aggressive anti-platelet and/or anti-coagulation therapy after the medical device has been inserted in the treatment area, the use of one or more biological agents can be used in conjunction with the medical device to enhance the success of the medical device and/or reduce or prevent the occurrence of thrombosis. For instance, solid dosage forms of biological agents for oral administration, and/or for other types of administration (e.g., suppositories, etc.) can be used. Such solid forms can include, but are not limited to, capsules, tablets, effervescent tablets, chewable tablets, pills, powders, sachets, granules and gels. The solid form of the capsules, tablets, effervescent tablets, chewable tablets, pills, etc. can have a variety of shapes such as, but not limited to, spherical, cubical, cylindrical, pyramidal, and the like. In such solid dosage form, one or more biological agents can be admixed with at least one filler material such as, but not limited to, sucrose, lactose or starch; however, this is not required. Such dosage forms can include additional substances such as, but not limited to, inert diluents (e.g., lubricating agents, etc.). When capsules, tablets, effervescent tablets or pills are used, the dosage form can also include buffering agents; however, this is not required. Soft gelatin capsules can be prepared to contain a mixture of the one or more biological agents in combination with vegetable oil or other types of oil; however, this is not required. Hard gelatin capsules can contain granules of the one or more biological agents in combination with a solid carrier such as, but not limited to, lactose, potato starch, corn starch, cellulose derivatives of gelatin, etc; however, this is not required. Tablets and pills can be prepared with enteric coatings for additional time release characteristics; however, this is not required. Liquid dosage forms of the one or more biological agents for oral administration can include pharmaceutically acceptable emulsions, solutions, suspensions, syrups, elixirs, etc.; however, this is not required. In one non-limiting embodiment, when at least a portion of one or more biological agents is inserted into a treatment area (e.g., gel form, paste form, etc.) and/or provided orally (e.g., pill, capsule, etc.) and/or anally (suppository, etc.), one or more of the biological agents can be controllably released; however, this is not required. In one non-limiting example, one or more biological agents can be given to a patient in solid dosage form and one or more of such biological agents can be controllably released from such solid dosage forms. In another and/or alternative non-limiting example trapidil, trapidil derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof are given to a patient prior to, during and/or after the insertion of the medical device in a treatment area. Certain types of biological agents may be desirable to be present in a treated area for an extended period of time in order to utilize the full or nearly full clinical potential the biological agent. For instance, trapidil and/or trapidil derivatives is a compound that has many clinical attributes including, but not limited to, anti-platelet effects, inhibition of smooth muscle cells and monocytes, fibroblast proliferation and increased MAPK-1 which in turn deactivates kinase, a vasodilator, etc. These attributes can be effective in improving the success of a medical device that has been inserted at a treatment area. In some situations, these positive effects of trapidil and/or trapidil derivatives need to be prolonged in a treatment area in order to achieve complete clinical competency. Trapidil and/or trapidil derivatives has a half life in vivo of about 2-4 hours with hepatic clearance of 48 hours. In order to utilize the full clinical potential of trapidil and/or trapidil derivatives, trapidil and/or trapidil derivatives should be metabolized over an extended period of time without interruption; however, this is not required. By inserting trapidil and/or trapidil derivatives in a solid dosage form, the trapidil and/or trapidil derivatives could be released in a patient over extended periods of time in a controlled manner to achieve complete or nearly complete clinical competency of the trapidil and/or trapidil derivatives. In another and/or alternative non-limiting example, one or more biological agents are at least partially encapsulated in one or more polymers. The one or more polymers can be biodegradable, non-biodegradable, porous, and/or non-porous. When the one or more polymers are biodegradable, the rate of degradation of the one or more biodegradable polymers can be used to at least partially control the rate at which one or more biological agent are released into a body passageway and/or other parts of the body over time. The one or more biological agents can be at least partially encapsulated with different polymer coating thickness, different numbers of coating layers, and/or with different polymers to alter the rate at which one or more biological agents are released in a body passageway and/or other parts of the body over time. The rate of degradation of the polymer is principally a function of 1) the water permeability and solubility of the polymer, 2) chemical composition of the polymer and/or biological agent, 3) mechanism of hydrolysis of the polymer, 4) the biological agent encapsulated in the polymer, 5) the size, shape and surface volume of the polymer, 6) porosity of the polymer, 7) the molecular weight of the polymer, 8) the degree of cross-linking in the polymer, 9) the degree of chemical bonding between the polymer and biological agent, and/or 10) the structure of the polymer and/or biological agent. As can be appreciated, other factors may also affect the rate of degradation of the polymer. When the one or more polymers are biostable, the rate at when the one or more biological agents are released from the biostable polymer is a function of 1) the porosity of the polymer, 2) the molecular diffusion rate of the biological agent through the polymer, 3) the degree of cross-linking in the polymer, 4) the degree of chemical bonding between the polymer and biological agent, 5) chemical composition of the polymer and/or biological agent, 6) the biological agent encapsulated in the polymer, 7) the size, shape and surface volume of the polymer, and/or 8) the structure of the polymer and/or biological agent. As can be appreciated, other factors may also affect the rate of release of the one or more biological agents from the biostable polymer. Many different polymers can be used such as, but not limited to, aliphatic polyester compounds (e.g., PLA (i.e. poly(D, L-lactic acid), poly(L-lactic acid)), PLGA (i.e. poly(lactide-co-glycoside), etc.), POE, PEG, PLLA, parylene, chitosan and/or derivatives thereof. As can be appreciated, the at least partially encapsulated biological agent can be introduced into a patient by means other than by oral introduction, such as, but not limited to, injection, topical applications, intravenously, eye drops, nasal spray, surgical insertion, suppositories, intrarticularly, intraocularly, intranasally, intradermally, sublingually, intravesically, intrathecally, intraperitoneally, intracranially, intramuscularly, subcutaneously, directly at a particular site, and the like.

In yet another and/or alternative non-limiting aspect of the invention, the medical device is in the form of a stent. The stent can be an expandable stent that is expandable by a balloon and/or is self-expanding. The stent can have one or more body members. The one or more body members can include first and second ends and a wall surface disposed between the first and second ends. Typically each body member has a first cross-sectional area which permits delivery of the body member into a body passageway, and a second, expanded cross-sectional area. The expansion of one or more body members of the stent can be accomplished in a variety of manners. In one manner, one or more body members are expanded to the second cross-sectional area by a radially, outwardly extending force applied at least partially from the interior region of the body member (e.g. by use of a balloon, etc.). The body member can include shape memory materials; however, this is not required. The second cross-sectional area of the stent can be fixed or variable. The stent can be designed such that one or more body members expand while substantially retaining the original longitudinal length of the body member; however, this is not required. The one or more body members can have a first cross-sectional shape that is generally circular so as to form a substantially tubular body member; however, the one or more body members can have other cross-sectional shapes. When the stent includes two or more body members, the two or more body members can be connected together by at least one connector member. The stent can include rounded, smooth and/or blunt surfaces to minimize and/or prevent potential damage to a body passageway as the stent is inserted into a body passageway and/or expanded in a body passageway; however, this is not required. The stent can be treated with gamma, beta and/or e-beam radiation, and/or otherwise sterilized; however, this is not required.

In one non-limiting application of the present invention, there is provided a medical device and method for using such medical device to inhibit or prevent thrombosis after the medical device has been inserted into a body passageway. The medical device can have one-limiting advantage of reducing or eliminating the need for long periods of body-wide anti-platelet and/or anti-coagulation therapy after the medical device has been inserted in the treatment area. The medical device can have one non-limiting advantage of delivering one or more biological agents into a treatment area (e.g., body passageway, etc.). Such a medical device can be designed to be inserted in and/or be connected to a body passageway (e.g., blood vessel, etc.) and which medical device inhibits or prevents thrombosis. The medical device can be designed to be used as a biological agent delivery mechanism to deliver one or more biological agents to and/or into a wall of a body passageway and/or down stream from the site of implantation of the medical device. In one non-limiting design, the medical device is a stent comprised of a base material that includes at least one layer of biological agent and at least one polymer layer that is used to at partially control the release of the biological agent from the medical device. In one non-limiting controlled release arrangement, molecular diffusion through a polymer is used to control the release rate of one or more biological agents from the medical device When a molecular diffusion mechanism is used, one or more non-porous polymer layers can be used to facilitate in such molecular diffusion; however, this is not required. The molecular composition, molecular structure and/or coating thickness of the non-porous polymer can be selected to control the release rate of one or more biological agents from the medical device. In another and/or alternative non-limiting design, the medical device is a surgical graft comprised of a flexible base material upon which at least one layer of at least one biological agent is applied to an inner and/or outer surface of the surgical graft. At least one polymer layer can be applied to the surgical graft to at least partially control the release rate of the one or more biological agents from the surgical graft; however, this is not required. The polymer layer can include a porous or non-porous polymer. The one or more polymers and/or biological agents that are used in conjunction with the stent or the surgical graft can 1) form at least a portion of the medical device, 2) be coated on one or more regions of the medical device, and/or 3) be contained in one or more regions within the medical device. Non-limiting examples of polymers that can be used include parylene, PLGA, POE, PGA, PLLA, PAA, PEG, chitosan and/or derivatives of one or more of these polymers; however, other or additional polymers can be used. Many different biological agents can be used. Such biological agents can include anti-platelet compounds and/or anticoagulant compounds such as, but not limited to, warfarin (Coumadin) and/or derivatives, aspirin and/or derivatives, clopidogrel and/or derivatives, ticlopidine and/or derivatives, hirudin and/or derivatives, dipyridamole and/or derivatives, trapidil and/or derivatives, and/or heparin and/or low molecular weight heparin and/or derivatives. As can be appreciated, one or more other anti-thrombotic biological agents can be combined with the medical device such as, but not limited to, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. The structure of the medical device during manufacture can be pre-treated (e.g., plasma etching, etc.) to facilitate in the coating of one or more polymers and/or biological agents on the medical device; however, this is not required. The surface topography of the base structure of the medical device can be uniform or varied to achieve the desired operation and/or biological agent released from the medical device. As can be appreciated, one or more regions of the medical device can be constructed by use of one or more microelectromechanical manufacturing techniques; however, this is not required. Materials that can be used by microelectromechanical manufacturing techniques technology include, but are not limited to, chitosan, a chitosan derivative, PLGA, a PLGA derivative, PLA, a PLA derivative, PEVA, a PEVA derivative, PBMA, a PBMA derivative, POE, a POE derivative, PGA, a PGA derivative, PLLA, a PLLA derivative, PAA, a PAA derivative, PEG, and chitosan, a chitosan derivative, PLGA, a PLGA derivative, PLA, a PLA derivative, PEVA, a PEVA derivative, PBMA, a PBMA derivative, POE, a POE derivative, PGA, a PGA derivative, PLLA, a PLLA derivative, PAA, a PAA derivative, PEG, a PEG derivative, and/or a PEG derivative. The medical device can include one or more surface structures, micro-structures, internal structures that include one or more biological agents d/or polymers; however, this is not required. These structures can be at least partially formed by MEMS (e.g., micro-machining, etc.) technology and/or other types of technology. The structures can be designed to contain and/or be fluidly connected to a passageway in the medical device that includes one or more biological agents; however, this is not required. The structures can be used to engage and/or penetrate surrounding tissue or organs once the medical device has been positioned on and/or in a patient; however, this is not required. One or more polymers and/or biological agents can be inserted in these structures and/or at least partially form these structures of the medical device. The structures can be clustered together or disbursed throughout the surface of the medical device. Similar shaped and/or sized structures can be used, or different shaped and/or sized structures can be used. Typically the micro-structures, when formed, extend from or into the outer surface no more than about 400 microns, and more typically less than about 300 microns, and more typically about 15-250 microns; however, other sizes can be used. The time period one or more biological agents are released from the medical device is typically dependent on the designed medical treatment and/or other factors. In one non-limiting arrangement, one or more biological agents are released from the medical device for at least several days after the medical device is inserted in the body of a patient; however, this is not required. In another one non-limiting arrange ent, one or more biological agents are released from the medical device for at least about one week after the medical device is inserted in the body of a patient. In still another one non-limiting arrangement, one or more biological agents are released from the medical device for at least about two weeks after the medical device is inserted in the body of a patient. In yet another one non-limiting arrangement, one or more biological agents are released from the medical device for about one week to one year after the medical device is inserted in the body of a patient. As can be appreciated, the time frame that one or more of the biological agents can be released from the medical device can be longer or shorter. The time period for the release of two or more biological agents from the medical device can be the same or different. The type of the one or more biological agents used on the medical device, the release rate of the one or more biological agents from the medical device, and/or the concentration of the one or more biological agents being released from the medical device can be the same or different. The controlled release rate of one or more biological agents from the medical device can result in reduced amounts and/or reduce time period of systemic drug therapy after the medical device is inserted in the treatment area. In one non-limiting arrangement, the medical device releases one or more biological agents for a period of time such that systemic drug therapy after the medical device is inserted in the treatment area is reduced to less than one year. In another and/or alternative non-limiting arrangement, the medical device releases one or more biological agents for a period of time such that systemic drug therapy after the medical device is inserted in the treatment area is reduced to less than one month. In still another and/or alternative non-limiting arrangement, the medical device releases one or more biological agents for a period of time such that systemic drug therapy after the medical device is inserted in the treatment area is reduced to less than one week. The medical device can be temporality used in conjunction with other biological agents. For instance, the success of the medical device can be improved by infusing, injecting or consuming orally one or more biological agents. Such biological agents can be the same and/or different from the one or more biological agents on and/or in the medical device. For instance, solid dosage forms of biological agents for oral administration can be used. Such solid forms can include, but are not limited to, capsules, tablets, effervescent tablets, chewable tablets, pills, powders, sachets, granules and gels.

In another and/or alternative non-limiting application of the present invention, there is provided a medical device that is adapted for introduction into a patient and/or for topical use (e.g., lotion, salve, gel, etc.), which medical device releases one or more biological agents in a controlled release manner. The medical device can have a variety of applications such as, but not limited to, placement into the vascular system. As can be appreciated, the medical device can have other or additional uses. One or more biological agents on and/or in the medical device can be released controllably and/or uncontrollably from the medical device. As such, all of the biological agents can be controllably released from the medical device, all of the biological agents can be uncontrollably released from the medical device, or one or more biological agents can be controllably released and one or more biological agents can be uncontrollably released from the medical device. The controlled release of the one or more biological agents from the medical device can be at least partially controlled by molecular diffusion through one or more non-porous polymer layers; however, it will be appreciated that other or additional mechanisms can be used to control the rate of release of one or more biological agents from the medical device. For instance, the one or more biological agents can be selected so as to be chemically bonded to one or more polymers to control the rate of release of one or more biological agents from the medical device; however, this is not required. The one or more polymers can include cross-links to control the rate of release of one or more biological agents from the medical device; however, this is not required. The one or more polymers and/or one or more biological agents can be hydrophobic or hydrophilic, thus can be used to facilitate in the controlled release of the one or more biological agents from the medical device; however, this is not required. The thickness of the one or more polymer layers can be selected to facilitate in the controlled release of the one or more biological agents; however, this is not required. The molecular weight and/or molecular structure of the one or more biological agents and/or one or more polymer can be selected to facilitate in the release of the one or more biological agents; however, this is not required. Many different biological agents can be used. Such biological agents can include anti-platelet compounds and/or anticoagulant compounds such as, but not limited to, warfarin (Coumadin) and/or derivatives, aspirin and/or derivatives, clopidogrel and/or derivatives, ticlopidine and/or derivatives, hirudin and/or derivatives, dipyridamole and/or derivatives, trapidil and/or derivatives, and/or heparin and/or low molecular weight heparin and/or derivatives. As can be appreciated, one or more other anti-thrombotic biological agents can be combined with the medical device such as, but not limited to, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. In still another one non-limiting arrangement, one or more biological agents are released from the medical device for at least about two weeks after the medical device is inserted in the body of a patient. In yet another one non-limiting arrangement, one or more biological agents are released from the medical device for about one week to one year after the medical device is inserted in the body of a patient. As can be appreciated, the time frame that one or more of the biological agents can be released from the medical device can be longer or shorter. The time period for the release of two or more biological agents from the medical device can be the same or different. The type of the one or more biological agents used on the medical device, the release rate of the one or more biological agents from the medical device, and/or the concentration of the one or more biological agents being released from the medical device can be the same or different.

One non-limiting object of the present invention is the provision of a medical device having improved procedural success rates.

Another and/or alternative non-limiting object of the present invention is the provision of a medical device that can be implanted into the vascular system of a mammalian without the need of body wide aggressive anti-platelet and/or anti-coagulation therapy over extended periods of time and a method using such a device.

Still another and/or alternative non-limiting object of the present invention is the provision of a medical device in the form of a stent that inhibits or prevents the occurrence of thrombosis after the medical device has been inserted into a body passageway.

Yet another and/or alternative non-limiting object of the present invention is the provision of a medical device that is at least partially formed of, contains and/or is coated with one or more biological agents.

Still yet another and/or alternative non-limiting object of the present invention is the provision of a medical device that inhibits or prevents thrombosis by localized release of one or more biological agents and a method using such a device.

Another and/or alternative non-limiting object of the present invention is the provision of a medical device that controllably releases one or more biological agents.

Yet another and/or alternative non-limiting object of the present invention is the provision of a medical device that inhibits or prevents the occurrence of in-stent restenosis, vascular narrowing and/or restenosis after the medical device has been inserted into a body passageway.

Still another and/or alternative non-limiting object of the present invention is the provision of a medical device that includes one or more surface structures and/or micro-structures.

Yet another and/or alternative non-limiting object of the present invention is the provision of a medical device that includes one or more internal structures, micro-structures and/or surface structures that include and/or are coated with one or more biological agents and/or polymers.

Still another and/or alternative non-limiting object of the present invention is the provision of a medical device that includes one or more surface structures, micro-structures and/or internal structures and a protective coating that at least partially covers and/or protects such structures.

Still a further and/or alternative non-limiting object of the present invention is the provision of a medical device that can be used in conjunction with one or more biological agents not on or in the medical device.

These and other advantages will become apparent to those skilled in the art upon the reading and following of this description taken together with the accompanying drawings.

BRIEF DESCRIPTION OF THE DRAWINGS

Reference may now be made to the drawings, which illustrate various embodiments that the invention may take in physical form and in certain parts and arrangements of parts wherein.

DETAILED DESCRIPTION OF THE INVENTION

Figure 1:
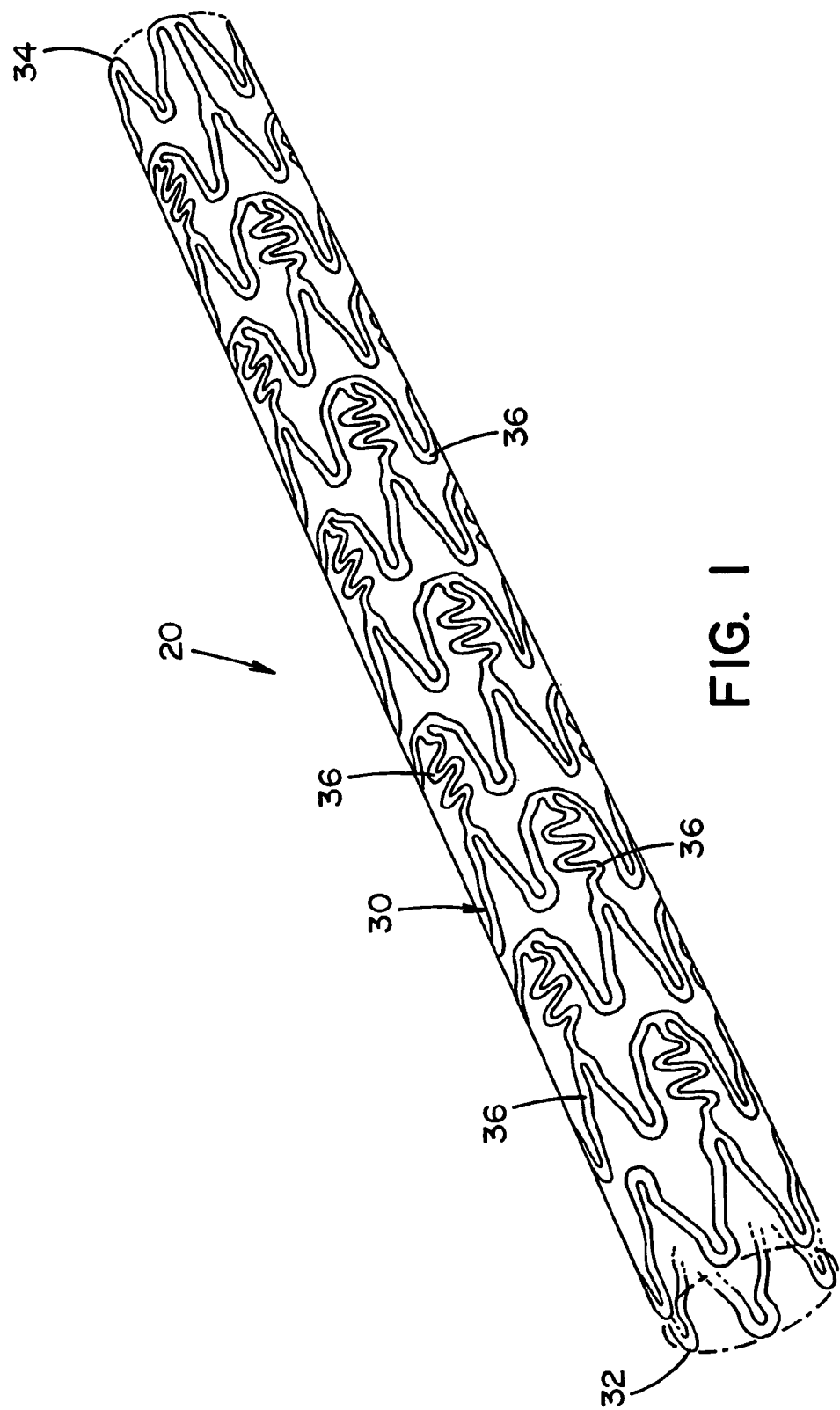
FIG. 1 is a perspective view of a section of a medical device in the form of an unexpanded stent which permits delivery of the stent into a body passageway.
Figure 2:
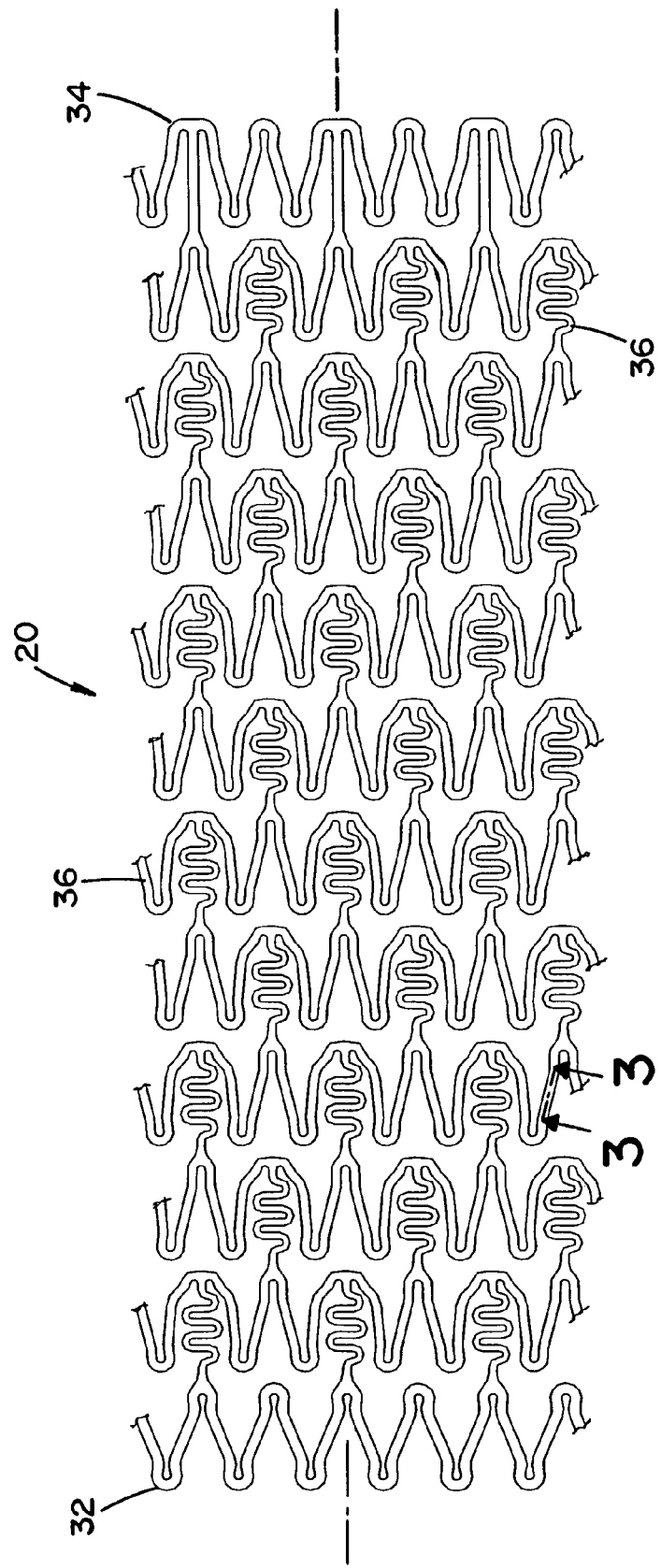
FIG. 2 is a sectional view of the stent of FIG. 1.

Referring now to the drawings wherein the showing is for the purpose of illustrating preferred embodiments of the invention only and not for the purpose of limiting the same, FIGS. 1-2 disclose a medical device in the form of a stent for use in a body passageway. The medical device of the present invention can be designed to address one or more of the shortcomings of prior medical devices. One non-limiting feature of the medical device of the present invention can be to locally deliver one or more biological agents to a particular body region. Another and/or alternative non-limiting feature of the medical device of the present invention can be to locally deliver one or more biological agents to a particular body region and to at least partially release one or more biological agents in a controlled manner.

Figure 15:
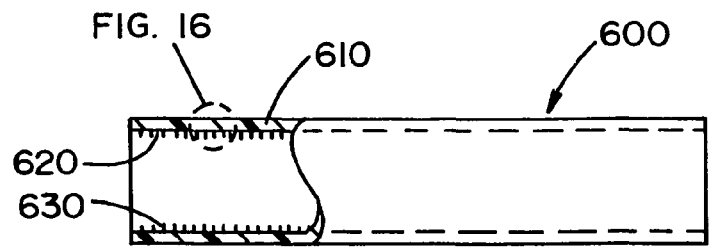
FIG. 15 is a perspective view of a section of medical device in the form of a surgical graft that includes an internal biological agent coating and a polymer coating over the biological agent.
Figure 16:
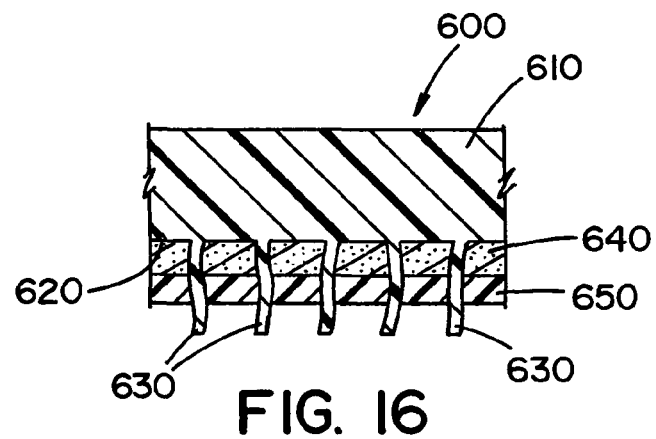
FIG. 16 is an expanded section of the surgical graft identified in FIG. 15; and, FIG. 17 is a cross-sectional view of a micro-needle on a medical device that is penetrating into the inner surface of a body passageway or organ.

Although, FIGS. 1-2 illustrate the medical device in the form of a stent for use in the cardiovascular field, the medical device can be used in other medical fields such as, but not limited to, orthopedic field, cardiology field, pulmonology field, urology field, nephrology field, gastroenterology field, gynecology field, otolaryngology field or other surgical fields. The medical device can be in a form other than a stent such as a surgical graft as illustrated in FIGS. 15 & 16), a suture, a staple, an orthopedic implant, a bandage, a valve, a micro or nano device, a vascular implant, a drug delivery catheter, an infusion catheter, a balloon, a catheter tip, a drug pump, tubing, a bag, a lead, a pacemaker, an implantable pulse generator, an implantable cardiac defibrillator, a cardioverger defibrillator, a defibrillator, a spinal stimulator, a brain stimulator, a sacral nerve stimulator, a chemical sensor, a spinal implant, a membrane surface, a sheath, a guide wire, a balloon catheter, a hypotube, a catheter (e.g., electrophysiology catheters, guide catheter, stent catheter, etc.), a cutting device, a PFO (patent foramen ovale) device, a wrap, a biological glue, a gel, etc. As can be appreciated, the medical device can take other forms (e.g., lotions, salves, gels, capsules, tablets, effervescent tablets, chewable tablets, pills, powders, sachets, granules, etc.).

The medical device of the present invention, when used for vascular applications, can be used to address various medical problems such as, but not limited to, restenosis, atherosclerosis, atherogenesis, angina, ischemic disease, congestive heart failure or pulmonary edema associated with acute myocardial infarction, atherosclerosis, thrombosis, controlling blood pressure in hypertension, platelet adhesion, platelet aggregation, smooth muscle cell proliferation, vascular complications, wounds, myocardial infarction, pulmonary thromboembolism, cerebral thromboembolism, thrombophiebitis, thrombocytopenia or bleeding disorders.

The medical device can be formed of a variety of materials such as, but not limited to, biostable polymers, biodegradable polymers, metals, plastics, cloth, fibers, or any combination thereof. As can be appreciated, many types of biodegradable polymers and non-biodegradable polymers can be used to at least partially form the medical device. The medical device can be at least partially biostable or at least partially biodegradable. The material or materials used to form the medical device include properties (e.g., strength, durability, hardness, biostability, bendability, coefficient of friction, radial strength, flexibility, tensile strength, longitudinal lengthening, stress-strain properties, improved recoil properties, radiopacity, heat sensitivity, biocompatability, biostability, biodegradability, biocompatability, etc.) that are selected to form a medical device which promotes the success of the medical device. When the medical device is in the form of a stent, the stent can be expandable such as by a balloon and/or self expanding. The material that is used to form one or more portions of the medical device is typically selected to withstand the manufacturing process used to form the medical device (e.g., electroplating, electro polishing, extrusion, molding, EDM machining, MEMS (e.g., micro-machining, etc.) manufacturing, chemical polishing, ion beam deposition or implantation, sputter coating, vacuum deposition, plasma deposition, etc.).

The medical device can include one or more surface structures, micro-structures and/or internal structures. Such structures can be formed by a variety of processes (e.g., machining, chemical modifications, chemical reactions, micromachining, etching, etc.). The one or more coatings and/or one or more surface structures, micro-structures and/or internal structures of the medical device can be used for a variety of purposes such as, but not limited to, 1) increasing the bonding and/or adhesion of one or more biological agents, adhesives, marker materials and/or polymers to the medical device, 2) changing the appearance or surface characteristics of the medical device, and/or 3) controlling the release rate of one or more biological agents. The techniques employed to deliver the medical device include, but are not limited to, angioplasty, vascular anastomoses, transplantation, implantation, subcutaneous introduction, minimally invasive surgical procedures, injection, topical applications, bolus administration, infusion, interventional procedures, and any combinations thereof. When the medical device is in the form of a surgical graft or stent as illustrated in FIGS. 1-17, the medical device can be implanted or applied by techniques such as, but not limited to, suturing, staples, adhesive, anastomoses, balloon delivery, sheath catheter delivery, etc.

Referring again to FIGS. 1-2, there is disclosed a medical device in the form of a stent for a body passageway. The stent is an expandable stent for at least partially expanding occluded segments of a body passageway; however, the stent can have other or additional uses. For example, the expandable stent may be used for, but not limited to, such purposes as 1) a supportive stent for placement within a blocked vasculature opened by transluminal recanalization, which are likely to collapse in the absence of an internal support; 2) forming a catheter passage through the mediastinal and/or other veins occluded by inoperable cancers; 3) reinforcement of catheter created intrahepatic communications between portal and/or hepatic veins in patients suffering from portal hypertension; 4) a supportive stent for placement in the narrowing of the esophagus, the intestine, the ureter and/or the urethra; and/or 5) a supportive stent for reinforcement of reopened and/or previously obstructed bile ducts. Accordingly, use of the term "stent" encompasses the foregoing or other usages within various types of body passageways.

As illustrated in FIG. 1, the medical device 20 in the form of an expandable stent includes at least one tubular shaped body member 30 having a first end 32, a second end 34, and member structures 36 disposed between the first and second ends. FIG. 2 illustrates the stent prior to being formed into a generally tubular shape. As can be appreciated, the stent can be formed of a plurality of body members connected together. Body member 30 has a first diameter which permits delivery of the body member into a body passageway. The first diameter of the body member is illustrated as being substantially constant along the longitudinal length of the body member. As can be appreciated, the body member can have a varying first diameter along at least a portion of the longitudinal length of the body member. The body member also has a second expanded diameter, not shown. The second diameter typically varies in size; however, the second diameter can be non-variable in size. The stent can be expanded in a variety of ways such as by a balloon and/or be at least partially self expanding. A balloon expandable stent is typically pre-mounted or crimped onto an angioplasty balloon catheter. The balloon catheter is then positioned into the patient via a guide wire. Once the stent is properly positioned, the balloon catheter is inflated to the appropriate pressure for stent expansion. After the stent has been expanded, the balloon catheter is deflated and withdrawn, leaving the stent deployed at the treatment area. A self expanding stent includes a material that has physical properties that do not require balloon expansion; however, a balloon can be used. These stents are typically manufactured in their final clinically relevant size and are temporarily reduced in size and mounted onto a delivery system; however, this is not required. The deployment strategy is similar to that of the balloon expandable stent except that a retaining system (e.g., sheath, adhesive, etc.) is withdrawn, degrades, breaks, etc. after the stent is positioned in the treatment area. After the retaining system is withdrawn, degrades or is broken, the stent expands. As can be appreciated, expansion of such a stent can be facilitated by use of a balloon, heat, etc.; however, this is not required.

One or more surfaces of the stent can be treated so as to have generally smooth surfaces. Generally, one or more ends of the stent are treated by filing, buffing, polishing, grinding, coating, and/or the like to remove or reduce the number of rough and/or sharp surfaces; however, this is not required. The smooth surfaces of the ends can be used to reduce potential damage to surrounding tissue as the stent is positioned in and/or expanded in a body passageway.

Referring now to FIGS. 3-14, there is illustrated a portion of the stent that includes and/or is coated with one or more biological agents that are used to improve the functionality and/or success of the medical device such as, but not limited to inhibiting or preventing thrombosis. As can be appreciated, the coating combinations and structural combinations illustrated in FIGS. 3-14 can be used on the surgical graft as illustrated in FIG. 15, and/or on other medical devices. As illustrated in FIGS. 3-15, the stent can include and/or be coated with one or more polymers and/or biological agents. The one or more polymers can be porous or non-porous polymers. The one or more biological agents can be, but are not limited to, anti-biotic agents, anti-body targeted therapy agents, anti-hypertensive agents, anti-microbial agents, anti-mitotic agents, anti-oxidants, anti-polymerases agents, anti-proliferative agents, anti-secretory agents, anti-tumor agents, anti-viral agents, bioactive agents, chemotherapeutic agents, cellular components, cytoskeletal inhibitors, drug, growth factors, growth factor antagonists, hormones, immunosuppressive agents, living cells, non-steroidal anti-inflammatory drugs, radioactive materials, radio-therapeutic agents, thrombolytic agents, vasodilator agents, etc. Non-limiting examples of biological agents that can be used on a stent for use in the vascular system include, but are not limited to, a vascular active agent that inhibits and/or prevents restenosis, vascular narrowing and/or in-stent restenosis. Non-limiting examples of such biological agents include anti-platelet compounds and/or anticoagulant compounds such as, but not limited to, warfarin (Coumadin) and/or derivatives, aspirin and/or derivatives, clopidogrel and/or derivatives, ticlopidine and/or derivatives, hirudin and/or derivatives, dipyridamole and/or derivatives, trapidil and/or derivatives, and/or heparin and/or low molecular weight heparin and/or derivatives. As can be appreciated, one or more other anti-thrombotic biological agents can be combined with the stent such as, but not limited to, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CS F, GM-CSF derivatives, or combinations thereof. For example, the amount of biological agent delivered to a certain region of a patient's body can be controlled by, but not limited to, one or more of the following: a) selecting the type of biological agent to be used on and/or in the stent, b) selecting the amount of biological agent to be used on and/or in the stent, c) selecting the coating thickness of the biological agent to be used on the stent, d) selecting the drug concentration of the biological agent to be used on and/or in the stent, e) selecting the solubility of the biological agent to be used on and/or in the stent, f) selecting the location the biological agent that is to be coated and/or impregnated on and/or in the stent, g) selecting the amount of surface area of the stent that is coated and/or impregnated with the biological agent, h) selecting the location of the biological agent on the stent, I) selecting the size, shape, amount and/or location of the one or more surface structures, micro-structures and/or internal structures of the stent that include and/or are integrated with the biological agent, j) selecting the type and/or amount of polymer to be mixed with the biological agent, k) selecting the type, amount and/or coating thickness of the polymer coating used to at least partially coat and/or encapsulate the biological agent, etc. As can be appreciated, the amount of one or more biological agent delivered to a region of the body can be at least partially controlled in other or additional ways.

One or more biological agents on and/or in the stent can be controllably released and/or immediately released to optimize their effects in a treatment area and/or to compliment the function and success of the stent in a treatment area. The controlled release of one or more biological agents from the stent can be accomplished by 1) controlling the size and/or shape of the surface structures, micro-structures and/or internal structures in the stent, and 2) combining and/or coating one or more biological agents with one or more polymers. As can be appreciated, the controlled release of one or more polymers can be accomplished by other and/or additional arrangements. The one or more polymers can also or alternatively be used to assist in binding the one or more biological agents to the stent. The one or more polymers can be biodegradable or biostable. The one or more polymers can be formulated to form a bond between one or more biological agents and the stent; however, this is not required. The one or more polymers and one or more biological agents can be mixed together prior to being applied to the stent; however, this is not required. The one or more polymers can be used to control the release of one or more biological agents by molecular diffusion and/or by one or more other mechanisms; however, this is not required. The thickness of the one or more polymer layers can be about 0.5-25µ; however, other coating thickness can be used. When one or more biological agents are controllably released from the stent, the time period the one or more biological agents are released from the stent can vary. Generally, one or more biological agent are released from the stent over a period of at least several days after the stent is inserted in the body of a patient. As can be appreciated, the time frame that one or more of the biological agents can be released from the stent can be longer or shorter. The one or more biological agents that are released from the stent can be controllably released and/or non-controllably released. The time period for the release of two or more biological agents from the stent can be the same or different. The type of the one or more biological agents used on the stent, the release rate of the one or more biological agents from the stent, and/or the concentration of the one or more biological agents being released from the stent during a certain time period is typically selected to deliver one or more biological agents to the area of treatment so as to increase the success of the stent (e.g., inhibit or prevent thrombosis, inhibit or prevent restenosis, vascular narrowing and/or in-stent restenosis after the stent has been implanted in a body passageway, etc.). The stent can be designed such that one or more biological agents are released from the stent for at least several minutes to at least several days after the stent is inserted in the body of a patient. As can be appreciated, the time frame that one or more of the biological agents can be released from the stent can be varied. The stent can be designed such that one or more biological agents are released from the stent so as to inhibit or prevent thrombosis after the stent has been implanted without the need for aggressive anti-platelet and/or anti-coagulation therapy. In one non-limiting design of stent, the stent releases one or more biological agents over a period of time after being inserted in the body so that no further anti-platelet and/or anti-coagulation therapy is required after the stent has been implanted. In another and/or alternative non-limiting design of stent, the stent releases one or more biological agents over a period of time after being inserted in the body so that no further anti-platelet and/or anti-coagulation therapy is required about one day to two weeks after the stent has been implanted. In still another and/or alternative non-limiting design of stent, the stent releases one or more biological agents over a period of time after being inserted in the body so that no further anti-platelet and/or anti-coagulation therapy is required about two weeks to one month after the stent has been implanted. The stent of the present invention can be used overcomes the requirement of past implanted stents to have the patient on aggressive anti-platelet and/or anti-coagulation therapy for months after the stent has been implanted in the patient.

When the one or more biological agents are used in combination with a non-porous polymer to controlled release of the one or more biological agents by molecular diffusion, the one or more polymers include, but are not limited to, polyamide, parylene C, parylene N, parylene F, poly(ethylene oxide), poly(ethylene glycol), poly(propylene oxide), silicone based polymers, polymers of methane, tetrafluoroethylene or tetramethyldisiloxane, a polymer derived from photopolymerizeable monomers and/or derivatives thereof. Such polymer can be coated on the stent by vapor deposition or plasma deposition; however, other or additional coating techniques can be used. The thickness of the one or more non-porous polymer layer, when applied by catalyst-free vapor deposition or plasma deposition is about 0.5-25µ; however, other coating thicknesses can be used.

The surface of the base structure of the stent can be treated to enhance the coating of the stent and/or to enhance the mechanical characteristics of the stent; however, this is not required. Such surface treatment techniques include, but are not limited to, cleaning, buffing, smoothing, etching (chemical etching, plasma etching, etc.), etc. When an etching process is used, various gasses can be used for such a surface treatment process such as, but not limited to, carbon dioxide, nitrogen, oxygen, Freon, helium, hydrogen, etc. The plasma etching process can be used to clean the surface of the stent, change the surface properties of the stent so as to affect the adhesion properties, lubricity properties, etc. of the surface of the stent. As can be appreciated, other or additional surface treatment processes can be used prior to the coating of one or more biological agents and/or polymers on the surface of the stent.

Figure 3:
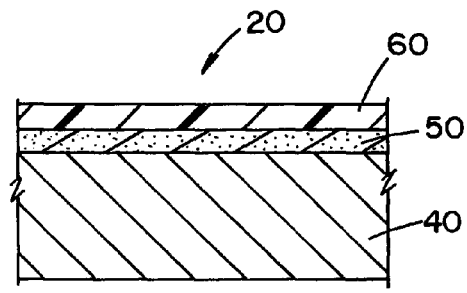
FIG. 3 is a cross-sectional view along line 3-3 of FIG. 2 illustrating one type of coating on a medical device.

As illustrated in FIGS. 3-6, various coating combinations can be used on the stent. Referring to FIG. 3, the base structure 40 of the stent includes a layer 50 of biological agent. The layer of biological agent can include one or more biological agents. In one non-limiting example, the biological agent includes trapidil, trapidil derivatives, warfarin (Coumadin) and/or derivatives, aspirin and/or derivatives, clopidogrel and/or derivatives, ticlopidine and/or derivatives, hirudin and/or derivatives, dipyridamole and/or derivatives, and/or heparin and/or low molecular weight heparin and/or derivatives. The one or more biological agents can also or alternatively include taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. A polymer layer 60 is coated on the top of layer 50. The polymer layer can include one or more polymers. The polymer layer can include one or more porous polymers and/or non-porous polymers, and/or one or more biostable and/or biodegradable polymers. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. In one non-limiting example, the polymer layer includes one or more non-porous polymers to at least partially control a rate of release by molecular diffusion of the one or more biological agents of layer 50 from stent 20. The one or more non-porous polymers can include, but is not limited to, parylene C, parylene N, parylene F and/or a parylene derivative.

Figure 4:
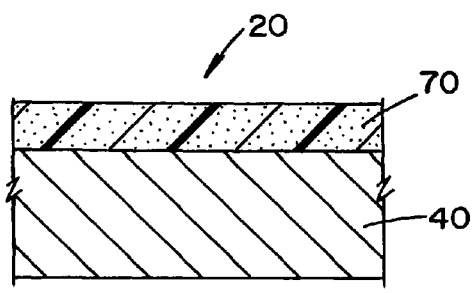
FIG. 4 is a cross-sectional view along line 3-3 of FIG. 2 illustrating another type of coating on a medical device.

As illustrated in FIG. 4, the base structure 40 of stent 20 includes a layer 70 of polymer and biological agent. Layer 70 can include one or more biological agents mixed with one or more polymers. In one non-limiting example, the biological agent includes trapidil, trapidil derivatives, warfarin (Coumadin) and/or derivatives, aspirin and/or derivatives, clopidogrel and/or derivatives, ticlopidine and/or derivatives, hirudin and/or derivatives, dipyridamole and/or derivatives, and/or heparin and/or low molecular weight heparin and/or derivatives. The one or more biological agents can also or alternatively include taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. The one or more polymers can include one or more porous and/or non-porous polymers, and/or one or more biostable and/or biodegradable polymers. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. In one non-limiting example, the one or more polymers included in layer 70 include a non-porous polymer to at least partially control a rate of release by molecular diffusion of the one or more biological agents in layer 70. The non-porous polymer can include, but is not limited to, parylene C, parylene N, parylene F and/or a parylene derivative.

Figure 5:
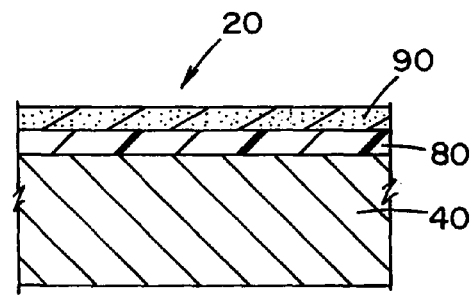
FIG. 5 is a cross-sectional view along line 3-3 of FIG. 2 illustrating another type of coating on a medical device.

As illustrated in FIG. 5, the base structure 40 of stent 20 includes a layer 80 of polymer. Layer 80 can include one or more porous polymers and/or non-porous polymers, and/or one or more biostable and/or biodegradable polymers. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. The one or more non-porous polymers, when used, can include, but is not limited to, parylene C, parylene N, parylene F and/or a parylene derivative. A layer 90 of one or more biological agents is coated on top of polymer layer 80. Polymer layer 8 can be used to facilitate in the securing of layer 90 to the stent; however, this is not required. In one non-limiting example, the biological agent includes trapidil, trapidil derivatives, warfarin (Coumadin) and/or derivatives, aspirin and/or derivatives, clopidogrel and/or derivatives, ticlopidine and/or derivatives, hirudin and/or derivatives, dipyridamole and/or derivatives, and/or heparin and/or low molecular weight heparin and/or derivatives. The one or more biological agents can also or alternatively include taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. The placement of a layer of biological agent on the top surface of the stent can provide a burst of biological agent in the treatment area (e.g., body passageway, etc.) after insertion of the stent. In one non-limiting example, the one or more biological agents include trapidil and/or derivatives thereof.

Figure 6:
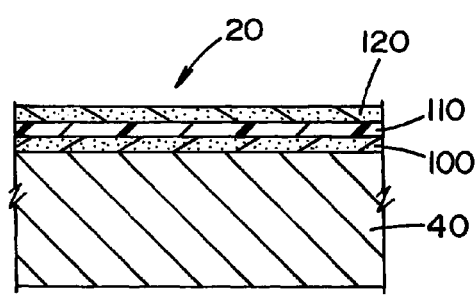
FIG. 6 is a cross-sectional view along line 3-3 of FIG. 2 illustrating another type of coating on a medical device.

As illustrated in FIG. 6, the base structure 40 of stent 20 includes a layer 100 of one or more biological agents. In one non-limiting example, the biological agent includes trapidil, trapidil derivatives, warfarin (Coumadin) and/or derivatives, aspirin and/or derivatives, clopidogrel and/or derivatives, ticlopidine and/or derivatives, hirudin and/or derivatives, dipyridamole and/or derivatives, and/or heparin and/or low molecular weight heparin and/or derivatives. The one or more biological agents can also or alternatively include taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. A polymer layer 110 is coated on the top of layer 100. The polymer layer can include one or more polymers. The polymer layer can include one or more porous polymers and/or non-porous polymers, and/or one or more biostable and/or biodegradable polymers. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. In one non-limiting example, the polymer layer includes one or more non-porous polymers to at least partially control a rate of release by molecular diffusion of the one or more biological agents of layer 100 from stent 20. The one or more non-porous polymers can include, but are not limited to, parylene C, parylene N, parylene F and/or a parylene derivative. A layer 120 of biological agent is coated on top of polymer layer 110. Layer 120 can include one or more biological agents. In one non-limiting example, the biological agent includes trapidil, trapidil derivatives, warfarin (Coumadin) and/or derivatives, aspirin and/or derivatives, clopidogrel and/or derivatives, ticlopidine and/or derivatives, hirudin and/or derivatives, dipyridamole and/or derivatives, and/or heparin and/or low molecular weight heparin and/or derivatives. The one or more biological agents can also or alternatively include taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. The placement of a layer of biological agent on the top surface of the stent provide can provide a burst of one or more biological agents in the treatment area (e.g., body passageway, etc.) after insertion of the stent. In one non-limiting example, the biological agent includes trapidil, trapidil derivatives, warfarin (Coumadin) and/or derivatives, aspirin and/or derivatives, clopidogrel and/or derivatives, ticlopidine and/or derivatives, hirudin and/or derivatives, dipyridamole and/or derivatives, and/or heparin and/or low molecular eight heparin and/or derivatives. The one or more biological agents can also or alternatively include taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. As can be appreciated, other combinations of polymer layer and layer of biological agent can be used on the stent. These other combinations are also encompassed within the scope of the present invention.

Figure 7:
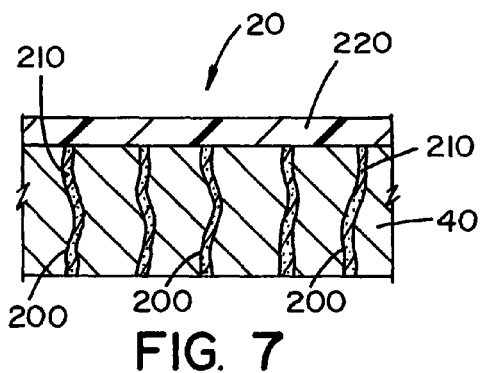
FIG. 7 is a cross-sectional view along line 3-3 of FIG. 2 illustrating pores in the body of the medical device containing a biological agent and a coating on the medical device.

Referring now to FIG. 7, the base structure 40 of stent 20 includes one or more surface structures and/or micro-structures 200. The one or more surface structures and/or microstructures can be formed in the base structure during the formation of the base structure and/or from the treatment of the base structure (e.g. etching, mechanical drill, laser cutting, water cutting, etc.) and/or from one or more micromachining processes. The one or more surface structures and/or micro-structures 200 are shown to include one or more biological agents 210; however, it can be appreciated that the one or more surface structures and/or micro-structures 200 can include a combination of one or more polymers and one or more biological agents, or only one or more polymers. In one non-limiting example, the biological agent includes trapidil, trapidil derivatives, warfarin (Coumadin) and/or derivatives, aspirin and/or derivatives, clopidogrel and/or derivatives, ticlopidine and/or derivatives, hirudin and/or derivatives, dipyridamole and/or derivatives, and/or heparin and/or low molecular eight heparin and/or derivatives. The one or more biological agents can also or alternatively include taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. The size of the one or more surface structures and/or micro-structures can be used to at least partially control the rate of release of the one or more biological agents and/or polymers from the one or more surface structures and/or micro-structures. A polymer layer 220 is coated on the top surface of the base structure 40. The polymer layer can include one or more polymers. The polymer layer can include one or more porous polymers and/or non-porous polymers, and/or one or more biostable and/or biodegradable polymers. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. In one non-limiting example, the polymer layer includes one or more non-porous polymers to at least partially control a rate of release by molecular diffusion of the one or more biological agents in the one or more surface structures and/or micro-structures 200. The one or more non-porous polymers can include, but are not limited to, parylene C, parylene N, parylene F and/or a parylene derivative.

Figure 8:
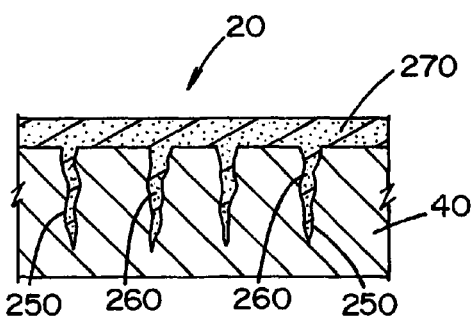
FIG. 8 is a cross-sectional view along line 3-3 of FIG. 2 illustrating pores in the body of the medical device containing a biological agent and a biological agent coating on the medical device.

Referring now to FIG. 8, the base structure 40 of stent 20 includes one or more surface structures and/or micro-structures 250. The one or more surface structures and/or micro-structures can be formed in the base structure during the formation of the base structure and/or from the treatment of the base structure (e.g. etching, mechanical drill, laser cutting, water cutting, etc.) and/or from one or more micromachining processes. The one or more surface structures and/or micro-structures 250 are shown to include one or more biological agents 260; however, it can be appreciated that the one or more surface structures and/or micro-structures 250 can include a combination of one or more polymers and one or more biological agents, or only one or more polymers. In one non-limiting example, the biological agent includes trapidil, trapidil derivatives, warfarin (Coumadin) and/or derivatives, aspirin and/or derivatives, clopidogrel and/or derivatives, ticlopidine and/or derivatives, hirudin and/or derivatives, dipyridamole and/or derivatives, and/or heparin and/or low molecular weight heparin and/or derivatives. The one or more biological agents can also or alternatively include taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. The size of the one or surface structures and/or micro-structures can be used to at least partially control the rate of release of the one or more biological agents and/or polymers from the one or more surface structures and/or micro-structures. A layer 270 of biological agents. In one non-limiting example, the biological agent includes trapidil, trapidil derivatives, warfarin (Coumadin) and/or derivatives, aspirin and/or derivatives, clopidogrel and/or derivatives, ticlopidine and/or derivatives, hirudin and/or derivatives, dipyridamole and/or derivatives, and/or heparin and/or low molecular eight heparin and/or derivatives. The one or more biological agents can also or alternatively include taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. The placement of a layer of biological agent on the top surface of the stent can provide a burst of one or more biological agent in the treatment area after insertion of the stent. In one non-limiting example, the biological agent includes trapidil, trapidil derivatives, warfarin (Coumadin) and/or derivatives, aspirin and/or derivatives, clopidogrel and/or derivatives, ticlopidine and/or derivatives, hirudin and/or derivatives, dipyridamole and/or derivatives, and/or heparin and/or low molecular weight heparin and/or derivatives. The one or more biological agents can also or alternatively include taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. As can be appreciated, the one or more biological agents of layer 270 and in the one or more surface structures and/or micro-structures 250 can be the same or different.

Figure 9:
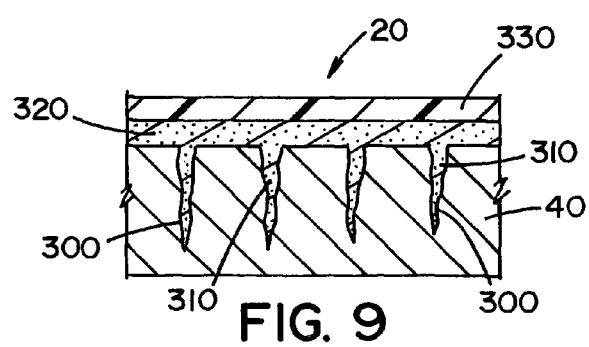
FIG. 9 is a cross-sectional view along line 3-3 of FIG. 2 illustrating pores in the body of the medical device containing a biological agent and a biological agent coating on the medical device and a polymer coating over the biological agent.

Referring now to FIG. 9, the base structure 40 of stent 20 includes one or more surface structures and/or micro-structures 300. The one or more surface structures and/or micro-structures can be formed in the base structure during the formation of the base structure and/or from the treatment of the base structure (e.g. etching, mechanical drill, laser cutting, water cutting, etc.) and/or from one or more micromachining processes. The one or more surface structures and/or micro-structures 300 are shown to include one or more biological agents 310; however, it can be appreciated that the one or more surface structures and/or micro-structures 300 can include a combination of one or more polymers and one or more biological agents, or only one or more polymers. In one non-limiting example, the biological agent includes trapidil, trapidil derivatives, warfarin (Coumadin) and/or derivatives, aspirin and/or derivatives, clopidogrel and/or derivatives, ticlopidine and/or derivatives, hirudin and/or derivatives, dipyridamole and/or derivatives, and/or heparin and/or low molecular weight heparin and/or derivatives. The one or more biological agents can also or alternatively include taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. The size of the one or more surface structures and/or micro-structures can be used to at least partially control the rate of release of the one or more biological agents and/or polymers from the one or more surface structures and/or micro-structures. A layer 320 of biological agent is coated on the top surface of the base structure. Layer 320 can include one or more biological agents. In one non-limiting example, the biological agent includes trapidil, trapidil derivatives, warfarin (Coumadin) and/or derivatives, aspirin and/or derivatives, clopidogrel and/or derivatives, ticlopidine and/or derivatives, hirudin and/or derivatives, dipyridamole and/or derivatives, and/or heparin and/or low molecular weight heparin and/or derivatives. The one or more biological agents can also or alternatively include taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. As can be appreciated, the one or more biological agents of layer 320 and in the one or more surface structures and/or micro-structures 300 can be the same or different. A polymer layer 330 is coated on the top surface of the layer 310 of biological agent. The polymer layer can include one or more polymers. The polymer layer can include one or more porous polymers and/or non-porous polymers, and/or one or more biostable and/or biodegradable polymers. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. In one non-limiting example, the polymer layer includes one or more non-porous polymers to at least partially control a rate of release by molecular diffusion of the one or more biological agents in the one or more surface structures and/or micro-structures 300 and/or in layer 310. The one or more non-porous polymers can include, but are not limited to, parylene C, parylene N, parylene F and/or a parylene derivative. As can be appreciated, a layer that includes one or more biological agents, not shown, can be coated on layer 320 to provide a burst of one or more biological agent in the treatment area after insertion of the stent. As can also be appreciated, other combinations of polymer layer and layer of biological agent can be used on the medical. These other combinations are also encompassed within the scope of the present invention.

Figure 10:
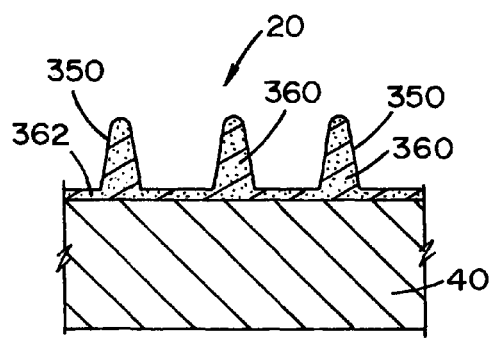
FIG. 10 is a cross-sectional view along line 3-3 of FIG. 2 illustrating micro-needles on the surface of the medical device that are formed of a biological agent.

Referring now to FIG. 10, the base structure 40 of stent 20 includes one or more needles or micro-needles 350. The one or more needles or micro-needles are formed on the surface of the base structure. The one or more needles or micro-needles are formed from one or more biological agents and/or one or more polymer 360. A layer 362 of biological agent and/or polymer is also formed on the surface of the base structure. In one non-limiting example, the one or more needles or micro-needles 350 are formed from one or more biological agents that include trapidil, trapidil derivatives, warfarin (Coumadin) and/or derivatives, aspirin and/or derivatives, clopidogrel and/or derivatives, ticlopidine and/or derivatives, hirudin and/or derivatives, dipyridamole and/or derivatives, and/or heparin and/or low molecular weight heparin and/or derivatives. The one or more biological agents can also or alternatively include taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. In this non-limiting example, layer 362 is also formed from one or more biological agents that include trapidil, trapidil derivatives, warfarin (Coumadin) and/or derivatives, aspirin and/or derivatives, clopidogrel and/or derivatives, ticlopidine and/or derivatives, hirudin and/or derivatives, dipyridamole and/or derivatives, and/or heparin and/or low molecular weight heparin and/or derivatives. The one or more biological agents can also or alternatively include taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. As can be appreciated, the one or more biological agents in layer 362 and forming the one or more needles or micro-needles 350 can be the same or different. The use of one or more biological agents to coat the top surface of the base structure and/or to form one or more needles or micro-needles can provide a burst of one or more biological agent in the treatment area (e.g., body passageway, etc.) after insertion of the stent. In another and/or alternative non-limiting example, the one or more needles or micro-needles 350 are formed from one or more biological agents that include trapidil, trapidil derivatives, warfarin (Coumadin) and/or derivatives, aspirin and/or derivatives, clopidogrel and/or derivatives, ticlopidine and/or derivatives, hirudin and/or derivatives, dipyridamole and/or derivatives, and/or heparin and/or low molecular weight heparin and/or derivatives. The one or more biological agents can also or alternatively include taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. In this non-limiting example, layer 362 is formed from one or more polymers. The polymer layer can include one or more polymers. The polymer layer can include one or more porous polymers and/or non-porous polymers, and/or one or more biostable and/or biodegradable polymers. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. When the one or more polymers are non-porous polymers, the one or more non-porous polymers can include, but are not limited to, parylene C, parylene N, parylene F and/or a parylene derivative. The use of one or more biological agents to form one or more needles or micro-needles can provide a burst of one or more biological agent in the treatment area (e.g., body passageway, etc.) after insertion of the stent. In still another and/or alternative non-limiting example, the one or more needles or micro-needles 350 are formed from one or more polymers. The polymer layer can include one or more polymers. The polymer layer can include one or more porous polymers and/or non-porous polymers, and/or one or more biostable and/or biodegradable polymers. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. When the one or more polymers are non-porous polymers, the one or more non-porous polymers can include, but are not limited to, parylene C, parylene N, parylene F and/or a parylene derivative. In this non-limiting example, layer 362 is formed from one or more biological agents that include trapidil, trapidil derivatives, warfarin (Coumadin) and/or derivatives, aspirin and/or derivatives, clopidogrel and/or derivatives, ticlopidine and/or derivatives, hirudin and/or derivatives, dipyridamole and/or derivatives, and/or heparin and/or low molecular weight heparin and/or derivatives. The one or more biological agents can also or alternatively include taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. The use of one or more biological agents to form layer 362 can provide a burst of one or more biological agent in the treatment area (e.g., body passageway, etc.) after insertion of the stent; however, this is not required.

Figure 11:
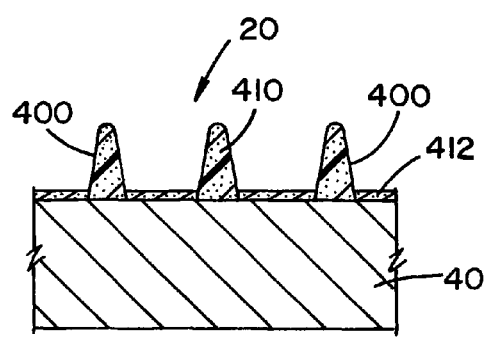
FIG. 11 is a cross-sectional view along line 3-3 of FIG. 2 illustrating micro-needles on the surface of the medical device that are formed of a biological agent and polymer.

Referring now to FIG. 11, the base structure 40 of stent 20 includes one or more needles or micro-needles 400. The one or more needles or micro-needles are formed on the surface of the base structure. The one or more needles or micro-needles are formed from one or more biological agents and one or more polymers 410. A layer 412 of biological agent and/or polymer is also formed on the surface of the base structure. As can be appreciated, the composition of layer 412 and forming the composition of the one or more needles or micro-needles 400 can be the same or different. In one non-limiting example, the one or more biological agents that at least partially forms layer 412 and/or the one or more needles or micro-needles 400 include trapidil, trapidil derivatives, warfarin (Coumadin) and/or derivatives, aspirin and/or derivatives, clopidogel and/or derivatives, ticlopidine and/or derivatives, hirudin and/or derivatives, dipyridamole and/or derivatives, and/or heparin and/or low molecular weight heparin and/or derivatives. The one or more biological agents can also or alternatively include taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. The one or more polymers that at least partially form layer 412 and/or the one or more needles or micro-needles 400 can include one or more porous and/or non-porous polymers, and/or one or more biostable and/or biodegradable polymers. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. In one non-limiting example, the one or more polymers that at least partially form layer 412 and/or the one or more needles or micro-needles 400 include a non-porous polymer to at least partially control a rate of release by molecular diffusion of the one or more biological agents that are mixed with the polymer. The inclusion of one or more biological agents in the one or more needles or micro-needles can provide controlled release of biological agent in the treatment area (e.g., body passageway, etc.) after insertion of the stent; however, this is not required. The use of one or more biological agents to form layer 412 and/or one or more needles or micro-needles 400 can provide a burst of one or more biological agent in the treatment area (e.g., body passageway, etc.) after insertion of the stent; however, this is not required.

Figure 12:
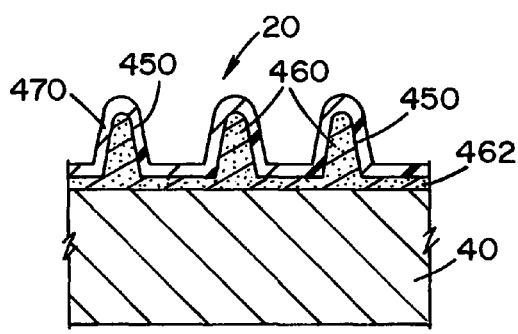
FIG. 12 is a cross-sectional view along line 3-3 of FIG. 2 illustrating micro-needles on the surface of the medical device that are formed of a biological agent and coated with a polymer.

Referring now to FIG. 12, FIG. 12 is a modification of the arrangement illustrated in FIG. 10. In FIG. 12, a coating 470, that is formed of one or more polymers and/or biological agents is placed over one or more needles or micro-needles 450 and layer 462. Specifically, the base structure 40 of stent 20 includes one or more needles or micro-needles 450. The one or more needles or micro-needles are formed on the surface of the base structure. The one or more needles or micro-needles are formed from one or more biological agents and/or polymers 460. A layer 462 of biological agent and/or polymer is also formed on the surface of the base structure. The composition of layer 462 and one or more needles or micro-needles can be the same or different. In one non-limiting example, the one or more biological agents that can at least partially form layer 463 and/or one or more needles or micro-needles 450 include trapidil, trapidil derivatives, warfarin (Coumadin) and/or derivatives, aspirin and/or derivatives, clopidogrel and/or derivatives, ticlopidine and/or derivatives, hirudin and/or derivatives, dipyridamole and/or derivatives, and/or heparin and/or low molecular weight heparin and/or derivatives. The one or more biological agents can also or alternatively include taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CS F, GM-CSF derivatives, or combinations thereof. The one or more polymers that can at least partially form layer 463 and/or one or more needles or micro-needles include one or more porous polymers and/or non-porous polymers, and/or one or more biostable and/or biodegradable polymers. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. In one non-limiting example, the one or more polymers that can at least partially form layer 463 and/or one or more needles or micro-needles 450 include one or more non-porous polymer such as, but not limited to, parylene C, parylene N, parylene F and/or a parylene derivative. The one or more non-porous polymers can be used to at least partially control a rate of release by molecular diffusion of the one or more biological agents in layer 463 and/or in the one or more needles or micro-needles 450; however, this is not required. Layer 470 that is coated on the top of the one or more needles or micro-needles and layer 462 includes one or more biological agents and/or polymers. In one non-limiting example, the one or more biological agents that can at least partially form layer 470 include trapidil, trapidil derivatives, warfarin (Coumadin) and/or derivatives, aspirin and/or derivatives, clopidogrel and/or derivatives, ticlopidine and/or derivatives, hirudin and/or derivatives, dipyridamole and/or derivatives, and/or heparin and/or low molecular weight heparin and/or derivatives. The one or more biological agents can also or alternatively include taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. In one non-limiting example, the one or more polymers that can at least partially form layer 470 include one or more porous and/or non-porous polymers, and/or one or more biostable and/or biodegradable polymers. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. When the one or more polymers include one or more non-porous polymers, such non-porous polymer can include, but is not limited to, parylene C, parylene N, parylene F and/or a parylene derivative. The one or more non-porous polymers can be used to at least partially control a rate of release by molecular diffusion of the one or more biological agents in layer 463, layer 470 and/or in the one or more needles or micro-needles 450; however, this is not required. When one or more biological agents at least partially form layer 470 and/or are coated on layer 470, not shown, the one or more biological agents can provide a burst of one or more biological agent in the treatment area (e.g., body passageway, etc.) after insertion of the stent; however, this is not required.

Figure 13:
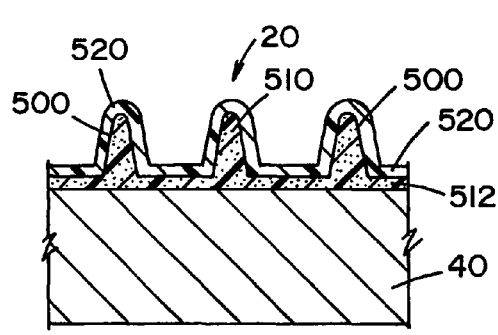
FIG. 13 is a cross-sectional view along line 3-3 of FIG. 2 illustrating micro-needles on the surface of the medical device that are formed of a biological agent and polymer and coated with a polymer.

Referring now to FIG. 13, FIG. 13 is a modification of the arrangement illustrated in FIG. 11. In FIG. 13, a coating 520, that is formed of one or more polymers and/or biological agents is placed over one or more needles or micro-needles 500 and layer 512. The composition of layer 520 and layer 512 and/or one or more needles or micro-needles can be the same or different. Specifically, the base structure 40 of stent 20 includes one or more needles or micro-needles 500. The one or more needles or micro-needles are formed on the surface of the base structure. The one or more needles or micro-needles are formed from a mixture of one or more biological agents and one or more polymers 510. A layer 512 of biological agent and polymer is also formed on the surface of the base structure. As can be appreciated, layer 512 and/or one or more needles or micro-needles 500 can be formed only of one or more polymers or one or more biological agents. The composition of layer 512 and one or more needles or micro-needles 500 can be the same or different. In one non-limiting example, the one or more biological agents that can at least partially form layer 512 and/or one or more needles or micro-needles 500 include trapidil, trapidil derivatives, warfarin (Coumadin) and/or derivatives, aspirin and/or derivatives, clopidogrel and/or derivatives, ticlopidine and/or derivatives, hirudin and/or derivatives, dipyridamole and/or derivatives, and/or heparin and/or low molecular weight heparin and/or derivatives. The one or more biological agents can also or alternatively include taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. The one or more polymers that can at least partially form layer 512 and/or one or more needles or micro-needles 500 include one or more porous polymers and/or non-porous polymers, and/or one or more biostable and/or biodegradable polymers. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. In one non-limiting example, the one or more polymers that can at least partially form layer 512 and/or one or more needles or micro-needles 500 include one or more non-porous polymers such as, but not limited to, parylene C, parylene N, parylene F and/or a parylene derivative. The one or more non-porous polymers can be used to at least partially control a rate of release by molecular diffusion of the one or more biological agents in layer 512 and/or in the one or more needles or micro-needles 500; however, this is not required. In one non-limiting example, the one or more polymers that can at least partially form layer 520 include one or more porous and/or non-porous polymers, and/or one or more biostable and/or biodegradable polymers. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. When the one or more polymers include one or more non-porous polymers, such non-porous polymer can include, but not limited to, parylene C, parylene N, parylene F and/or a parylene derivative. The one or more non-porous polymers can be used to at least partially control a rate of release by molecular diffusion of the one or more biological agents in layer 512, layer 520 and/or in the one or more needles or micro-needles 500; however, this is not required. When one or more biological agents at least partially forms layer 520 and/or are coated on layer 520, not shown, the one or more biological agents can provide a burst of one or more biological agent in the treatment area (e.g., body passageway, etc.) after insertion of the stent; however, this is not required.

Figure 14:
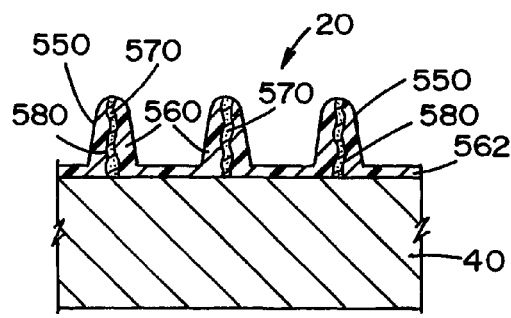
FIG. 14 is a cross-sectional view along line 3-3 of FIG. 2 illustrating micro-needles on the surface of the medical device that are formed of a polymer and includes an internal cavity that includes a biological agent.

Referring now to FIG. 14, FIG. 14 is another modification of the arrangement illustrated in FIG. 11. In FIG. 14, one or more internal channels 570 are formed in one or more needles or micro-needles 550. The one or more internal channels 570 can include one or more biological agent and/or polymers. Specifically, the base structure 40 of stent 20 includes one or more needles or micro-needles 550. The one or more needles or micro-needles are formed on the surface of the base structure. The one or more needles or micro-needles are formed from one or more polymers and/or biological agents 560. A layer 562 of polymer and/or biological agent is also formed on the surface of the base structure. The composition of layer 562 and one or more needles or micro-needles can be the same or different. The one or more polymers that can at least partially form layer 562 and/or one or more needles or micro-needles 550 include one or more porous polymers and/or non-porous polymers, and/or one or more biostable and/or biodegradable polymers. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. In one non-limiting example, the one or more polymers that can at least partially form layer 562 and/or one or more needles or micro-needles 550 include one or more non-porous polymers such as, but not limited to, parylene C, parylene N, parylene F and/or a parylene derivative. The one or more non-porous polymers can be used to at least partially control a rate of release by molecular diffusion of the one or more biological agents in layer 562, in the one or more needles or micro-needles 550, and/or in one or more internal channels 570; however, this is not required. One or more of the needles or micro-needles 550 include an internal channel 570. The internal channel is illustrated as including one or more biological agents 580; however, it can be appreciated that one or more channels can include a mixture of one or more polymers and/or biological agents, or only one or more polymers. In one non-limiting example, the one or more biological agents includes trapidil, trapidil derivatives, warfarin (Coumadin) and/or derivatives, aspirin and/or derivatives, clopidogrel and/or derivatives, ticlopidine and/or derivatives, hirudin and/or derivatives, dipyridamole and/or derivatives, and/or heparin and/or low molecular weight heparin and/or derivatives. The one or more biological agents can also or alternatively include taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. The top opening of the channel enables delivery of one or more biological agents directly into treatment area (e.g., a wall of a body passageway or organ, etc.). The one or more biological agents in internal channel 570 can pass through and/or molecularly diffuse through the one or more polymers that at least partially form the one or more needles or micro-needles; however, this is not required. The release of the one or more biological agents through the one or more polymers that at least partially forms the one or more needles or micro-needles can be a controlled or an uncontrolled release rate. As can be appreciated, a layer of biological agent, not shown, can be coated on one or more needles or micro-needles 550. The layer of biological agent could include one or more biological agents. The placement of the layer of biological agent on the one or more needles or micro-needles 550 can provide a burst of one or more biological agents in the treatment area; however, this is not required. As can be appreciated, other combinations of polymer layer and/or layer of biological agent can be used on the stent. As can also or alternatively be appreciated, a layer of polymer, not shown, can be coated on one or more needles or micro-needles 550. The layer of polymer could include one or more polymers. The placement of the layer of polymer on the one or more needles or micro-needles 550 can be used to a) at least partially control a release rate of one or more biological agents from the stent, and/or 2) provide structural support and/or protection to one or more needles or micro-needles. As can be appreciated, the polymer layer, when used, can have other or additional functions. These other combinations are also encompassed within the scope of the present invention.

Figure 17:
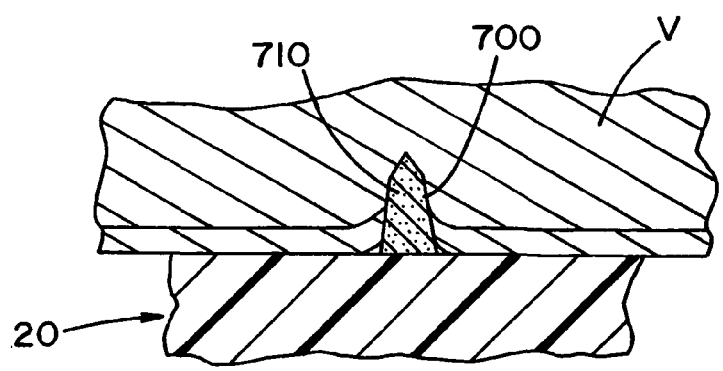

Referring now to FIG. 17, there is illustrated an enlarged portion of a surface of a stent 20 which includes a surface needle, micro-needle or other type of structure or microstructure 700. The needle is shown to include at least one biological agent 710; however, the needle can also or alternatively include one or more polymers, adhesives, etc. The stent, when in the form of a stent, is illustrated as being in an expanded state. When the stent is inserted or expanded in a treatment area, the needle 700 on the outer surface of the stent engages and/or at least partially penetrates into blood vessel or organ V. When the needle includes one or more biological agents, the one or more biological agents are at least partially locally applied to a treatment area. This can be a significant advantage over system wide treatment with one or more biological agents. The local treatment with one or more biological agent via the needle can more effectively and/or efficiently direct the desired agents to a treated area. The release of one or more biological agents from the needle can be controlled, if desired, to direct the desired amount of one or more biological agents to a treated area over a desired period of time. When the stent is expanded in a blood vessel, the one or more needles enable local delivery of one or more biological agents into the wall of the blood vessel. This local delivery is especially advantageous in large and/or thick blood vessels wherein system wide drug treatment is not very effective. In addition, the local delivery of biological agent by the needle directly into the blood vessel can be more effective than only releasing the biological agent from the surface of the stent since diffusion from the surface of the stent to the larger and/or thicker blood vessel may not be as effective as direct delivery by the needles to the blood vessel. The one or more needles on the stent surface can also or alternatively be used to facilitate in securing the stent to the treatment area during the expansion and/or insertion of the stent in a treatment area.

Referring now to FIG. 15, there is provided a surgical graft 600. The surgical graft is typically at least partially formed of a flexible material. The material used to form the surgical graft is selected to withstand the manufacturing process that is needed to be accomplished in order to produce the surgical graft. These manufacturing processes can include, but are not limited to, ion beam deposition or implantation, sputter coating, vacuum deposition and/or other coating processes. One non-limiting material is Gortex; however, other or additional materials can be used (e.g., polyethylene tetraphthlate (Dacron), expanded polytetrafluoroethylene (e.g., Gortex, Impra, etc.), etc. The surgical graft can be used in a variety of body passageways. One non-limiting use of the surgical graft is to graft to or replace a portion of a damaged blood vessel. The surgical graft 600 has a generally tubular shape; however, many other shapes can be used. As best illustrated in FIG. 16, the surgical graft includes a body portion 610. The inner surface 620 of the body portion includes a plurality of threads 630 extending from the inner surface 630 of the body portion. A layer 640 including one or more biological agents and/or polymers is applied to the inner surface of the body portion. As illustrated in FIG. 16, layer 640 only partially encapsulates threads 630; however, this is not required. It can be appreciated that layer 640 is applied in sufficient quantity to fully encapsulate threads 630. In one non-limiting example, the one or more biological agents in layer 640 include trapidil, trapidil derivatives, warfarin (Coumadin) and/or derivatives, aspirin and/or derivatives, clopidogrel and/or derivatives, ticlopidine and/or derivatives, hirudin and/or derivatives, dipyridamole and/or derivatives, and/or heparin and/or low molecular weight heparin and/or derivatives. The one or more biological agents can also or alternatively include taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. As can be appreciated, layer 640 can include a combination of biological agent and polymer, or only a polymer. Referring again to FIG. 16, a layer 650 is coated on layer 640. Layer 650 can include one or more polymers. The layer can include one or more porous and/or non-porous polymers and/or one or more biostable and/or biodegradable polymers. Non-limiting examples of one or more polymers that can be used include, but are not limited to, parylene, parylene C, parylene N, parylene F, PLGA, PEVA, PLA, PBMA, POE, PGA, PLLA, PAA, PEG, chitosan and/or derivatives of one or more of these polymers. In one non-limiting example, the polymer layer includes one or more non-porous polymers to at least partially control a rate of release by molecular diffusion of the one or more biological agents in layer 640 and/or layer 650. The one or more non-porous polymers can include, but are not limited to, parylene C, parylene N, parylene F and/or a parylene derivative. Layer 650 is shown to only partially encapsulate threads 630. As can be appreciated, sufficient amount of layer 650 can be used to fully encapsulate thread 630. As can be appreciated, a layer of biological agent, not shown, can be coated on layer 650. The layer of biological agent could include one or more biological agents. The placement of the layer of biological agent on the top surface of layer 650 can provide a burst of one or more biological agents in the treatment area (e.g., body passageway, etc.) after insertion of the surgical graft; however, this is not required. As can be appreciated, other combinations of polymer layer and layer of biological agent can be used on the surgical graft. Non-limiting examples of such combinations are illustrated in FIGS. 3-14. These other combination are also encompassed within the scope of the present invention.

The following is a non-limiting example of the manufacture of a medical device in the form of a stent in accordance with the present invention. A medical device structure in the form of a stent for use in a body passageway (e.g., vascular system, etc.) is selected. The base structure is formed of a durable, biostable metal material. As can be appreciated, the base structure can be made of a nonmetallic material and/or a biodegradable material. The surface of the base structure of the medical device is plasma etched and/or cleaned. A porous or non-porous polymer layer is applied to the etched surface of the base structure. One or more biological agents are then applied to the surface of the polymer layer. As can be appreciated, the one or more biological agents can be applied to the surface of the stent prior to applying the porous or non-porous polymer layer. At least one non-porous polymer layer is applied over the one or more layers of biological agents so as to at least partially control the rate of release of the one or more biological agents by molecular diffusion through the non-porous polymer layer. The one or more non-porous polymers can include, but are not limited to, parylene C, parylene N, parylene F and/or a parylene derivative. A layer of biological agents can be applied over the final non-porous polymer layer for an additional fast release of the biological agent; however, this is not required. The at least one non-porous layer is applied via polymerization from a monomer vapor which is solvent or catalyst-free and is self curing. At least one layer of the biological agent can be deposited on the surface of the base structure or polymer by a number of methods such as, but not limited to, dipping, rolling, brushing, spraying, particle atomization, sonication or the like. Sonication can be used to deposit one or more biological agents and/or polymers on the surface of the base structure. Sonication involves the application of ultrasonic waves to a stream of fluid that may or may not contain the biological agent and/or the polymer material. The fluid can include, but is not limited to, methanol, ethanol, isopropanol, acetone, water, saline, or any other organic or inorganic solvent. The sonicated stream is broken into droplets of the fluid that may vary in size from less than 1 micron to several microns in diameter or more. The size of the droplets can be varied by controlling the frequency of the sonicating device. The droplets can be applied to the medical device evenly or in various thickness configurations through controlling the rotation of the medical device. The one or more biological agents that are applied to the medical device can include, but are not limited to, trapidil, trapidil derivatives, warfarin (Coumadin) and/or derivatives, aspirin and/or derivatives, clopidogrel and/or derivatives, ticlopidine and/or derivatives, hirudin and/or derivatives, dipyridamole and/or derivatives, and/or heparin and/or low molecular weight heparin and/or derivatives. The one or more biological agents can also or alternatively include taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof.

The medical device of the present invention can be used in conjunction with other biological agents. For instance, the success of the medical device can be enhanced by infusing, injecting and/or consuming orally the same and/or different biological agents that are being released from the medical device. The introduction of one or more biological agents from a source other than the medical device can have an additive or synergistic effect which can enhance the success of the medical device. Solid dosage forms of one or more biological agents for oral administration can be used. Such solid forms can include, but are not limited to, capsules, tablets, effervescent tablets, chewable tablets, pills, powders, sachets, granules and gels. In such solid dosage forms, the one or more biological agents can be admixed with at least one filler material such as, but not limited to, sucrose, lactose or starch. Such dosage forms can also comprise, as in normal practice, additional substances such as, but not limited to, inert diluents (e.g., lubricating agents, etc.). When capsules, tablets, effervescent tablets or pills are used, the dosage form can also include buffering agents. Soft gelatin capsules can be prepared to contain a mixture of the biological agent in combination with vegetable oil or other types of oil. Hard gelatin capsules can contain granules of the biological agent in combination with a solid carrier such as, but not limited to, lactose, potato starch, corn starch, cellulose derivatives of gelatin, etc. Tablets and pills can be prepared with enteric coatings for additional time release characteristics. Liquid dosage forms of the biological agent for oral administration can include pharmaceutically acceptable emulsions, solutions, suspensions, syrups, elixirs, etc.

It will thus be seen that the objects set forth above, among those made apparent from the preceding description, are efficiently attained, and since certain changes may be made in the constructions set forth without departing from the spirit and scope of the invention, it is intended that all matter contained in the above description and shown in the accompanying drawings shall be interpreted as illustrative and not in a limiting sense. The invention has been described with reference to preferred and alternate embodiments. Modifications and alterations will become apparent to those skilled in the art upon reading and understanding the detailed discussion of the invention provided herein. This invention is intended to include all such modifications and alterations insofar as they come within the scope of the present invention. It is also to be understood that the following claims are intended to cover all of the generic and specific features of the invention herein described and all statements of the scope of the invention, which, as a matter of language, might be said to fall therebetween.

We claim:

1. A method of treating a damaged vascular system of a patient with a medical device without having to use long term body-wide aggressive anti-platelet and/or anti-coagulation therapy after the implantation of the medical device comprising:
   a) identifying a damaged region of the vascular system;
   b) opening a section or replacing a section of said damaged region of the vascular system by or with said medical device, said medical device being a stent or surgical graft, said medical device including a biological agent, said biological agent inhibiting or preventing thrombosis, said biological agent including two or more agents selected from the group consisting of trapidil, trapidil derivatives, aspirin, aspirin derivatives, dipyridamole, dipyridamole derivatives, heparin, heparin derivatives, warfarin, warfarin derivatives, clopidogrel, clopidogrel derivatives, ticlopidine, ticlopidine derivatives, and hirudin, hirudin derivatives said medical device includes at least one polymer layer having a coating thickness, a molecular weight, a molecular structure or combinations thereof to at least partially controllably release at least one of said biological agent, said polymer designed to release said biological agent from said medical device for at least about one day after said medical device is introduced into or on the body of a patient, said polymer layer includes parylene, a parylene derivative, chitosan, a chitosan derivative, PLGA, a PLGA derivative, PLA, a PLA derivative, PEVA, a PEVA derivative, PBMA, a PBMA derivative, POE, POE derivative, PGA, PGA derivative, PLLA, PLLA derivative, PAA, PAA derivative, PEG, PEG derivative, or combinations thereof, said medical device includes a plurality of micro-structures, surface structures or combinations thereof, said plurality of micro-structures, surface structures or combinations thereof include a needle, a micro-needle or combinations thereof that extends upwardly from an outer surface of said medical device; and,
   c) allowing said patient to recover from the surgical procedure with no use or short term use of less than about two months of post operative body-wide anti-platelet and/or anti-coagulation therapy.

2. The method as defined in claim 1, wherein said short term use is less than about forty days.

3. The method as defined in claim 2, wherein said short term use is less than about one week.

4. The method as defined in claim 3, wherein said short term use is less than about two days.

5. The method as defined in claim 2, wherein said biological agent consists of two or more agents selected from the group trapidil, trapidil derivatives, aspirin, aspirin derivatives, dipyridamole, dipyridamole derivatives, heparin, heparin derivatives, or combinations thereof.

6. The method as defined in claim 5, wherein said one or more biological agents include trapidil, trapidil derivatives, or combinations thereof.

7. The method as defined in claim 6, wherein said one or more biological agents additionally include cytochalasin, cytochalasin derivatives, paclitaxel, paclitaxel derivatives, rapamycin, rapamycin derivatives, GM-CSF, GM-CSF derivatives, or combinations thereof.

8. The method as defined in claim 7, including the step of expanding said medical device until said medical device at least partially engages an inner surface of a body passageway of said vascular system and causes said plurality of needles, micro-needles, or combinations thereof to at least partially penetrate into said body passageway.

9. The method as defined in claim 8, wherein said plurality of needles, micro-needles, or combinations thereof includes at least one biological agent.

10. The method as defined in claim 9, wherein said at least one biological agent included in said plurality of needles, micro-needles or combinations thereof at east partially inhibits thrombosis.

11. The method as defined in claim 1, wherein said biological agent consists of two or more agents selected from the group trapidil, trapidil derivatives, aspirin, aspirin derivatives, dipyridamole, dipyridamole derivatives, heparin, heparin derivatives, or combinations thereof.

12. The method as defined in claim 11, wherein said one or more biological agents include trapidil, trapidil derivatives, or combinations thereof.

13. The method as defined in claim 12, wherein said one or more biological agents additionally include cytochalasin, cytochalasin derivatives, paclitaxel, paclitaxel derivatives, rapamycin, rapamycin derivatives, GM-CSF, GM-CSF derivatives, or combinations thereof.

14. The method as defined in claim 1, including the step of expanding said medical device until said medical device at least partially engages an inner surface of a body passageway of said vascular system and causes said plurality of needles, micro-needles, or combinations thereof to at least partially penetrate into said body passageway.

15. The method as defined in claim 1, wherein said plurality of needles, micro-needles, or combinations thereof includes at least one biological agent.

16. A method of treating a damaged vascular system of a patient with a medical device without having to use long term body-wide aggressive anti-platelet therapy, anti-coagulation therapy, and combinations thereof after the implantation of the medical device comprising:
   a) identifying a damaged region of the vascular system;
   b) opening a section or replacing a section of said damaged region of the vascular system by or with said medical device, said medical device being a stent or surgical graft, said medical device including a biological agent and a plurality of microstructures, said biological agent inhibiting or preventing thrombosis, said biological agent including at least one agent selected from the group consisting of warfarin, warfarin derivatives, aspirin, aspirin derivatives, clopidogel, clopidogel derivatives, ticlopidine, ticlopidine derivatives, hirudin, hirudin derivatives, dipyridamole, dipyridamole derivatives, heparin, heparin derivatives, low molecular weight heparin, low molecular weight heparin derivatives, and combinations thereof, said medical device includes at least one polymer layer having a coating thickness, a molecular weight, a molecular structure or combinations thereof to at least partially controllably release at least one of said biological agent, said polymer designed to release said biological agent from said medical device for at least about one day after said medical device is introduced into or on the body of a patient, said polymer layer includes parylene, a parylene derivative, chitosan, a chitosan derivative, PLGA, a PLGA derivative, PLA, a PLA derivative, PEVA, a PEVA derivative, PBMA, a PBMA derivative, POE, POE derivative, PGA, PGA derivative, PLLA, PLLA derivative, PAA, PAA derivative, PEG, PEG derivative, or combinations thereof, said plurality of one micro-structures including a plurality of micro-needles, said plurality of micro-needles formed of said polymer and said biological agent;
   c) expanding said medical device until said medical device at least partially engages an inner surface of a body passageway of said vascular system and causes said plurality of micro-needles to at least partially penetrate into said body passageway and to directly introduce said biological agent in said penetrated region of said body passageway; and,
   d) allowing said patient to recover from the surgical procedure with no use or short term use of less than about forty days of post operative body-wide anti-platelet and/or anti-coagulation therapy.

17. The method as defined in claim 16, wherein said biological agent includes one or more agents selected from the group consisting of trapidil, and trapidil derivatives.

18. The method as defined in claim 17, wherein a plurality of said micro-needles includes an internal portion and an external coating that is formed on an outer surface of said internal portion, said external coating including said polymer, said internal portion including said biological agent.

19. The method as defined in claim 18, wherein said external coating is only formed of said polymer.

20. The method as defined in claim 19, wherein said internal portion is formed of both said polymer and said biological agent.

21. The method as defined in claim 16, wherein said biological agent includes two different biological agents.

22. The method as defined in claim 21, wherein said biological agents includes at least two agents selected from the group consisting of trapidil, trapidil derivatives, cytochalasin, cytochalasin derivatives, paclitaxel, paclitaxel derivatives, rapamycin, rapamycin derivatives, and combinations thereof.

23. The method as defined in claim 22, wherein said polymer layer includes one or more polymers selected from the group consisting of parylene, parylene C; parylene F; parylene N, parylene derivative, parylene C derivative; parylene F derivative; and parylene N derivative.

24. The method as defined in claim 23, wherein a plurality of said micro-needles includes an internal portion and an external coating that is formed on an outer surface of said internal portion, said external coating including said polymer, said internal portion including said biological agent.

25. The method as defined in claim 24, wherein said external coating is only formed of said polymer.

26. The method as defined in claim 25 wherein said internal portion is formed of both said polymer and said biological agent.

* * * * *